(12) United States Patent
Jernigan

(10) Patent No.: US 11,723,568 B2
(45) Date of Patent: Aug. 15, 2023

(54) MENTAL STATE MONITORING SYSTEM

(71) Applicant: Frictionless Systems, LLC, Cambridge, MA (US)

(72) Inventor: Charles Carter Jernigan, Cambridge, MA (US)

(73) Assignee: FRICTIONLESS SYSTEMS, LLC, Cambridge, MA (US)

( * ) Notice: Subject to any disclaimer, the term of this patent is extended or adjusted under 35 U.S.C. 154(b) by 0 days.

(21) Appl. No.: 17/470,920

(22) Filed: Sep. 9, 2021

(65) Prior Publication Data
US 2022/0071535 A1  Mar. 10, 2022

Related U.S. Application Data

(60) Provisional application No. 63/076,788, filed on Sep. 10, 2020.

(51) Int. Cl.
*A61B 5/16* (2006.01)
*G16H 40/63* (2018.01)
(Continued)

(52) U.S. Cl.
CPC ............ *A61B 5/165* (2013.01); *A61B 5/0205* (2013.01); *A61B 5/02405* (2013.01);
(Continued)

(58) Field of Classification Search
CPC ......... A61B 5/165; A61B 5/163; A61B 5/377; A61B 5/0205; A61B 5/02405;
(Continued)

(56) References Cited

U.S. PATENT DOCUMENTS 4,949,726 A * 8/1990 Hartzell ................... A61B 5/38
                                                                      273/460
9,008,633 B2   4/2015 Varoglu et al.
(Continued)

OTHER PUBLICATIONS

MyTeam: Availability Awareness through the use of Sensor Data, Dec. 15, 2016.
(Continued)

*Primary Examiner* — Lynsey C Eiseman
*Assistant Examiner* — Jessandra F Hough
(74) *Attorney, Agent, or Firm* — Scale LLP

(57) ABSTRACT

A system predicts the mental state of a user using a variety of contact or contactless sensors that measure heart rate, breathing or other data of the user. The mental state may be flow, overload, underload, stress, attention, motivation, valence, arousal, etc. While performing a game-playing task the difficulty of the task is adjusted based upon the predicted mental state of the user. A classifier for classifying a mental state is trained using event marking and ground truth data. Computer usage generates event markers. Game playing is used to simulate a mental state. Interruptions of a user are prevented when the user enters a flow, focused, or effortful attention state by classifying that state and indicating physically or electronically that the user should not be interrupted. Interruptions of a user are also prevented when the user enters a mind wandering state by classifying or predicting that state and indicating physically or electronically that the user should not be interrupted. A cost of interrupting is calculated and displayed. Users may also be coached regarding mental state. Advertisements to the user may vary based upon a classified mental state of the user.

27 Claims, 32 Drawing Sheets

Flow Channel

(51) Int. Cl.
*A61B 5/377* (2021.01)
*A61B 5/0205* (2006.01)
*A61B 5/024* (2006.01)
*A61B 5/08* (2006.01)
*A61B 5/11* (2006.01)
*A61B 5/00* (2006.01)

(52) U.S. Cl.
CPC .............. *A61B 5/0816* (2013.01); *A61B 5/11* (2013.01); *A61B 5/163* (2017.08); *A61B 5/377* (2021.01); *A61B 5/7267* (2013.01); *A61B 5/7282* (2013.01); *G16H 40/63* (2018.01)

(58) Field of Classification Search
CPC ....... A61B 5/0816; A61B 5/11; A61B 5/7267; A61B 5/7282; G16H 40/63
See application file for complete search history.

(56) References Cited

U.S. PATENT DOCUMENTS

| | | | |
|---|---|---|---|
| 9,921,726 B1* | 3/2018 | Sculley | A47B 83/001 |
| 2004/0092835 A1* | 5/2004 | Yasushi | A61B 5/02405 |
| | | | 600/513 |
| 2008/0221401 A1* | 9/2008 | Derchak | A61B 5/16 |
| | | | 600/301 |
| 2011/0066036 A1* | 3/2011 | Zilca | A61B 5/165 |
| | | | 600/300 |
| 2011/0263946 A1 | 10/2011 | El Kaliouby et al. | |
| 2012/0083668 A1* | 4/2012 | Pradeep | A61B 5/6803 |
| | | | 600/300 |
| 2013/0102854 A1* | 4/2013 | Zheng | H04H 60/46 |
| | | | 600/300 |
| 2013/0189661 A1* | 7/2013 | El Kaliouby | G06Q 30/0271 |
| | | | 434/236 |
| 2015/0031964 A1* | 1/2015 | Bly | A61B 5/681 |
| | | | 600/300 |
| 2015/0099987 A1 | 4/2015 | Bhatkar et al. | |
| 2016/0234572 A1* | 8/2016 | Dixit | A61B 5/0024 |
| 2016/0374594 A1* | 12/2016 | Garcia Molina | A61B 5/1103 |
| | | | 600/558 |
| 2017/0262606 A1* | 9/2017 | Abdullah | G16Z 99/00 |
| 2017/0365101 A1* | 12/2017 | Samec | A61B 3/09 |
| 2021/0228108 A1* | 7/2021 | Kinnunen | A61B 5/029 |

OTHER PUBLICATIONS

Deciphering Severely Degraded License Plates, Shruti Agarwal et al.
Time Pressure and Creativity in Organizations: A Longitudinal Field Study, Teresa M. Amabile et al. 2002.
International Search Report for International Application No. PCT/US2021/049693, dated Jan. 25, 2022.
Information Fusion, A survey on big data-driven digital phenotyping of mental health, Yunji Liang, Jul. 26, 2018.
Wikipedia, Pupillary Response, Jan. 13, 2022.
ScienceDirect, Respiratory sinus arrhythmia, 2015.
Li, P., et al., "The peptidergic control circuit for sighing," Nature, vol. 530, No. 7590, pp. 293-297 (Feb. 18, 2016)—Author Manuscript available in PMC Aug. 18, 2016 (26 total pages).

* cited by examiner

Flow Channel

ECG with RR Intervals

Valence-Arousal Circumplex

Novel Flow Channel Model-Stress

Novel Flow Channel Model-Attention

Novel Flow Channel Model-Motivation

FIG. 12 Ectopic Beat in ECG Signal

Breath-to-Breath Intervals

Idealized Respiratory Waveform

Example System

Data Flow

Database Ingestion subjects

| Column Name | Type | Constraint |
|---|---|---|
| id | uuid | Primary key; unique; not null |
| cox | erum | {Male, Female, Other}; not null |
| year_of_birth | int | Greater than 1920; not null | labeled_windowed_sample

| Column Name | Type | Constraint |
|---|---|---|
| id | long | autoincrement primary key |
| subject_id | uuid | foreign key, not null |
| tag | string | 30 chars max |
| time_zone_id | enum | 32 chars max |
| timestamp | datetime | Not null |
| label_start_timestamp | datetime | Not null |
| label_end_timestamp | datetime | Not null |
| label_duration | double | > 0; not null |
| label | string | 255 max chars; not null |
| current_rr_interval | duration | > 0 |
| rr_original_stats_id | long | Foreign key |
| rr_original_time_domain_id | long | Foreign key |
| rr_original_sd_id | long | Foreign key |
| rr_original_frequency_domain_id | long | Foreign key |
| rr_detrended_stats_id | long | Foreign key |
| rr_detrended_time_domian_id | long | Foreign key |
| rr_detrended_sd_id | long | Foreign key |
| rr_detrended_frequency_domain_id | long | Foreign key |
| rr_separated_stats_id | long | Foreign key |
| rr_separated_time_domain_id | long | Foreign key |
| rr_separated_sd_id | long | Foreign key |
| rr_separated_frequency_domain_id | long | Foreign key |
| br_type | enum | {inspiration, expiration} |
| br_half_interval | duration | > 0 |
| br_full_interval | duration | > 0 |
| br_stats_id | long | Foreign key |
| activity_stats_id | long | Foreign key |
| keystroke_count | int | >=0 |
| left_click_count | int | >=0 |
| right_click_count | int | >=0 |
| mouse_scroll_count | int | >=0 |
| mouse_move_count | int | >=0 |
| input_window | duration | > 0 |

Database Extraction

FIG. 22A int_statistics

| Column Name | Type | Constraint |
|---|---|---|
| id | long | Primary key; unique; not null |
| min | int | Not null |
| max | int | Not null |
| mean | int | Not null |
| standard_deviation | int | |
| coefficient_of_variation | int | Not null | time_domain_statistics

| Column Name | Type | Constraint |
|---|---|---|
| id | uuid | Primary key; unique; not null |
| pnn50 | float | Not null |
| pnn20 | int | Not null |

*FIG. 22B* double_statistics

| Column Name | Type | Constraint |
|---|---|---|
| id | long | Primary key; unique; not null |
| min | int | Not null |
| max | int | Not null |
| mean | int | Not null |
| standard_deviation | int | Not null |
| coefficient_of_variation | int | | sd_statistics

| Column Name | Type | Constraint |
|---|---|---|
| id | uuid | Primary key; unique; not null |
| sd1 | float | Not null |
| sd2 | int | Not null |

*FIG. 22C*

MENTAL STATE MONITORING SYSTEM

CROSS-REFERENCE TO RELATED APPLICATIONS

This application claims priority of U.S. provisional patent application No. 63/076,788, filed Sep. 10, 2020, entitled "Mental State Monitoring System," which is hereby incorporated by reference.

FIELD OF THE INVENTION

The present invention relates generally to determining a mental state of a user. More specifically, the present invention uses sensors and physiological data to determine a mental state.

BACKGROUND OF THE INVENTION

Folk knowledge has it that we only use 10% of our brains and for many people, it is actually true. Large parts of the brain are deactivated when anyone lives in a state of constant overload, for example, stress, anxiety, or distraction. This deactivation leads to a significant performance drop. In one study, intense time pressure reduced creativity by 45%, as described in "Time Pressure And Creativity In Organizations: A Longitudinal Field Study."

This contrasts with the feeling of being "in the zone." Renowned researcher Mihaly Csikszentmihalyi studied this phenomenon and named it "flow." Flow produces "a sense of deep enjoyment that is so rewarding people feel that expending a great deal of energy is worthwhile simply to be able to feel it" (Csikszenthmihalyi, 2008, p. 49, in his book "Flow: The Psychology of Optimal Experience," published by Harper)

FIG. 1 is a Flow Channel diagram 10. Flow occurs at the balance of challenge and skills (e.g., at A1 and A4 and in the flow channel 12). If skills are high and challenge low, boredom occurs (A2). If skills are low and challenge is high (A3), anxiety occurs. As skills increase, the challenge must also increase to stay in flow (movement from A1 to A4), as described by Csikszenthmihalyi. Csikszentmihalyi concluded that our mental state shifted due to a changing balance between challenge and skill, as visualized in the Flow Channel diagram depicted in FIG. 1.

Over shorter time frames (minutes or hours), people can shift between states of anxiety, boredom, and overload. The oscillation between these states in the short term is what drives learning and growth in the long term, because challenges must increase as skills increase in order to continue finding flow. The oscillation between states and notion of learning and growth also suggests that it is not possible to be in flow all the time, and that anxiety and boredom are important parts of the growth process.

Csikszentmihalyi's experiments and research into flow have relied heavily on the "experience sampling method" (ESM). In ESM, subjects are interrupted at random times and asked to complete a survey. ESM is inherently destructive, because asking someone whether they are in flow will break the state of flow. In other words, flow has been historically measured by interruption.

More recently, less destructive measurements were tested with an fMRI study which found that during challenge-skill balance (i.e. flow), some parts of the brain like the midbrain become more active while others like parts of the prefrontal cortex and amygdala become less active, as compared to boredom or anxiety conditions. To simulate different degrees of challenge-skill balance, the subjects were required to do mental math problems (Ulrich, Keller, Hoenig, Waller, & GAM, 2014). Although fMRI does not involve interruption, it still requires large, expensive, and specialized equipment. Thus, quantifying mental states is currently intrusive.

Other available systems attempt to measure mental state but cannot identify flow. One system uses keyboard or mouse input and experience sampling. These systems are disadvantageous because they cannot function on various mobile device platforms, they rely upon self-reported "interruptability," and users question the accuracy of these systems.

Other prior attempts to quantify mental state have relied upon wearable devices that can be intrusive. For example, EEG devices to read brainwaves must be worn on the user's head. Other attempts using wearable accelerometers have suffered from accuracy issues. Further, wearable devices have battery life limitations, and users often forget to wear them daily. Finally, many prior attempts use different or conflicting definitions of mental state which are less useful.

Accordingly, system, methods and techniques are desirable that are able to quantify mental states less intrusively, without battery life concerns, with more accuracy, and with actionable classifications, and to perform related tasks.

SUMMARY OF THE INVENTION

To achieve the foregoing, and in accordance with the purpose of the present invention, a mental state monitoring system is disclosed that uses physiological data. The present invention has many advantages, including using less intrusive sensors (such as contactless sensors) in order to make the system easier for users to adopt, compared to the complexity of brainwave devices, and other sensors requiring contact. Leveraging non-contact sensors improves compliance, because users do not have to remember to put a device on every day; non-contact sensors also do not have battery life concerns. Various power optimization techniques are also used for when wearable sensors are available or used. The system also accounts for different mental states, specifically recognizing the value of default mode thinking in addition to other mental states.

In a first embodiment of the invention a system or method classifies the mental state of a subject. Using sensors, any physiological data from the subject is input into a computing device and a computer program extracts features from this data. These features are then fed into a classifier in order to classify the mental state of the subject. The classifier then outputs a probability that the subject has the classified mental state. The classified mental state may be that the subject is in flow, is motivated, is overloaded, is underloaded, is distracted, is using effortful attention, is using effortless attention, is using a default mode of attention, or another mental state. Any or all of the sensors may be contactless.

In a second embodiment of the invention a method or system monitors the mental state of the subject. A heart rate monitor detects the heart rate variability of the subject and a classifier receives features that have been extracted from the heart rate variability. Next, the classifier classifies the subject's mental state by outputting the subject's flow level, stress level, attention level, or motivation level. A breathing sensor may also generate features used by the classifier. Other mental states are possible and any or all of the sensors may be contactless.

In a third embodiment of the invention a method or system monitors the mental state of the subject. A breathing monitor detects the breathing rate of the subject and a classifier receives features that have been extracted from the breathing rate. Next, the classifier classifies the subject's mental state by outputting the subject's flow level, stress level, attention level, or motivation level. A heart rate sensor may also generate features used by the classifier. Other mental states are possible and any or all of the sensors may be contactless.

In a fourth embodiment of the invention a method or system monitors a subject's mental state. A heart rate monitor detects heart rate data and a breathing monitor detects breathing data of the subject. A classifier receives extracted features from the heart rate data and from the breathing data and then classifies the subject's mental state based upon these extracted features. Any or all of the monitors may be contactless.

In a fifth embodiment of the invention a method or system alters the difficulty of a computerized task. While the subject is performing the computerized task the method or system determines the subject's mental which is one of overload, flow, or underload. Next, the system alters the difficulty of the task based in part on the subject's mental state while the subject is performing the task. A trained classifier may be used to classify the mental state of the subject.

In a sixth embodiment of the invention a method or system trains a classifier to predict the mental state of the subject. While the subject is using a computer, the method or system determines the subject's mental state using data from event marking. Physiological data is input into a computing device using sensors and a number of features are extracted from this data. These features are then fed into the classifier to train the classifier using the mental state that has been determined using event marking.

In a seventh embodiment of the invention a method or system prevents a subject from being interrupted. First, a classifier of the computing device predicts that a mental state of the subject is at least one of being in flow, using effortful attention, or being overloaded. Next, the system determines that the subject has stopped performing a task on the computing device and is in an incubation period. In response, the system determines that the cost of interruption of the subject is high and then indicates to at least one other person or another computing device that the cost of interruption is high during this incubation. The indication to another user may be a physical indictor, an electronic indicator, or may use an agent or API.

Throughout this disclosure the words "predict" and "classify" are occasionally used interchangeably. The intention, however, is that "classify" is used to indicate a current mental state of a user whereas "predict" indicates a possible future mental state.

BRIEF DESCRIPTION OF THE DRAWINGS

The invention, together with further advantages thereof, may best be understood by reference to the following description taken in conjunction with the accompanying drawings in which:

FIGS. 22A-D show an example of data representation after database extraction during classifying.

DETAILED DESCRIPTION OF THE INVENTION

The Mind-Body Connection

The brain and body do not work independently, but rather are a system. An example of the influence of the brain and body on each other can be observed in the sympathetic and parasympathetic nervous systems. The sympathetic nervous system is often called the "fight or flight" system, while the parasympathetic nervous system is often called the "rest and digest" nervous system.

Figure 2:
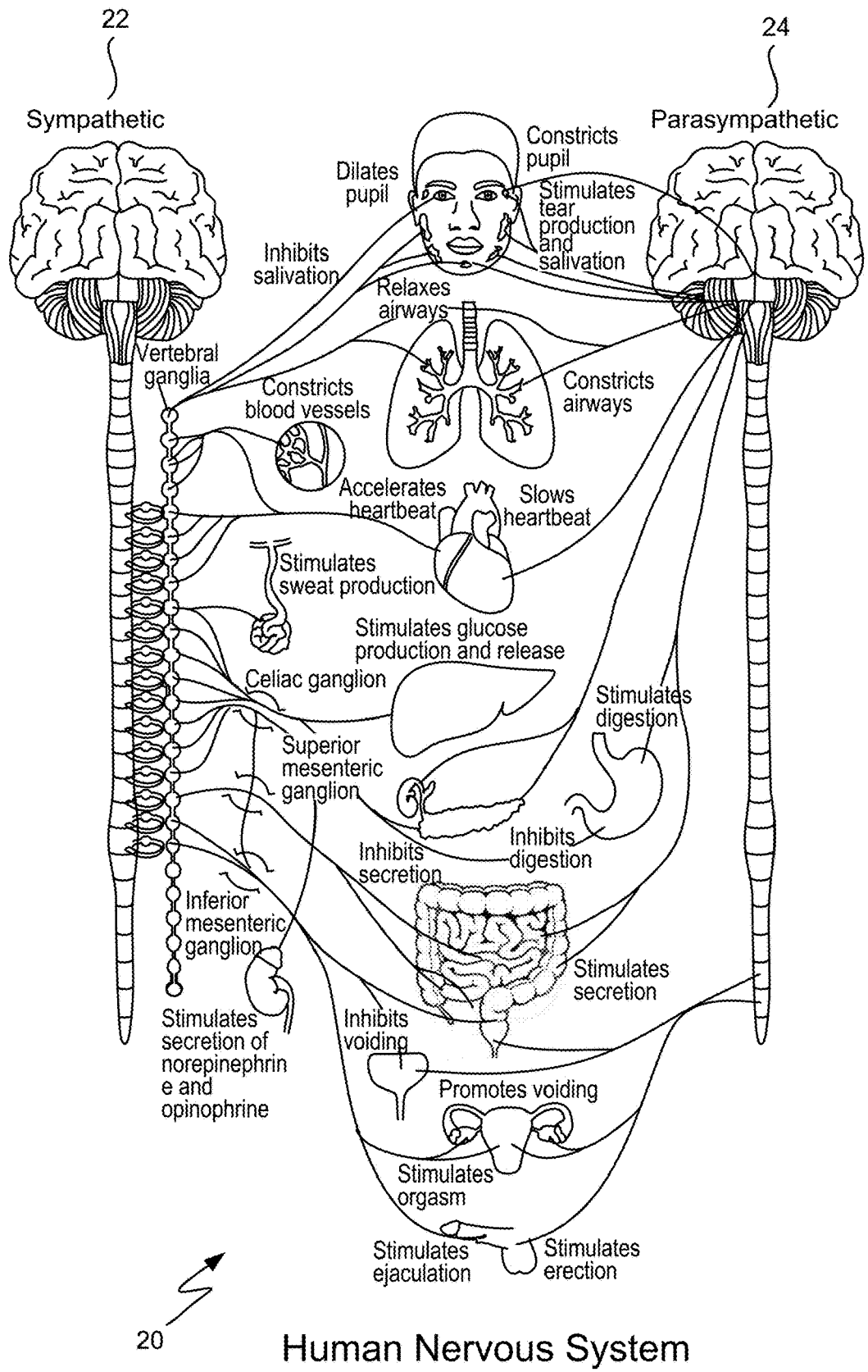
FIG. 2 illustrates the influences of the sympathetic and parasympathetic aspects of the nervous system.

FIG. 2 illustrates the influences of the sympathetic and parasympathetic aspects of the nervous system 20. There is a friendly "tug of war" between these two systems. Based on the combination of the sympathetic 22 and parasympathetic 24 nervous systems, we can gain insights into the brain based on observing variations in the Heart, Lungs, Eyes, and Skin. The heart speeds up and slows down with each beat. This is known as heart rate variability or HRV. HRV is often measured as time between peaks in the QRS wave 36 of an ECG, usually called RR intervals.

Figure 3:
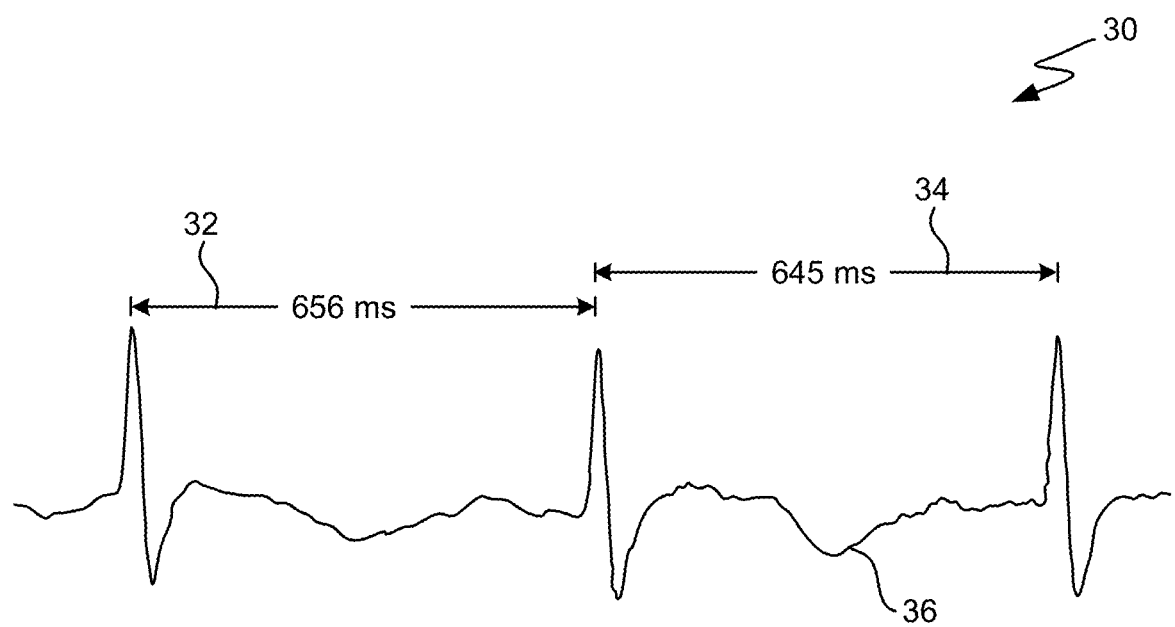
FIG. 3 shows an ECG with RR intervals shown measured in milliseconds.

FIG. 3 shows an ECG 30 with RR intervals 32, 34 shown measured in milliseconds. Sometimes the term "NN interval" is used to differentiate filtering for only normal heart beats. Heart rate variability can also be measured using a photoplethysmography (PPG) sensor, often found in smart watches. Sometimes the terms pulse rate variability (PRV) and pulse-to-pulse (PP) intervals are used instead of HRV and RR intervals. Occasionally the term interbeat interval (IBI) is used. The timing lag between ECG signal and PPG signal is known as pulse transit time or PTT. The sympathetic and parasympathetic nervous systems influence the timings between heart beats, however this is not the only influence on HRV. Physical activity can increase average heart rate. In addition, our heart also speeds up when we breath in and slows down when we breath out, which is called respiratory sinus arrhythmia (RSA).

Figure 4:
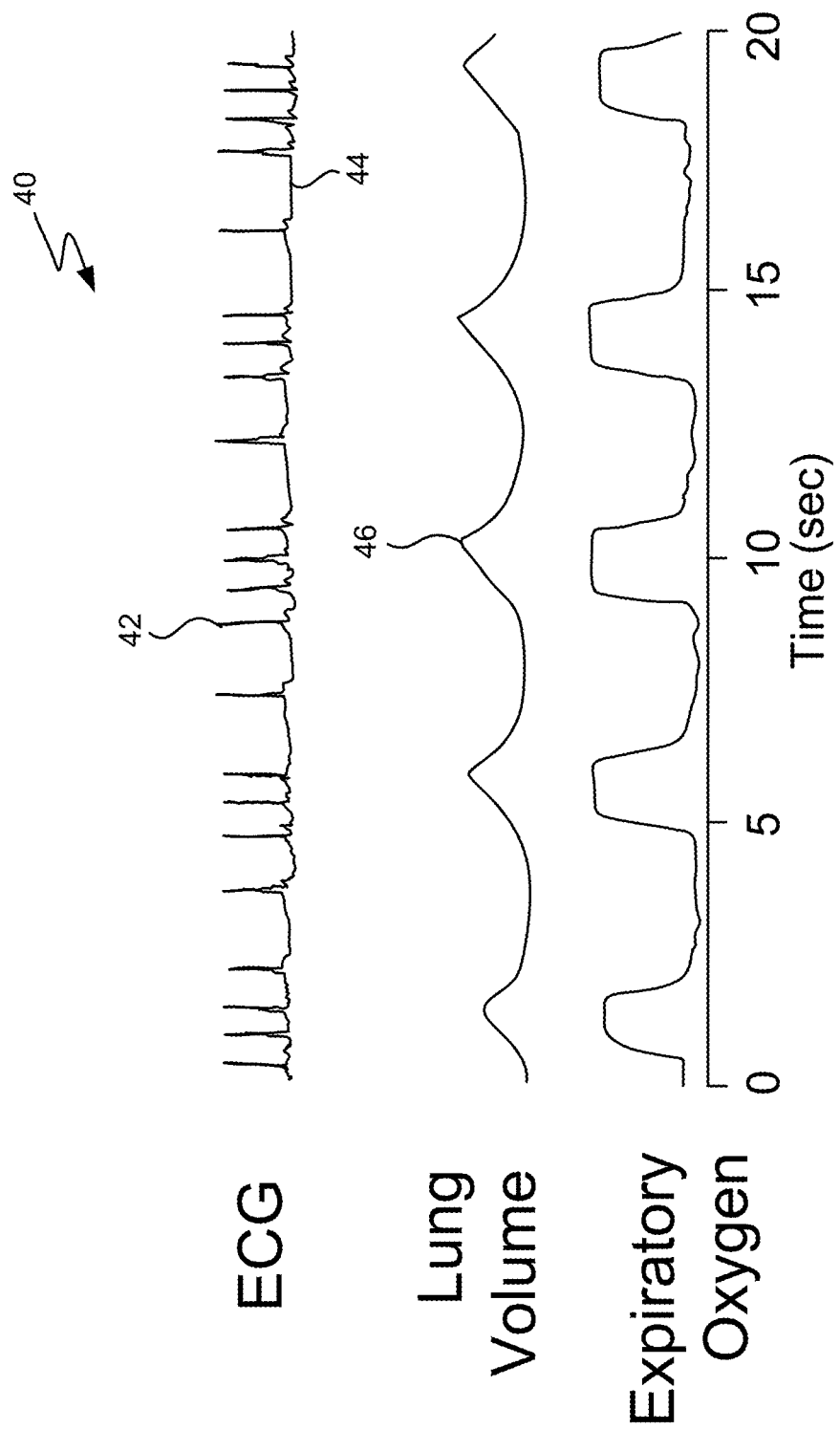
FIG. 4 is a visualization of respiratory sinus arrhythmia from a dog.

FIG. 4 is a visualization 40 of respiratory sinus arrhythmia from a dog. Notice the clustering of heartbeats 42 from the ECG centered around the peak of lung volume (Yasuma & Hayano, 2004). These additional influences on our average heart rate and heart rate variability can pose challenges in isolating just influences from the nervous system.

The lungs exhibit respiratory variability. Our breathing is also more complex than may be initially obvious, with influences from the brain. For example, the brain periodically triggers sighs which are biologically necessary to reinflate alveoli in the lungs (Li, et al., 2016). Sighs can occur under a variety of other circumstances such as sadness, relief, and exhaustion. In animal models, opioids suppressed sighs even at relatively low doses (Bell, Azubike, & Haouzi, 2011).

The eyes exhibit gaze, pupillary size fluctuations, blinking, etc. Eye tracking has been an area of research, as what the eyes are looking at can indicate what people are paying attention to. However, the eyes offer a variety of insights into the brain beyond simply tracking what someone is looking at. While pupil dilation adjusts the amount of light allowed into the eye, there are additional influences on pupil dilation. Pupil dilation is positively associated with increased cognitive load. One study measured pupil dilation in a study of digit recall, which tests working memory by asking subjects to repeat increasingly longer random digit sequences. Pupil dilation occurred when subjects were listening to the digits, and pupils returned to normal during recall of the digits (Kajneman & Beatty, 1966). The size of the pupil also fluctuates with breathing (Ohtsuka, Asakura, Kawasai, & Sawa, 1988). Beyond the pupil, blinking can also potentially suggest ongoing activity in the brain. For example, patients with Parkinson's blink less frequently. Tracking eye blink rate can have advantages because it reflects different types of brain activity compared to other physiological measurements such as breathing and heart rate variability. In addition, eye blink rate can be measured with the use of cameras without requiring body contact. Eye blink rate is less subtle compared to heart rate variability, for example, making it less subject to noise and movement artifacts. Tracking pupil size can have advantages, because pupil size changes are generally involuntary while blinking and breathing can be controlled voluntarily (some of the challenges of managing voluntary breathing changes are discussed in the section Processing—Annotating). Pupillary changes also reflect a different set of cognitive processes compared to eye blinks, breathing, heart rate variability, or EDA.

The skin exhibits electrodermal activity and temperature. The skin is electrically conductive and this conductivity changes based on micro sweating triggered by arousal. This is solely controlled by the sympathetic nervous system, so measuring this electrodermal activity (EDA) is one way to look at sympathetic nervous system activity in isolation (see FIG. 2). Skin is always somewhat conductive, so this is called the tonic level of conductivity. A change in conductivity is called phasic. During a measurement of EDA, there can be specific responses, or phasic changes correlated to a known stimulus. There can also be nonspecific responses (sometimes called spontaneous), or phasic changes that are not due to any specific experimental stimulus (Boucsien, 2012, p. 2). In a study of macaque monkeys, specific responses occurred within 3 seconds of stimulus (Kuraoka & Nakamura, 2010). When measuring a specific response, the amplitude is the height of a single response. Latency is the time between the stimulus onset and the response onset. Rise time is the time between response onset to its maximum. Recovery time is the time needed to recover 50% of the amplitude (Boucsien, 2012, p. 3). EDA responds to breathing by taking a deep breath and holding it for a few seconds; the data should reflect the change within 2-3 seconds once the breath is initiated (Harmon-Jones & Beer, 2009, p. 121). The best EDA signals are collected from the palmar surface of the hands and feet. This makes collecting EDA signals more difficult, because monitoring an activity that requires the hands will introduce noise as the hands move. The feet are also challenging, because shifts in weight on the feet, even when sitting, introduce noise. Less reliable signals can be collected from the wrists. The combination of measurement site, nonspecific responses, and breathing influences on EDA pose challenges in using this as a measure of mental state.

The skin also provides a way of measuring body temperature, which reflects changes in the body and brain throughout the day. For example, temperature fluctuates on longer-term time scales relating to circadian rhythms Skin temperature also fluctuates over shorter time scales based on current activity. Skin temperature of different parts of the body can also be used to look at activity of underlying organs. For example, skin temperature of the forehead can be used as a proxy for brain activity.

Other signals are also relevant. Although not shown in FIG. 2, there are other bodily signals of what a person is doing. For example, overall bodily movement can be used to detect activities like whether a person is sedentary, walking, running, biking, etc.

Figure 5:
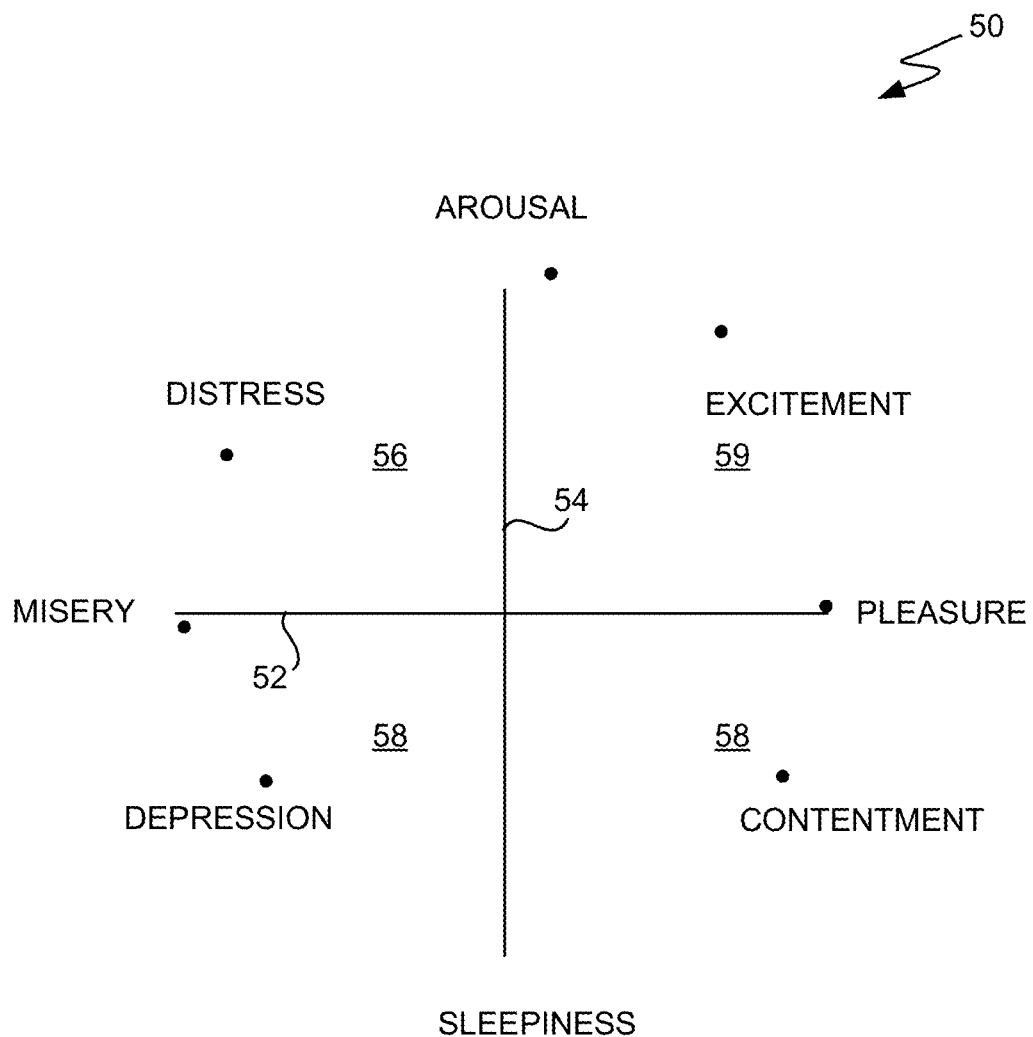
FIG. 5 is a plot of the Valence-Arousal circumplex, with valence on the x axis and arousal on the y axis.

FIG. 5 is a plot 50 of the Valence-Arousal circumplex, with valence 52 on the x axis and arousal 54 on the y axis. The valence-arousal circumplex is another model for human emotional states. In terms of a relationship to measured mental states and the flow channel model, overload may be described as a state 56 of high arousal and negative valence. Flow may be described as a state 59 of moderate/high arousal and high valence. Underload may be described as a state 58 of negative arousal and either positive or negative valence.

A New Flow Channel Model

The following sections walk through a new version of the flow channel model, along with an overview of a system using this model to detect changes in mental state based in part on the mind-body connection.

Adapted to non-emotional terms, Csikszentmihalyi's flow channel model suggests switching between different states: overload, flow, and underload. Although not discussed by Ulrich, et. al., the changes in brain activity suggest that stress, attention, and motivation are relevant to shifting between overload, flow, and underload, thus suggesting a new model.

Consider stress. Research has found that high levels of cortisol given as a tablet and independent of a stressor inhibit flow based on surveys after completing a gaming task. Combining the flow channel diagram, fMRI study (Ulrich, Keller, Hoenig, Waller, & Grön, 2014), cortisol study (Peifer, Schächinger, Engeser, & Antoni, 2015), and the "broaden and build" theory (Fredrickson, 2001), a new flow channel model is realized.

Figure 6:
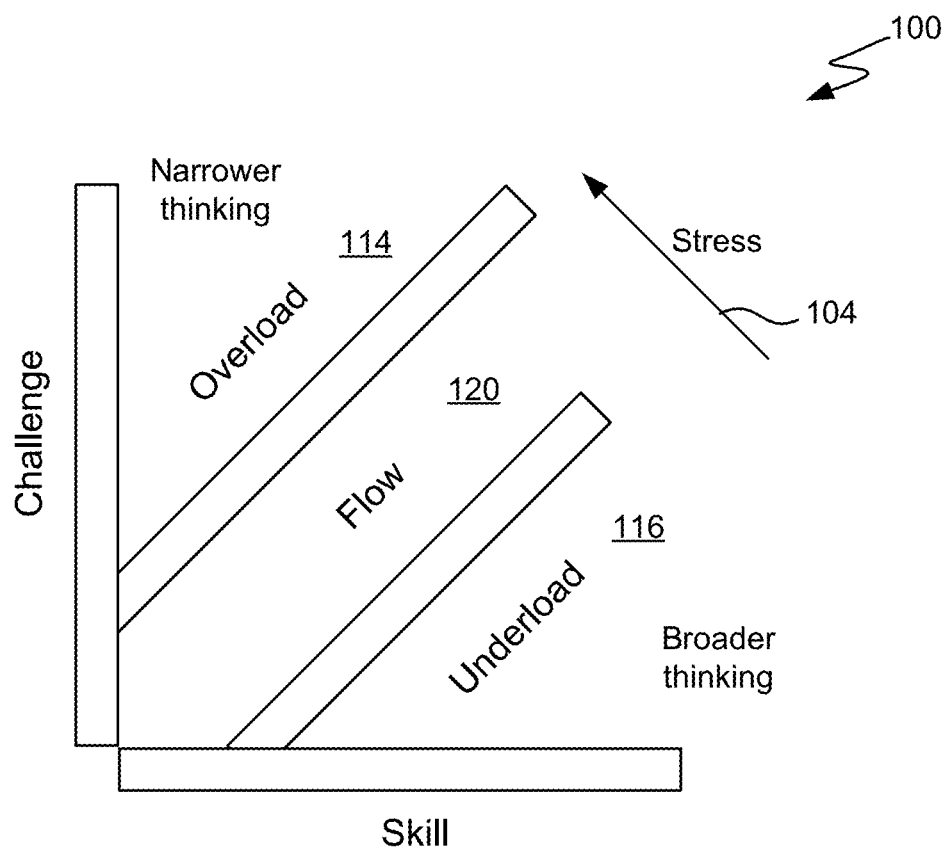
FIG. 6 illustrates a new flow channel model showing how stress can influence shifting between overload, flow, and underload.

FIG. 6 illustrates a new flow channel model 100 showing how stress 104 can influence shifting between overload 114, flow 120, and underload 116.

Now consider attention. When not working towards a task, the brain's default mode network becomes active. This is also known as colloquially as "mind wandering." Some people report having ideas come to them in the shower, which is an example of default mode thinking. Because flow requires focused attention towards a task, this implies that the default mode network is not active during flow. Attention is effortless while in flow, yet effortful in overload. When in overload, attention can suffer from vigilance decrement where fatigue eventually causes attention to lapse. Visualized on the flow channel diagram, a new flow channel model with attention is realized.

Figure 7:
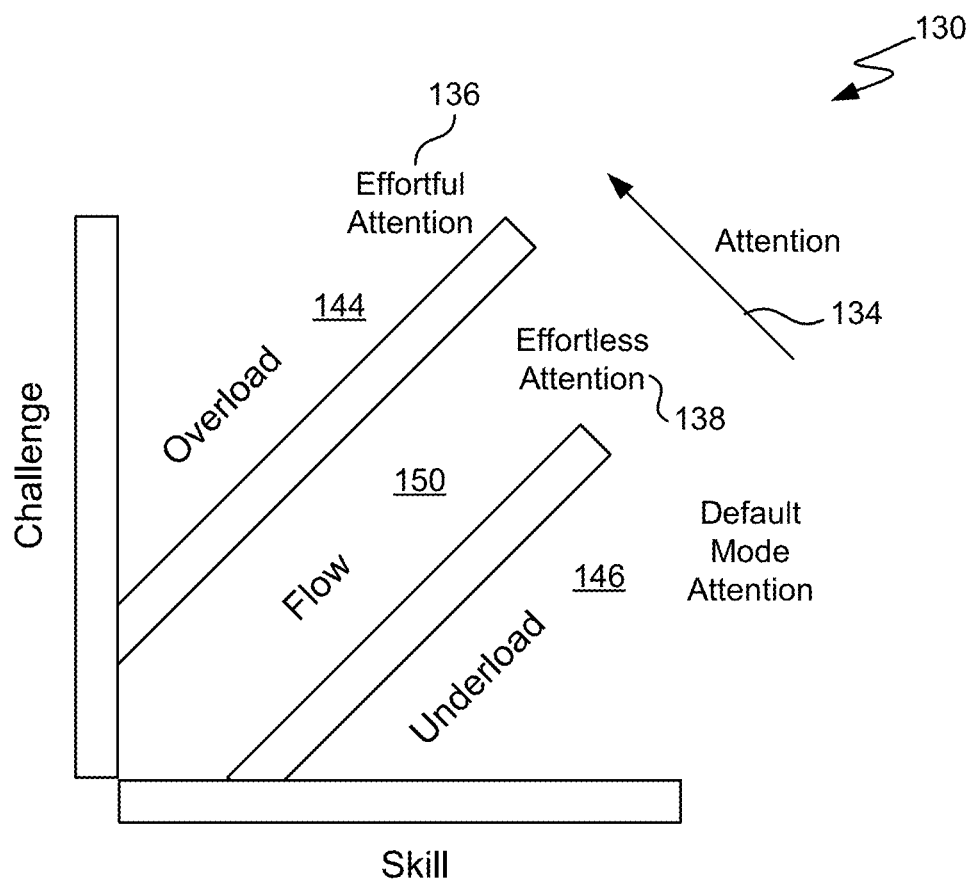
FIG. 7 illustrates a new flow channel model showing how attention can influence shifting between overload, flow, and underload.

FIG. 7 illustrates a new flow channel model 130 showing how attention 134 can influence shifting between overload 144, flow 150, and underload 146. Overload often requires effortful attention 136, such that people get tired quickly and may suffer from vigilance decrement. Flow often involves effortless attention 138, where one can be in flow for a much longer period. Default mode attention refers to the default resting state of the brain which is counterintuitively highly active. In this highly active state, different brain regions and networks are engaged compared to the networks and regions active during flow or overload. This activity facilitates mind wandering and therefore creative insights.

Now consider motivation. Beyond basic biological needs, like food, water, shelter, and sleep, there are two primary types of motivation: extrinsic and intrinsic. Extrinsic motivation involves external incentives. In humans, this might mean money, recognition, or other incentives. Intrinsic motivation, on the other hand, is an internal motivation to do things we want to do because we enjoy them. Research by Csikszentmihalyi found that humans need to be able to pay attention to something in order to become intrinsically motivated by it (Abuhamdeh & Csikszentmihalyi, 2012). So frequent interruptions are likely to inhibit intrinsic motivation 168. External motivators can also inhibit our intrinsic motivation. Time pressure or stress can be a source of extrinsic motivation 166, which can create a feeling of overload and thus push people out of flow.

Figure 8:
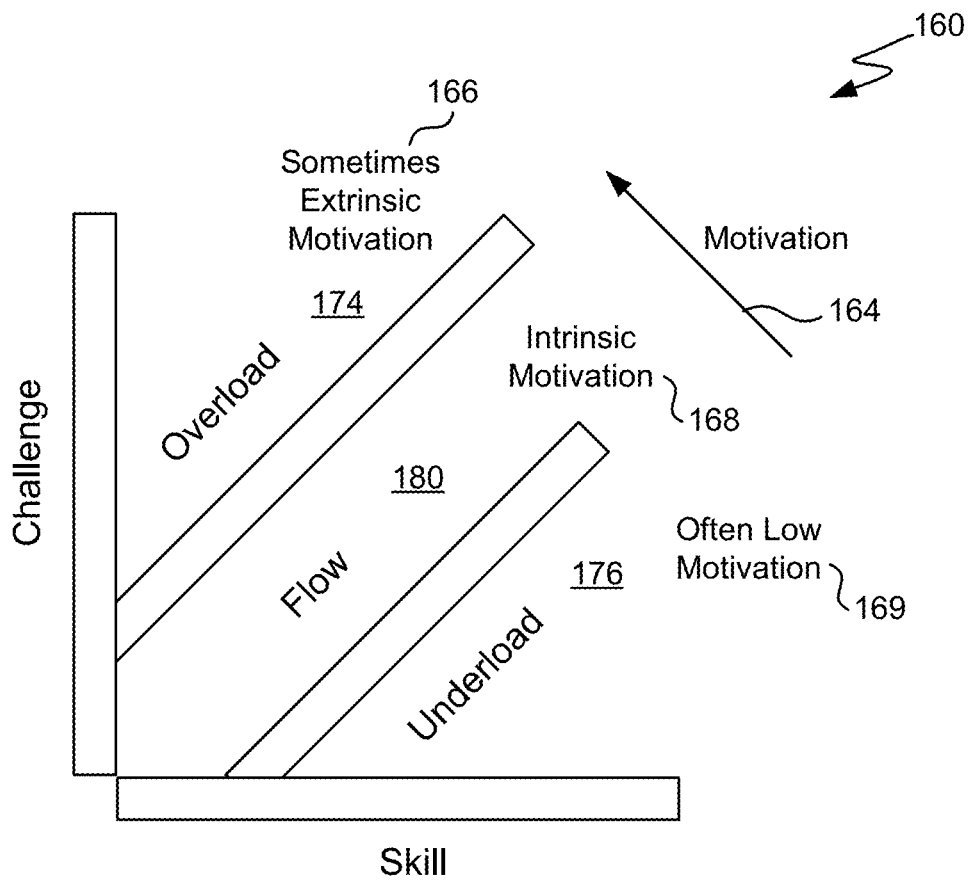
FIG. 8 illustrates a new flow channel model showing how motivation can influence shifting between overload, flow, and underload.

FIG. 8 illustrates a new flow channel model 160 showing how motivation 164 can influence shifting between overload 174, flow 180, and underload 176.

The system of the present invention measures changes in mental states, which enables a variety of use cases. The system consists of several components, to be described in detail in subsequent sections. A brief overview of the components is introduced here and include the following:

1. Measuring Mental State, including overload, flow, or underload. The system also estimates stress, attention, motivation, valence, or arousal.
2. Distributed measurement of mental state: A variation of the system from No. 1, relying of sampled data across a large population to provide broad statistics.
3. Managing Interruptions: By calculating the cost of an interruption based in part on mental state, the system can reduce interruptions during times of higher cost.
4. Coaching: The system can coach users to increase the likelihood of flow experiences.
5. Advertising signals: When in a state of flow, the impact of an advertisement varies. There is an adversarial component here, in that individuals want to be protected from influence while advertisers want to take advantage of when people are most easily influenced.
6. Gaming: The system described in No. 1 can be used to create adaptive and engaging gaming experiences.

The system uses one or more sensors to track physiological and environmental data, such as heart rate variability, breathing variability, sigh rate, electrodermal activity, skin temperature, body movement, eye gaze, pupillary responses, and blinks. Environmental data can include air temperature, carbon dioxide levels, and ambient light levels. The system processes this physiological and environmental data through a pipeline to extract features. The system also can track what the user is doing on a computing device. The system feeds this data into a classifier to identify and predict various mental states of the user.

System Detail—Measuring Mental State

This section describes a system that collects profile information, time-series data, and/or event markers, and performs classifications that can identify things including, but not limited to:
Tasks the user is performing
Mental states of the user, including but not limited to, states of overload, flow, and/or underload
Emotional states of the user, including changes of valence and/or arousal
Changes in stress, such as high stress, eustress (good stress), and/or low stress
Changes in attention, such as loss of vigilance, mind wandering, effortful attention, and/or effortless attention
Changes in motivation, such as amotivation, intrinsic motivation, extrinsic motivation, and/or learned helplessness
Changes in activation of brain networks and brain regions, including but not limited to the task positive network, default mode network, prefrontal cortex, amygdala, midbrain, occipital cortex
Instances of insight thinking
Position in or changes in circadian rhythm
In some embodiments, the system may contain modules or steps for:
Profiling: To gather individual differences such as skills, personality, priorities, preferences. Profiling may be a one-time process or may be an ongoing process.
Sensing: One or more sensors capture physiological and environmental samples.
Interpreting: Converting raw sensor data into a more useful format. For example, peak detection is a type of interpretation.
Processing: Processes data from the sensors to filter, correct, and/or annotate the data.
Event marking: Generates event markers that can be used to correlate with the data generated by sensing. In some instances, data collected along with event markers may also be considered "sensor" data.

Classifying: Combines data from sensing/processing with event marking to build new classifiers, update existing classifiers, and classify new data.

Predicting: Determines when certain classifications are likely or unlikely to occur. In some ways, predicting may be considered a sort of classifier with a longer-term view, while the classifying step before may be thought of as a shorter-term view.

Mediating: Controls the entire system with a bird's eye view.

These modules are described below and while they are listed independently for clarity of discussion, they may be combined. For example, some sensors like chest strap heart rate monitors combine some elements of sensing and interpreting because they capture an ECG signal (sensing) and perform algorithmic QRS detection internally (interpretation), to produce RR intervals (see Sensing—Capture vs. Algorithmic Interpretation for further discussion). To clients receiving this data, the sensor is effectively both an ECG sensor and an RR interval sensor. Additional processing may then be performed by clients receiving these. In some embodiments, feedback loops between these components improve the reliability, performance, and/or power usage of the system.

Profiling

Changes in mental state can be different for different people. For example, something that is boring to one person may be flow inducing for another. In some embodiments, the system profiles to understand what induces different mental states for an individual and what does not. Put another way, profiling provides a priori knowledge to the other components of the system about what scenarios are likely to induce mental state changes for an individual. Once the system knows what it is looking for, that can improve the system's ability to detect specific mental states. For example, a software engineer may identify writing code as flow inducing, while a manager might find collaborative problem solving to be flow inducing. The system may use these individualized profiles to adjust sensitivity to detection of flow while coding for the software engineer, and while in meetings for the manager.

In other embodiments, the system is primed with a baseline profile for a known set of predetermined flow inducers. For example, some embodiments may contain a baseline profile for work performed by software engineers, such as working quietly at a computer developing software. This may be measured using data from the computer such as input device usage, currently running applications, current screen content, or current work task. As another example, the system may contain a baseline profile for athletes. These are just examples and not intended to limit the types of baseline profiles implemented. In some embodiments, the baseline profile is adjusted for the individual based on ongoing assessments of that individual.

In some embodiments, these baseline profiles are determined by analyzing individual patterns over time and aggregated to improve baseline profiles. For example, after collecting data on many software engineers' patterns, the baseline profile may be updated for all the individuals matching that profile.

In some embodiments, some or all historical measures per individual are retained to allow re-individualization of profiles after baselines are updated. For example, an individual has been using the system for a period of time and the profile has been individualized. After enough aggregate data is collected from many users, the underlying baseline for the profile may be updated. Rather than throw away the individualized profile, the user's profile is updated to the new baseline and then the historical data is replayed through the system to achieve an individualized profile on top of the new baseline.

Profiling may occur through active tasks performed by the user as requested by the system, or through passive observation by the system. In some embodiments, a combination of active and passive are used. A specific example of this is described in HRV under the header Processing.

Measures that the system can use include:

The individual's cognitive capabilities. These may be new tests developed as part of the system, or they may be existing tests adapted from standard intelligence tests often performed in a neuropsychological evaluation. An example is the Stroop test.

The individual's working memory capacity.

The individual's ability to maintain executive control.

The individual's personality or behavior style. These may be new tests or tests adapted from existing tests Meyers-Briggs.

DiSC (dominance, influence, steadiness, conscientiousness).

Big Five measures of personality.

Measures of conscientiousness.

Measures of neuroticism.

Sentiment analysis of the individual's communications to determine personality. In some embodiments, this analyzes the individual's written communication. In other embodiments, the system listens to the individual's verbal communication.

Autotelic personality.

Personal history of flow experiences.

Family history of flow experiences.

Genetic information about the user.

Personal history of anxiety.

Historical evidence from previous flow experiences from other similar users.

Medications, drugs, or other substances that the user takes. For example, stimulants such as caffeine and amphetamine increase heart rate and affect the body in ways the system can account for. Beta blockers cause a reduction in heart rate. As another example, drugs such as opioids affect sigh frequency.

Conditions such as having received a heart transplant, as well as the date the heart transplant occurred. Heart transplant patients exhibit low heart rate variability.

Mental health of the user, such as ADHD, PTSD, bipolar disorder, and depression.

Neurological disorders, such as Parkinson's.

Physical fitness of the individual, due to lower heart rates and higher heart rate variability seen in individuals with high levels of physical fitness.

Age, due to changes in heart rate variability with age.

Height and/or weight, as these affect blood volume and thus resonant frequencies of cardiovascular system.

Gender.

Sensing Generally

Sensing collects a time series of physiological and environmental data. This data is collected from a variety of sensors, including heart sensors, lung sensors, and others.

Sensing—Heart

Heart rate and heart rate variability can be measured using a variety of techniques including but not limited to:
- Electrocardiogram (ECG).
- Photoplethysmography (PPG)—An optical sensor pressed against the skin, paired with a light source like an LED. Many wrist-based heart rate sensors use PPG.
- Ballistocardiography.
- Seismocardiography.
- Camera—The skin flushes with each heartbeat, enabling camera-based observation of heart beats based on changes in the skin.
- Head movements—The head moves slightly with each heartbeat, which can be observed with accelerometers or cameras.
- Radar.
- Electromagnetic waves—Radio, microwave, or other electromagnetic waves can be monitored for changes, disruption, reflection, or scattering to detect slight movements of the body caused by heart beats.
- Microphone—A close distance microphone or a long distance microphone array can detect heart beats.
- A combination of these techniques.

For the sake of discussion, the much of the remainder of this document will discuss heart rate variability measured as a series of RR intervals without implying the actual measurement approach. This is not the only representation of this data, and the system implementation may also use other representations. An advantage of this representation is that RR intervals provide a portable way to represent HRV across different types of sensors, such as ECG, PPG, as well as other sensing methods. This allows downstream processing to operate on a variety of different sensors.

PPG power optimization may be used. In some embodiments, the system may use a PPG sensor for tracking heart rate variability. Because PPGs are often embedded in wearable devices with small batteries, battery life of the device can matter significantly. In some embodiments, the system may optimize for battery life in a number of different ways. A dominating factor in PPG power usage is sampling rate, as PPGs generally include a light source such as a LED that fires to illuminate the skin for each sample.

In some embodiments, the system may use multiple colors of light (e.g. red, green) or different light intensities to optimize for power usage and accuracy based on how difficult it is to get a good reading. For example, color and intensity may vary based on skin tone, movement, required degree of accuracy, and ambient light levels.

In some embodiments, the system uses duty cycling to optimize PPG power usage. In some embodiments, the system cycles sampling on and off. For example, it may sample for one minute, then stop sampling for one minute. Of course, other intervals are also possible. In general, the period during which sampling is active is for at least 30 seconds. This gives the system time to settle into an accurate reading, while also providing a long enough window of data to perform various types of windowed feature extraction during subsequent processing. In some embodiments, where the PPG waveform is used rather than the detected RR intervals, an even shorter time period is possible.

In some embodiments, the system waits for the user to be sedentary for a period before attempting to start sampling. For example, the user may need to be sedentary for 5, 10, or 15 minutes before it decides to take a sample. Of course, other sedentary periods are also possible. In some embodiments, the sedentary period varies based on what the user was doing previously. If the user has recently had time to incubate, initiate default mode thinking, or had an insight, the waiting period may be significantly reduced. In some embodiments, the system stops sampling when the user's mental state cannot be classified such as during exercise when the physical activity will dominate the readings.

To get an average heart rate, a PPG needs to sample at about 25 Hz. However, to get HRV a higher sampling rate is generally required. In some embodiments, the system uses adaptive sampling rates to optimize power usage. For example, the system may use a higher sampling rate when the user is sedentary, so that the system can get HRV. When the user is moving, such as walking or exercising, the system may sample at a lower rate to provide average heart rate to the user. In this way, the system can serve both as a fitness tracker and a mental state tracker.

In some embodiments, other inputs to the system are used to initiate sampling. For example, PPG sampling may begin when the user launches a specific application on a computing device, when the user has been active in an application for a period, when the user has avoided a distracting activity for a period, or when the user manually signals they are ready to start a focused working session. In another example, PPG sampling begins when another sensor is ready for additional confirmation (see the Mediating component).

In some embodiments, the system may interpolate between samples to improve results of interpreting the data, especially when the original sampling rate is sub-optimal or lowered for power management. Types of interpolation are discussed in the section Sensing—Accuracy.

Improving accuracy of a heart sensor is relevant. Historically, a high sampling rate has been required to determine heart rate variability from an ECG, PPG, or other heart rate variability sensor. This makes sense, because as the sampling rate is lowered the error is greater. At a sampling rate of 250 Hz, the error is 4 milliseconds. At a sampling rate of 25 Hz, the error is 40 milliseconds. Some heart rate variability metrics are based on smaller differences, such as pNN20 which is based on 20 millisecond timing differences. In some embodiments, the system attempts to use one or more techniques to reduce the error despite a lower sampling rate. The purpose can be to conserve power, to reduce compute costs, or to operate using sensors that have a lower sampling rate such as a Web camera built-in to a computer which may only be able to record at predefined sampling rates like 30 or 60 frames per second.

In other embodiments, the system uses machine learning to upsample the signal. In such an embodiment, the system may be trained by capturing high sampling rate data to train the system to upsample low sampling rate data. In one approach, the high sampling rate data is a PPG or camera sensor capturing at a high sampling rate. The high sampling rate data can then be downsampled and to provide the low sampling rate data to feed into the system. In other embodiments, synthetic high sampling rate PPG data can be generated and downsampled to train the system or augment training of the system.

In other embodiments, the system has other information about user such as breathing rate and uses either the timings of inhales and exhales or the breathing waveform itself to estimate modulations to the heart rate signal. These modulations can include baseline wander, amplitude modulation, or frequency modulation (respiratory sinus arrhythmia) This additional information allows the system to infer more information about a PPG, ECG, or camera-based signal and thus reduce the error. For example, during an inhale heart beats are expected to get faster and thus the system can adjust beat placements to match this expectation. In another example, the expected baseline wander or amplitude modulation can be used to idealize the PPG signal by interpolating the valleys (baseline) and peaks (amplitude) and allow for more accurate detection of inter-beat intervals.

In other embodiments, the system can observe body movements such as slight head movements caused by heart beats. These movements can be observed with movement sensors, such as an accelerometer, gyroscope, or barometer. Alternatively, these movements can be observed using a camera. These movements can be combined with face flush observations, to improve the accuracy of the heart rate variability measurements.

In other embodiments, the system has a camera with a fuller view of the body. For example, a view that includes the head and some combination of extremities like arms, hands, legs, or feet. This wide view allows the system to improve calculation of heart rate variability with lower sampling rates common with cameras commonly available in computing devices. Because different parts of the body are different distances away from the heart, the pulse wave arrives at different body parts at different times. For example, the pulse wave would arrive at the head faster than it would arrive at the hands. And it would arrive at the hands faster than it would arrive at the feet. Because these arrivals are all captured with the same camera, they may appear in different frames of the video. The system can independently estimate the propagation delay for each body part, along with the arrival time at each part of the body, to interpolate a higher accuracy placement for the heart beat timing.

Sensing—Lungs

Breathing can be tracked by the system in a variety of different ways, including but not limited to:
 Airflow sensors to measure airflow in and out of the nose or mouth
 Strain gauge sensors placed around the thorax, abdomen, or both to detect the expansion and contraction of the body.
 Respiratory inductance plethysmography (RIP).
 Accelerometers placed at the thorax, abdomen, or both to detect movement of the body during breathing.
 Cameras that monitor the change in the size of the body during breathing.
 Infrared cameras that monitor the temperature around the mouth and nostrils.
 A bioimpedance sensor.
 A pulse oximeter or $SPO_2$ sensor that measure changes in blood oxygenation.
 ECG derived respiration, using the relative change in position of ECG sensors caused by breathing. The change in signal may be identified from baseline wander or amplitude modulation.
 Respiratory sinus arrhythmia, using the fluctuation in heart rate variability to identify breathing. This is a form of frequency modulation.
 Changes in pupil dilation, as the pupils fluctuate with each breath.
 Radar.
 Electromagnetic waves—Radio, microwave, or other electromagnetic waves and can be monitored for changes, disruption, reflection, or scattering to detect movements of the body caused by breathing.
 Microphone—A close distance microphone or a long distance microphone array can detect breathing.
 Electrodermal activity (EDA)—Deep breaths, such as sighs, are reflected in electrodermal activity.
 A combination of these techniques.

For the sake of discussion, the rest of this document will may discuss breathing rate variability measured as a series of breath-to-breath intervals without implying the actual measurement approach. This is not the only representation of this data, and the system implementation may also use other representations including the original waveform and/or tidal volume.

Sensing—Eyes

Eye tracking can be useful in a variety of ways, ranging from tracking what the user is looking at to involuntary eye behaviors such as gaze, saccades, pupil dilation, and blinks. The eyes can be tracked by the system in a variety of ways with both contact and non-contact sensors, including but not limited to:
 Camera. Cameras may be built-in to a wearable device like glasses, which have a very close view of the eye which is useful for both pupil measurement and accurate gaze tracking. Cameras may also have a wider field of view, like a Web camera, a camera to take photographs of oneself, i.e., "selfies," or a standalone camera. Cameras can also contain a telephoto lens, allowing for a better view of the face or eyes while being farther away from the subject.
 Face recognition sensors, like Apple FaceID.
 Electroencephalogram (EEG), as blinks and eye movements can appear as artifacts on brain wave measurements.
 Electromyogram (EMG), as muscles controlling the face and eyes can indicate eye movements.
 Electrooculography.
 Contact lenses with embedded sensors.

Eye blinking patterns can be correlated with changes in brain chemistry and fatigue. This makes tracking eye blinks a potentially useful physiological indicator of mental state. A blink can be quantified in terms of timing, duration, and phases (eye closing, eye opening). The accuracy of detecting these depends their typical values and the sampling rate of the sensor. In some embodiments, a machine learning algorithm detects blinks from video frames. In other embodiments, blinks are tracked using a camera that captures the user in front of a device, like a Web camera, and applies facial landmark detection to identify the outline of the eye. The size of the outline will change during a blink.

An average blink takes about 572±25 ms (Kwon, et al., 2013). Using a camera at 30 frames per second, the error for the duration is ~66.6 milliseconds, as the entire blink cycle will span multiple frames and error occurs during both the beginning and end frames. A higher frame rate would reduce this error, while a lower frame rate would increase this error. A higher frame rate requires more resources, in terms of running the camera, memory bandwidth, and computing features (e.g. detecting the eye) in the captured frames.

Optimization for blink sensing is relevant. In some embodiments, the sampling rate (and therefore error) can be adjusted based on the current needs of the system. For example, if the system knows the user is already distracted then it may decide to only track total number of blinks with less precision on timing and thus it can adjust the sampling to be less frequent. The reason to continue tracking total blink count may include continuously monitoring baseline blink rate which can change over the course of the day.

In some embodiments, the frequency of computing features can be adjusted independently of the sampling rate from the sensor. A system to detect blinks can store a small buffer of prior samples, for example a few seconds, and perform eye tracking on a subset of the total frames while keeping track of the computed frame-by-frame results. If an interesting event occurs, such as a blink, the system can reprocess just the skipped frames to increase accuracy. For example: imagine a camera sampling at 60 frames per second. Software is performing eye landmark detection on every other frame and storing the results temporarily. This effectively has the computation cost of processing at 30 frames per second. In addition, the unprocessed frames are also stored. When the system detects a blink, it can process previously skipped frames around the detected blink to get an effective accuracy of ~33.3 milliseconds for blink start and end. This approach is not limited to any particular frame rate, and the numbers given are examples of how the system can adapt the number of frames processed. In other embodiments, all the frames between the start and end of the blink event are processed including those previously processed. Some face landmark detection systems use the prior frame to improve landmark detection. While this approach double-processes some frames, it still optimizes overall performance because the time spend blinking is less than the time spent not blinking.

Correction of blink sensing is also relevant. Some users of the system may wear contacts or switch between wearing contacts and glasses. Wearing contacts can alter spontaneous eye blink rate, affecting comparison of different individuals as well as affecting comparison within an individual over time. The system tracks eye blink rate with and without contacts separately to ensure contact usage does not influence eye blink rate metrics. In some embodiments, the system disambiguates by asking the user whether they are wearing glasses or contacts. In other embodiments where a camera sensor is being used, the system uses image recognition techniques to identify whether the user is wearing glasses or not. If the user is known to wear contacts and is not wearing glasses, the user can then be inferred to be wearing contacts.

Sensing—Gaze

Gaze tracking can identify what a person is looking directly at. Gaze can be used as a proxy for attention, as what the user is looking at can be the focus of attention.

Highly accurate gaze tracking generally requires specialized hardware to precisely identify what the eyes are looking at. In some embodiments, accurate gaze fixations and "quiet eye" durations are captured with such specialty equipment. In other embodiments, however, gross gaze tracking can be implemented with less complexity. In some embodiments, the system uses a Web camera to perform gross gaze tracking to identify whether the user is looking at the computing device or elsewhere. In some embodiments, gross gaze away from the computing device and into the distance can be a signal of thinking. In some embodiments, gross gaze downwards can be a signal of either engagement with related materials (e.g. papers) or distraction (e.g. smartphone).

Sensing—Skin

The skin can be tracked in multiple ways, including but not limited to:
Electrodermal activity.
Temperature using a thermometer requiring body contact.
Temperature using an infrared camera or thermometer.
In some embodiments, an infrared camera detects the difference in temperature between the forehead and the tip of the nose. In other embodiments, a skin temperature sensor can be directly in contact with the skin via a wearable device.

Sensing—Movement and Activity

Movement can be tracked in multiple ways, including but not limited to:
An accelerometer, gyroscope, and/or compass.
A step counter.
An activity detector, which reports activities such as walking, running, biking, and driving.
Satellite navigation systems, such as GPS, Galileo, Glonass, BDS, QZSS, IRNSS.
Non-satellite location systems, such as cell triangulation, Wi-Fi triangulation, Wi-Fi time of flight, Bluetooth beacons, and other signals to identify absolute locations (e.g. in a coordinate system) or relative locations (e.g. proximity to a beacon).
Electromagnetic waves—Radio, microwave, or other electromagnetic waves and can be monitored for changes, disruption, reflection, or scattering to detect movement.
A posture sensor embedded in a chair.
A camera to detect body movements.
A camera to detect facial movements.
A facial recognition system, such as Apple FaceID.
In some embodiments, movement is measured in units of acceleration in $m/s^2$. In other embodiments, movement is measured relative to the force of gravity g approximated at 9.81 $m/s^2$. In some embodiments, the distance from the user to a computing device is tracked.

Sensing—Brain

The brain can be more directly tracked in multiple ways, including but not limited to:
Functional near infrared spectroscopy (fNIRS).
Electroencephalogram (EEG).
Magnetoencephalogram (MEG).
In some embodiments, these sensors can be embedded in a multipurpose wearable device, such as a VR or AR headset or a pair of headphones.

Sensing—Accuracy

Some sensors may have a generalized expected level of accuracy. This level may be absolute or relative. For example, an ECG sampling at 1,000 Hz is absolutely more accurate than an ECG sampling at 500 Hz. Different sampling rates imply different levels of error for detecting RR intervals. At 1,000 Hz, the error is 1 millisecond. At 500 Hz, the error is 2 milliseconds. In some embodiments, the system may interpolate between samples to improve results of interpreting the data. The interpolation may be a cubic spline interpolation or a model-based approach. Of course, other interpolation methods are also possible.

If using a variety of different sensors for the same type of data, there can be challenges of integrating that into a single model if the sampling rate is different. One option is to down sample different sensors to the lowest common denominator sampling rate, so that the data is at least consistent. A downside to this approach is that it is lossy, and the possible benefits of a higher sampling rate are lost. An alternative implementation is discussed in the section on Classifier Switching. Meanwhile, PPG sensors are often recognized as being less accurate than ECG sensors regardless of sampling rate, because PPG sensors measure indirect changes to blood volume while ECG measures direct electrical signals from the heart. PPG sensors are therefore relatively less accurate than ECG sensors. In addition, sensors may have transient changes in accuracy because of artifacts. In some embodiments, the system may switch between different sensors based on their absolute, relative, and transient accuracies. This is described further in the Mediating—Sensor Switching section of the Mediating component.

Sensing—Artifacts

An artifact is generally unexpected information captured by a sensor that may interfere with the interpretation of that information. There are several different kinds of artifacts that can occur, although they may primarily be thought of as occurring in two main categories: technical and physiological. A technical artifact is due to noise in the signal. Physiological artifacts are due to something that happened with the body. In the heart, this may be an ectopic heartbeat or atrial fibrillation. For the lungs, a physiological artifact may be a sigh, sneeze, cough, burp, yawn, or hiccup. These are just examples and are not meant to be an exhaustive list of types of artifacts that can occur.

Technical artifacts can vary, depending on the source of the artifact and type of sensor. Some technical artifacts occur due to movement of the sensor or the subject, for example a PPG signal is likely to experience noise when there is bodily movement and some PPG sensors account for this by using an accelerometer to compensate for this movement. A camera based sensor can experience artifacts due to poor lighting or extremely bright lighting (such as the user being backlit by the sun or a bright artificial light), as well as from movement of the camera or subject.

Sensing—Recoverability of Artifacts

Figure 9:
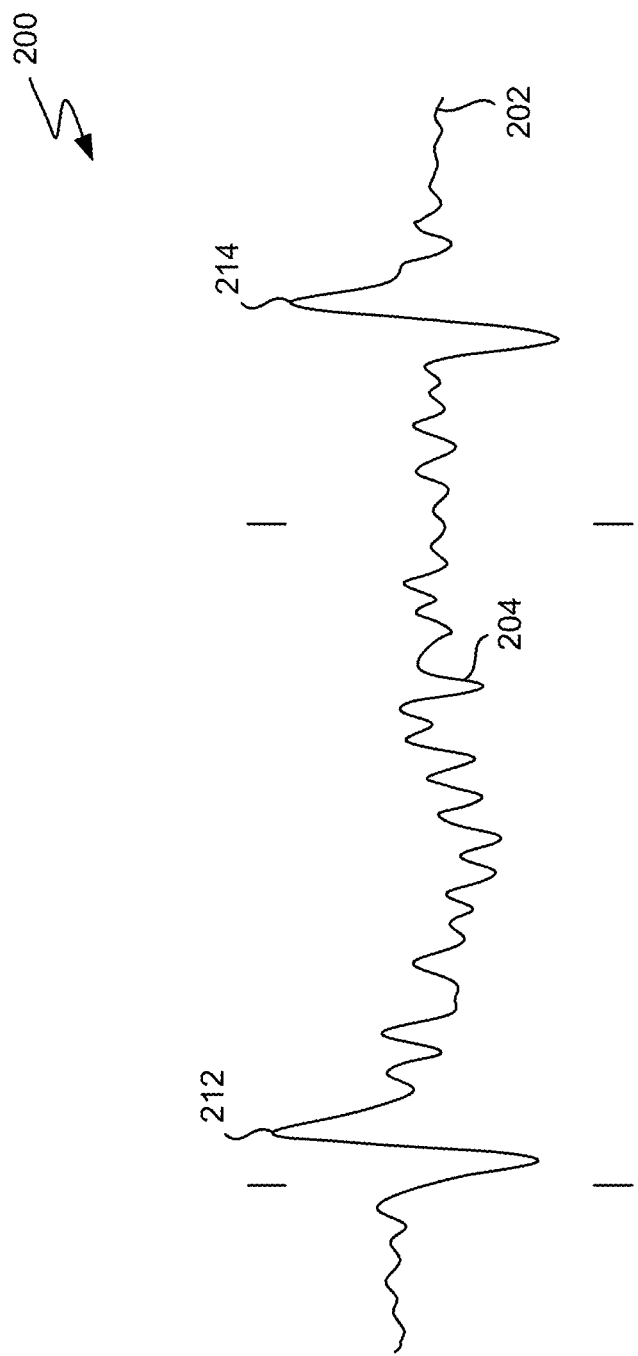
FIG. 9 is a graph of a high frequency noise in an ECG signal.

FIG. 9 is a graph 200 of a high frequency noise 204 in an ECG signal 202. The points 212, 214 are detected R wave peaks, indicating this level of noise can be tolerable.

Figure 10:
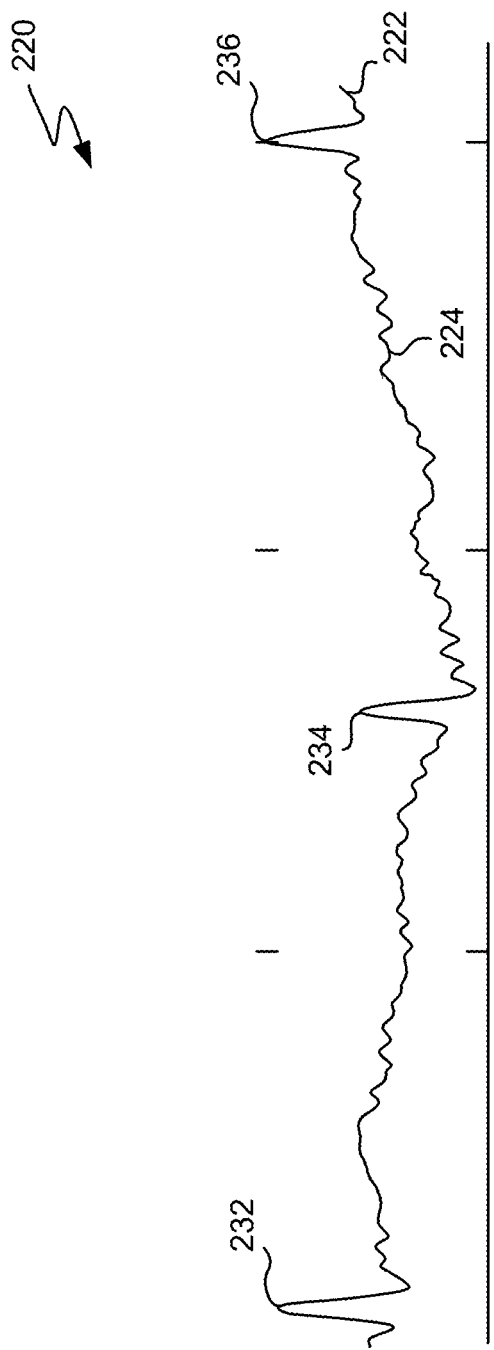
FIG. 10 is a graph of a high frequency noise in an ECG signal, combined with lower frequency noise shifting the baseline of the signal.

FIG. 10 is a graph 220 of a high frequency noise 224 in an ECG signal 222, combined with lower frequency noise shifting the baseline of the signal. This baseline wander is the fact that the peak of 232 is higher than 234, yet we (and computers) can still easily see the peak of 234. The points 232, 234, 235 are detected R wave peaks. This indicates this level of noise can be tolerable. Notice how the center peak 234 is significantly below the others.

Figure 11:
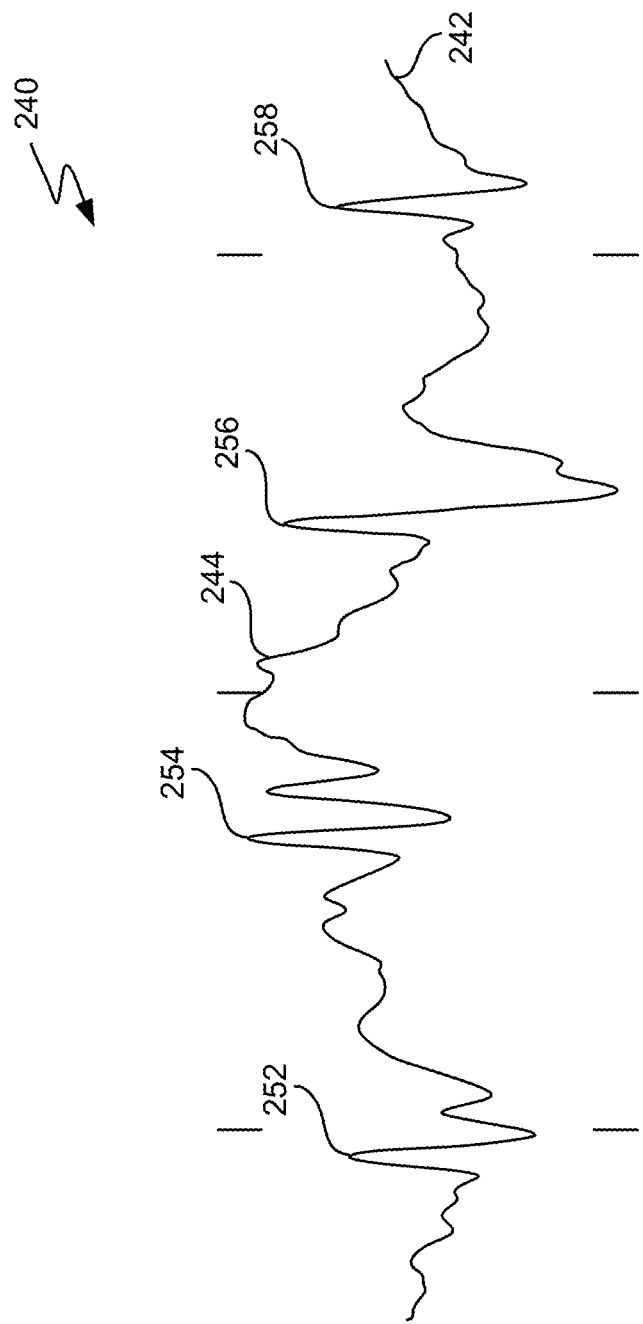
FIG. 11 is a graph of an ECG signal with significant noise.

FIG. 11 is a graph 240 of an ECG signal 242 with significant noise 244. The points 252, 254, 256, 258 are R wave "peaks" that have been detected. Notice the ambiguity of the second detected peak 254. This level of noise may or may not be tolerable.

Some technical artifacts may be highly recoverable, such as seen in FIG. 9. Other technical artifacts can be partially recoverable, such as seen in FIG. 10. In this example, the RR intervals are recoverable but other information that may be derived from an ECG signal like ECG derived respiration may not be available. Finally, artifacts can be unrecoverable, such as seen in FIG. 11 where significant ambiguity exists with the placement of markers for RR intervals. The discussion of how to detect, handle, or manage these types of errors will be covered in the below section on Processing.

Sensing—Physiological Artifacts

Physiological artifacts are changes in the signal due to something that happened within the body. With the heart, this may be a premature ventricular contraction or PVC. Sometimes these are called ectopic beats. In healthy individuals, these can occur occasionally and might look like FIG. 12.

Figure 12:
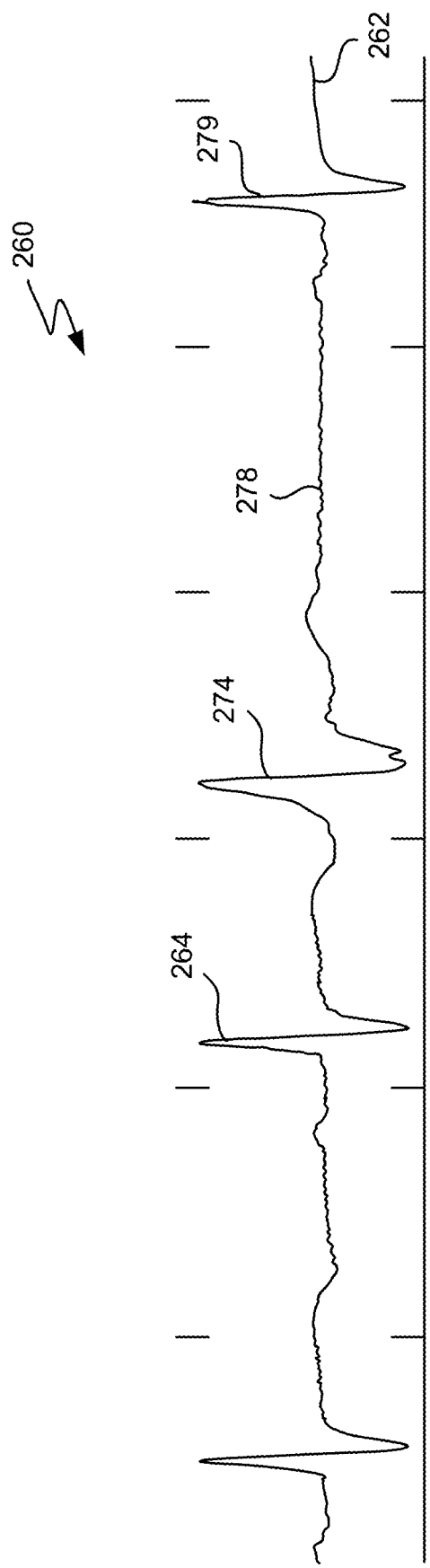
FIG. 12 is a graph of an ectopic beat in an ECG signal.

FIG. 12 is a graph 260 of an ectopic beat 274 in an ECG signal 262. Note the beat 274 has a slightly wider wave and the long compensation delay 278 before the next normal beat 279.

Sensing—Additional Data

Some embodiments of the system use additional data to better understand brain and body chemistry. For example, some embodiments of the system collect one or more saliva samples to identify levels of cortisol or salivary alpha-amylase as an indication of stress. Other embodiments the system may collect one or more urine samples to infer cortisol, dopamine, or melatonin.

Sensing—Subject Identification

In some embodiments, the sensor may detect multiple subjects or not have guarantees that the detected subject is the user of the system. In such cases, the sensor needs to disambiguate the readings to only process data from the user. While this is unlikely to occur for a sensor with body contact, such as a smart watch, it is more likely for a non-contact sensor such as one based on a camera, radio reflections, or radar. With non-contact sensors, a subject who is not the user may come into range of the sensor. Or multiple subjects may come into range of the sensor at the same time. To avoid contaminating the data that is being tracked on behalf of the system's user, some embodiments of the system use one or more techniques to identify the user from multiple possible detected subjects.

In some embodiments, the sensor may be intended to collect data from multiple users. For example, a sensor may be installed in an office setting and multiple users are within range. The approaches discussed here are applicable to identify multiple users simultaneously, as well as to filter out data from non-users that are detected. The accuracy threshold for the sensor can vary based on usage context. A sensor in a private office or home office setting has lower accuracy requirements, for example, because fewer people are expected to come within range of the sensor. A sensor in an open office setting has higher accuracy requirements, because many different people can be in view at once.

Sensing—Subject Identification, Proximity

In some embodiments, a simple heuristic of using the "closest" person is used to identify the user. To prevent far away people from being counted, such an embodiment has a distance threshold beyond which all people are excluded. "Closest" may be defined in multiple ways, depending on the sensor and data available. In some embodiments, the system may directly know the distance a person is away from the system. In other embodiments, the system uses other estimates of distance. For example, a camera being used to detect facial features can use the size of facial features. Even though everyone's facial features are of different absolute sizes, those sizes relative to the perspective of the sensor change very quickly with distance. A face further away will appear significantly smaller and have smaller feature dimensions. "Closest" can also be defined as being near the center of view of the sensor. This would typically have a high probability of being the user for devices such as computers, smartphones, and tablets with front-facing cameras.

Sensing—Subject Identification, Enrollment

In some embodiments, the user goes through an initial enrollment process to help identify the user. If the system is using a camera as part of the sensing process, one method of enrollment uses facial recognition to identify the user. In other embodiments, the system can enroll the user based on capturing heart rate variability or respiration variability data. A "fingerprint" of the user's physiological variability can be captured during enrollment and compared to future readings to identify the user. In other embodiments, the system can enroll the user based on walking gate, body size, voice, or other features that have a reasonable probability of identifying the user and which can be detected by different sensor implementations. In some embodiments, the enrollment is updated over time as more data is captured from the user. This enables the system to adapt to slow changes over time to the user, such as changes to the user's appearance, body size, or fitness levels which may all influence the various methods of identification. In some embodiments, the user is enrolled based on another signal of authentication such as typing a password, authenticating with a fingerprint, face identification, or other identification method built-in to the user's computing device.

Sensing—Subject Identification, Cross-Sensor

In some embodiments, the user can be identified automatically by using data from multiple sensors. For example, consider a user that already has a smart watch or other body-contact sensor. In such scenarios, the system can compare physiological data from the body contact sensor to readings collected by the non-contact sensor to identify the user. In some embodiments, the system will briefly turn on the body-contact sensor to collect readings that can be compared with the non-contact sensor in order to perform subject identification. The system can then turn off the body-contact sensor to conserve battery power and rely more heavily on a non-contact sensor.

In some embodiments, enrollment occurs while the user is sleeping. Because users are not moving much during sleep, motion artifacts are minimized which increases the likelihood of getting accurate physiological variability measurements.

In some embodiments, an additional sensor may be operating at a different sampling rate or have a different level of accuracy compared to a non-contact sensor in the system. In such situations, accommodations may need to be made to data coming from one or more sensors to make them more comparable. For example, consider two sensors that physiological events such as breath-to-breath intervals or heart beat-to beat-intervals. If one sensor has a lower sampling rate or lower accuracy, then the error for the intervals is higher. In such a situation, one embodiment of the system may relax the comparison of the intervals between the two sensors to accommodate the error of the least accurate sensor. A specific implementation of this may look for intervals that match within a default error range, where the default error range is adjusted by the error of the least accurate sensor. Other approaches for handing cross-sensor accuracies are covered in the section Sensing—Accuracy.

In another example, consider two sensors that measure a raw waveform. If one sensor has a lower sampling rate, then it has a greater error. While the waveforms may be converted to physiological events and an error range adjustment may be applied as described above, another embodiment may downsample the raw waveform of the sensor with the higher sampling rate so that the sampling rates match. This would make the error range of each sensor more comparable.

Sensing—Subject Identification, Beacon

In some embodiments, the user is identified by proximity of a beacon on the user's person to the sensor. For example, the beacon may be a Bluetooth enabled smart watch or through an NFC tag.

Sensing—Subject Identification, Combination

In some embodiments, subject identification uses a combination of techniques to identify the user, such as proximity combined with subject enrollment or cross-sensor identification.

Sensing—Capture vs. Algorithmic Interpretation

Sensors capture a physical signal, such as an electrical waveform for ECG or images for a camera. These sensors may also contain an implementation to interpret this physical signal, although not all sensors contain such an implementation. For example, a sensor to monitor the heart such as an ECG sensor may provide just an ECG waveform while another ECG sensor may also provide additional interpretation of that waveform in the form RR intervals or other annotations. An example of this distinction is shown in FIG. 3, where the raw ECG waveform is depicted along with detected RR intervals 32, 24.

In terms of the system being described, "sensors" may emit the original signal, one or more interpreted versions, or both. In some embodiments, where the sensor is known to perform a reliable interpretation, the system can use the interpreted values directly. In some embodiments, where the sensor itself does not perform interpretation or interpretations are known to perform poorly, present system implements this interpretation itself between the Sensing stage and the next stage, which is the Processing stage.

In yet other embodiments where a sensor whose interpretation quality is unknown is connected to the system, the present system will perform its own interpretation and compare the results with the sensor's interpretation. If the sensor's interpretation matches the system's interpretation for a period of time within a predefined tolerance, then the system will opt to use the sensor's interpretation. The system uses this approach because the system's own interpretation is assumed to be more accurate, while the sensor's implementation is assumed to be more power efficient for multiple reasons: 1. Sensors often rely on specialized or low power embedded processors, while the present system may rely on a higher power and more generalized processor. 2. If sensors can emit interpretations instead of the original signal, the volume of data is reduced. Reducing data volume reduces data transmission, and data transmission consumes additional power.

Processing

The time-series data goes through a pipeline of steps to:
Filter the data.
Correct the data.
Annotate the data with features.

These pipeline steps can occur in any order, and some steps may be repeated multiple times. For example, annotating the data with a feature may enhance the ability for some data to subsequently be filtered or corrected. Some steps may not be applied. Filtering and correcting are generally applied because sensor data is non-ideal due to artifacts. Annotations may also flag the data as non-ideal (e.g. an ectopic beat was detected), although generally annotations are intended to be actual features of interest (e.g. a sigh was detected).

Processing—Artifact Handling

As discussed previously, there can be both technical and physiological artifacts (see section Sensing—Artifacts). Both types of artifacts can interfere with interpretation of the data. Multiple approaches can be applied to reduce the impact these artifacts have. Technical artifacts can occur continuously, such as with high and low frequency noise, or can occur with many artifacts in a short period of time. Meanwhile, physiological artifacts may occur less frequently and can be in isolation for healthy users, especially in the case of ectopic beats.

The first step to handling artifacts is to detect them.
Signal classification: If the original sensor signal is available, information about whether an artifact occurred can be derived from the original signal. For example, an ECG signal can be differentiated between physiological and technical artifacts as depicted in FIG. 12 and FIG. 11. Similar differentiation can be made with respiration, EDA, and other sensor signals.
Population physiological norms: Population-wide physiological norms may identify certain artifacts, such as extremely low heart rates, extremely high heart rates, and extreme changes in heart rate variability. Likewise, population-wide norms can be determined for respiration, EDA, and other sensor signals.
Activity based norms: If movement information is available, then activity can be used to adjust the range of norms. For example, if a person is sedentary then the norms may be adjusted to a narrow range. Likewise, if a person is exercising or moving, then the norms may be adjusted to a different range.
Individual physiological norms: After an initial period of measurement, individual physiological norms can be used to create an optimized range of norms. This can be combined with the activity and population physiological norms.
Comparison with additional sensors: For example, a person wearing both a PPG sensor and ECG sensor can see different artifacts at different times. A discrepancy between different sensors can indicate a technical artifact.
Comparison with other types of sensors: In some cases, an entirely different type of sensor is used to detect artifacts. For example, a sensor to detect movement may be used to identify when a PPG signal is likely to become less accurate.
Type-specific algorithms: A variety of artifacts require domain knowledge and type specific detection. Examples that are discussed below include ectopic heart beats and sighs.

In some embodiments, the quality is indicated as a finite set of values such as good or bad, or low quality, medium quality, or high quality. In other embodiments, the quality is a numerical quantity such as a percentage. In some embodiments, artifacts are detected and flagged by adding a segment identifier to each row or sample of time series data. A segment can be used to identify a continuous section of good data, while a segment transition can indicate some kind of discontinuity in the data. A segment may indicate a single bad sample or a large section of noise.

In some embodiments, detection of artifacts is considered a type of annotation. Although subsequent sections will discuss correction and filtering, it is worth nothing that useful information can sometimes be derived from both technical and physiological artifacts. For example, in the absence of an accelerometer or other sensor to detect movement, technical artifacts or temporarily low-quality ECG or PPG signals may indicate that a user is moving.

In some embodiments, an attempt is made to correct the artifact. This is especially useful for individual or isolated artifacts. In some embodiments, artifact correction may "fill in" or correct the odd items in a series for repeatedly occurring events like heart beats and breaths. For such data, the first step is to detect the artifact such as incorrect breath or beat. Identification may be made using either the original signal waveform, the interval series, or both. In some embodiments, the system may look for intervals significantly smaller or larger than surrounding intervals. In other embodiments, the system receives a quality annotation directly from the sensor for each interval.

When such a detection occurs, the system can correct it in different ways. One correction method is interpolation. For an interpolation correction, the artifact or artifacts are replaced with an aggregation function (e.g. average) of nearby values. In some embodiments, the aggregation function is consistently reproducible. In other embodiments, the aggregation function is randomized to prevent the aggregation from being identifiable by downstream processing. In other embodiments, the artifact is suppressed by deletion from the interval series. These deletions do not change subsequent interval durations, but they do reduce the total number of intervals by 1. In some instances, the output of the correction is an enumeration of different types. Each event in the sensor time series may contain both the event value (e.g. interval) along with an annotation of normal, deleted, or interpolated. These annotations can be used by downstream processing to make additional decisions.

Ectopic beats are handled similarly to the process described above, although their detection can be improved, and their handling requires an additional step. Look again at FIG. 12 with a single ectopic heartbeat. In the RR interval series, the system may look for one RR interval being significantly smaller than an aggregation function of surrounding intervals (e.g. above a threshold in standard deviation or an interval shorter than a percentage of the surrounding intervals), followed by an interval that is significantly longer than surrounding intervals (e.g. above a threshold in standard deviation or some percent longer than surrounding intervals). In some embodiments, the ECG signal can also be consulted to further disambiguate ectopic beats which often have a slightly wider QRS shape.

With interpolation, both the ectopic beat and compensation beat can be replaced with a single interpolated RR interval. Note however that while the RR interval itself might be "corrected," the timestamp placement of the intervals may no longer be correct. With deletion, both the ectopic beat and the beat following the compensation delay are deleted.

For example, consider a 1 minute window with 72 normal RR intervals and 1 ectopic beat. The final window would contain 70 beats (deleting the ectopic beat and compensation beat), for a loss of 2.8%. The downstream processing may use multiple ways of computing average heart rate in the window. One implementation may count the beats (70) and divide by the number of minutes (1), yielding 70 beats per minute. Another approach may average the RR intervals of the window and convert the average RR interval to average heart rate which effectively interpolates the average heart rate, minimizing the effect of such deletions.

A similar approach to filling in or deletion may be applied to respiratory artifacts, like sighs, coughs, sneezes, hiccups, or burps. Compensation delays are unlikely following a sigh, so just the single artifact would need to be corrected or suppressed. Additional handling of certain types of artifacts are discussed in the section on Instantaneous Annotations below.

Processing—Filtering

Filtering may include signal level filtering (such as high pass, low pass, or band pass filter). Of course, other signal processing filters may also be used including Butterworth filters or Savitzky-Golay filtering. Filtering can also include processing of annotations in ways that deal with outliers, artifacts, or other problems in the data.

Figure 13:
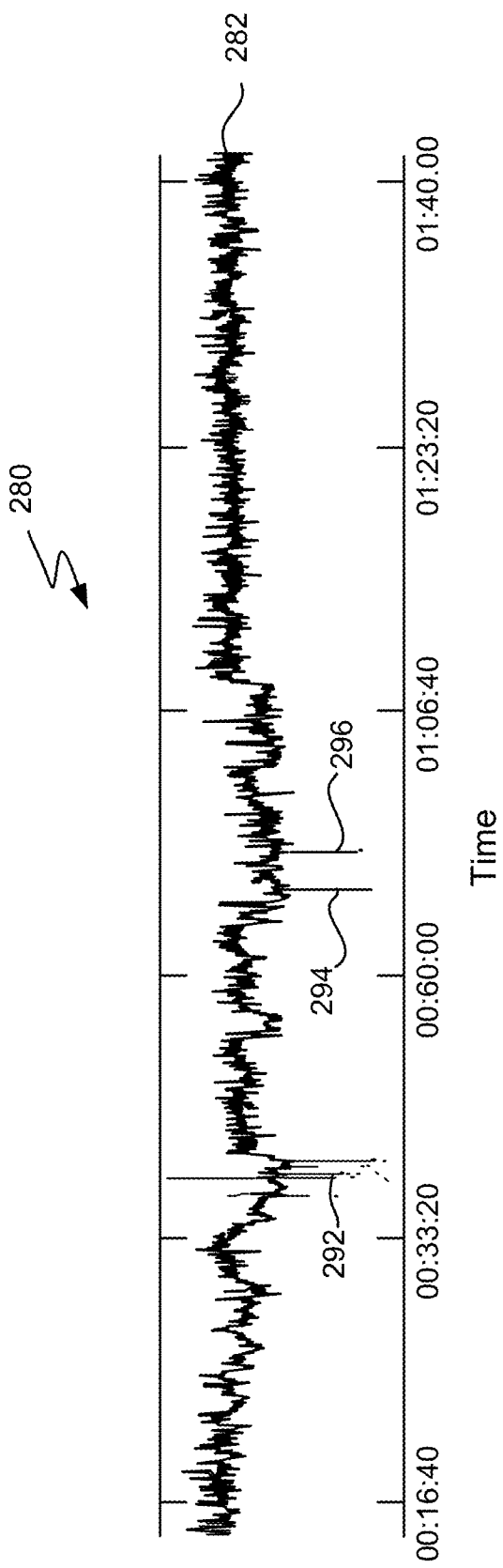
FIG. 13 is a plot that shows an RR interval series plotted over the course of two hours.

In some embodiments, windows of data containing artifacts are suppressed. These dropouts can be preferred to the negative influence of including the artifacts in downstream computation. For example, FIG. 13 shows how technical artifacts sometimes tend to cluster in an RR interval series recording. By losing a small number of windows, the system can be significantly simplified because the remaining data is known to be clean. In other embodiments, windows are only suppressed when they contain a certain number of artifacts above a threshold.

FIG. 13 is a plot 280 that shows an RR interval series 282 plotted over the course of 2 hours. Around minute 35 and minutes 55-60 there are clusters of artifacts depicted as grey spikes 292, 294, 296. As discussed earlier, one form of artifact detection may be the addition of segments to time series data. A benefit of such a segment implementation appears when downstream processing needs to perform statistical analysis on windows of data where even one or two missing points in a window can have a large effect, so downstream processing can skip windows that contain multiple segments.

Processing—Annotating

Features can be absolute, relative, or offset and may be compared. An absolute feature is based on the numerical values of the data in isolation. For example, an absolute feature might be the number of sigh breaths in the last two minutes. A relative value is based on surrounding data. For example, the percentage of breaths in the last two minutes that were sighs. An offset value is based on a baseline. For example, assume a certain number of sighs are expected per minute. An offset value for sighs may be a positive or negative value representing the number of sighs above or below the expected number of sighs. The baseline can be individualized or can be based on population-wide norms. In some embodiments, a population-wide baseline can be used until enough data is available to create an individualized baseline. In other instances, offsets can be generated based on personalized norms provided by the Mediating component as described under Mediating—Baselining.

Features can have different time domains, such as being instantaneous or windowed. An instantaneous feature occurs at a point in time. Although an instantaneous feature occurs at a point in time, it might rely on surrounding context for identification. Some instantaneous features can be considered a type of artifact that is not filtered or corrected but is instead annotated for further processing.

Figure 14:
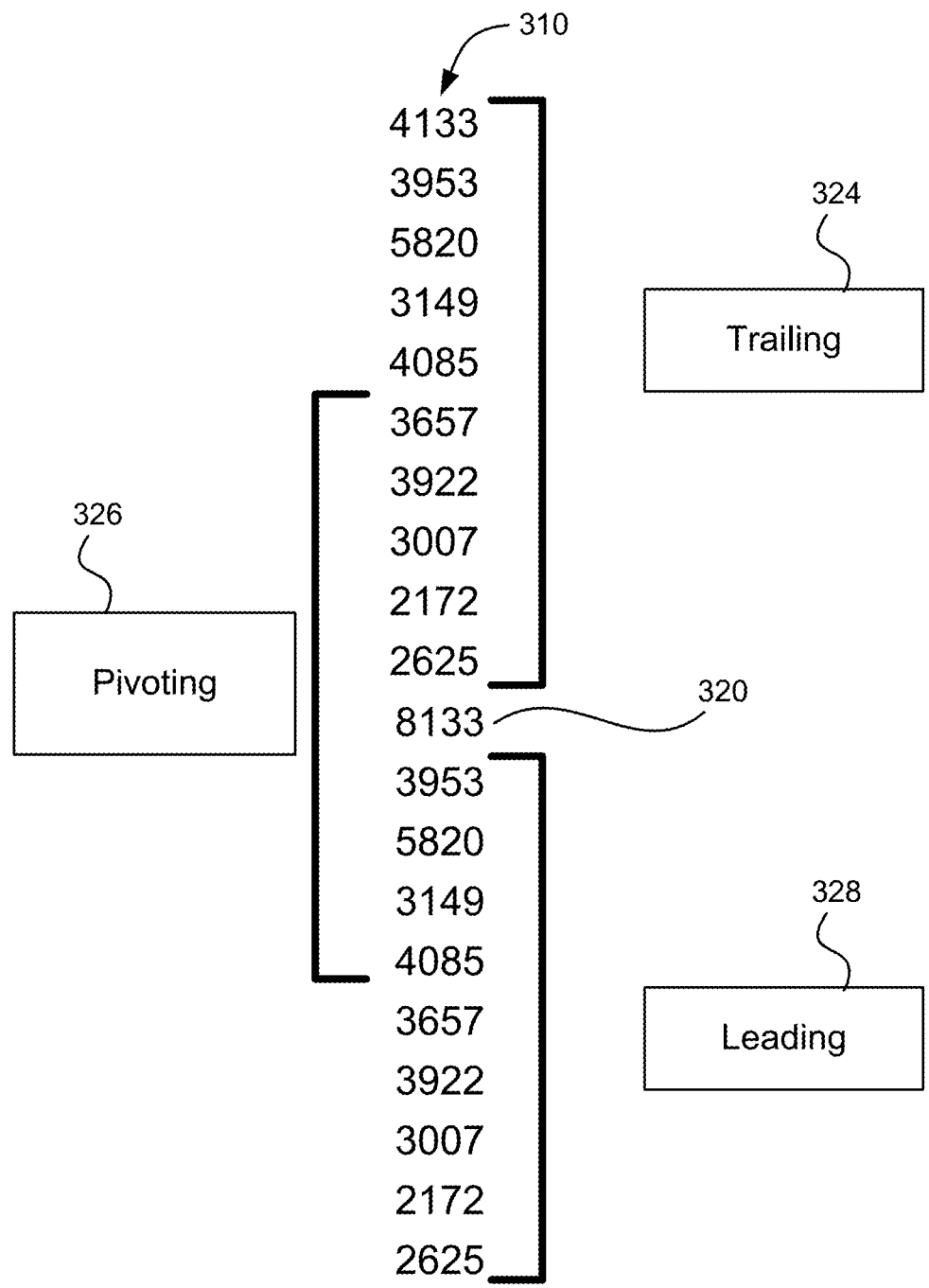
FIG. 14 is an example of different windowing methods around the breath-to-breath interval with a value of 8133.

FIG. 14 is an example of different windowing methods around the breath-to-breath interval with a value of 8133. This example illustrates respiratory features. Consider the list of breath-to-breath intervals 310 measured in milliseconds shown. Note that value "8133" 320 is significantly larger than other intervals. This example may be annotated as an instantaneous feature called a "sigh." While detecting a sigh may require surrounding data to contextualize it (it is significantly larger than the surrounding values), the sigh occurs at a single point in time. Shown are windows 324, 326 and 328.

In some embodiments, sigh detection uses an aggregation function like median or average to look at the duration of surrounding breath intervals. If the breath interval being tested exceeds the average above a certain margin, it may be considered a sigh. In some embodiments, the threshold for sigh detection may be an interval much larger (such as 2x) than the surrounding context. In some embodiments, the surrounding context is adjusted by excluding outliers such as the largest, in order to prevent another nearby sigh from influencing the metrics that the current breath is being compared to. In other embodiments, other detected sighs are excluded.

For breathing variability, there may be lingering influences from an earlier artifact such as a sigh. In some embodiments, lingering influences such as slower or less variable breathing following a sigh may be used to improve the accuracy of sigh detection. The system may also annotate one or more breaths following a sigh with a feature indicating that a "sigh was nearby," as these lingering influences may impact downstream processing. In some embodiments, this is represented as a true or false value. In other embodiments, the sigh distance is represented in number of breaths since last sigh or time duration since last sigh.

In some embodiments, the system tries to detect paced breathing separately from sighs. Paced breathing can be an indication that the user is engaging in a mindfulness practice, which may influence the classifications performed by the system. The system is attempting to classify the brain's unconscious influence on breathing, while paced breathing or mindfulness practice indicates conscious changes to breathing. The first breath of paced breathing may look like a sigh, so paced breathing detection works best with pivoting or leading window. Because sighs most frequently occur in isolation (occasionally up to 3 may occur in proximity), this suggests a window that looks ahead by at least 4 breaths to identify whether a conscious change in breathing rate has occurred. In some embodiments, sighs are detected using a consensus from calculations done independently for leading and trailing data as a simple way to detect paced breathing.

Sighs and ectopic beats are not the only instantaneous features the system can detect. Other instantaneous breathing features the system may detect include sneezes, coughs, burps, hiccups, and yawns. The system may choose to annotate these features. In some embodiments, one or more of these instantaneous features are considered physiological artifacts and their presence may be resolved individually (see Correcting) or they may cause a change in how windows are generated (see Filtering). In addition, instantaneous features may be driven by reflexes such as the startle reflex. Instantaneous features can also include events such as eye blinks. Although the eyes need to blink frequently to maintain a tear film over the eye, the exact timing of blinks can indicate events such as attention shifts. In some embodiments, the system uses the timing of blinks to disambiguate between internal and external interruptions. In some embodiments, the timing of the blink event closest to an event marker is used to identify an internal or an external interruption.

Context is also relevant to annotating. Surrounding context can be leading, trailing, or pivoting. In the example below, trailing uses data lagging behind, leading uses data coming up next, while pivoting uses data surrounding. Each has limitations, as a certain amount of data is needed in order to start annotating. FIG. 14 is an example of different windowing methods around the breath-to-breath interval with a value of 8133. In some embodiments, data is filtered when there is not enough data to provide the necessary context. For example, assuming a pivoting context of size X is needed. Then the first X/2 and last X/2 items are filtered. In other embodiments, all three window types 324, 326, 328 are used to maximize available data. Assuming a context of X items is needed, the system may use a leading window for the first X/2 items, switch to pivoting in the middle, and then switch to trailing for the last X/2 items.

Windowed features are also relevant in annotation. A windowed feature is a feature based on a group of values, such as an average or other aggregation function. As described above in the context section, windows can be leading, trailing, or pivoted. There are a variety of standard windowed features which include, but are not limited to:
Min
Max
Median
Mode
Mean
Standard deviation
Coefficient of correlation
In addition, various data-specific features can be implemented which include, but are not limited to:
SD1, SD2, and SD1/SD2
RMSSD—Root mean square of successive differences
pNNx—Percentage of intervals above or below a threshold x
Triangular index
Frequency domain analysis
ApEn—Approximate entropy
Sample entropy
Multiscale entropy
Shannon Entropy
Detrended fluctuation analysis
Correlation dimension
Independent component analysis
Multiscale principal component analysis
Orthogonal subspace projection
Autoregressive moving average with exogenous inputs (ARMAX)

Each windowed feature may be calculated zero or more times, with any number of window sizes. Each windowed feature may have its own optimal window size. Window sizes can be fixed size based on time (for example, 1 minute) or number of samples they contain (for example, 70 intervals). Windows can slide based on time (move window forward 30 seconds) or based on samples (move forward to the next sample). Sliding step type/size and window size are independent. For example, a window sliding forward one sample at a time may operate on data for one minute. In some embodiments, windows are variable as requested by the classifier or mediator.

In some embodiments, windowed features may exclude certain instantaneous features. For example, a windowed feature from the data listed above may want to skip the sigh value. In other embodiments, a window containing a feature may be skipped entirely. And yet other embodiments may use the instantaneous feature to further annotate the window, such as "this windowed feature contains a sigh." And yet other embodiments might include the percentage of instantaneous features in a window, such as 1.2% of the breaths in this window were sighs.

Other windowed features may choose different algorithms to process the window, when such algorithms are more robust against such artifacts. For example, the system may opt for a different frequency domain analysis algorithm for windows containing ectopic beats. In one embodiment, the system may opt for FFT for frequency domain analysis of windows without ectopic beats and Lomb-Scargle for windows containing ectopic beats. In other embodiments, the system may opt to update the profile (see Profiling) with information that this particular use has a high number of ectopic beats, such that one algorithm becomes used consistently for that user.

For breathing variability, there may be correlation from one breath to the next. For some metrics, window size may be set based on this intercorrelation. In some embodiments, this is a pivoting window size of 7 intervals (3 backwards, 3 forwards) although no windows are generated if any of the breaths in the window are a sigh.

HRV is also relevant in annotation. In some embodiments, the system may detect extremely low heart rate variability combined with high resting heart rate (e.g. above 90 beats per minute), annotating this as a likely heart transplant. In some embodiments, downstream steps may use this annotation to exclude heart rate variability analysis for the user. In other embodiments, the system may raise this as a profiling question for the user to confirm whether the user has received a heart transplant. In other embodiments, the user's profile may be updated automatically to exclude collection and processing of HRV data automatically. In some embodiments, the system asks the user how long ago the heart transplant occurred as reinnervation of the heart over time is possible.

Respiration is also relevant in annotation. The system can detect very slow breathing in range of 4.5 to 6.5 breaths per minute to create an annotation for slow breathing. Such slow breathing can trigger rapid fluctuations in heart rate variability, through an extreme form of RSA sometimes called coherence. In some embodiments, a more precise coherence breathing rate can be estimated by height, weight, and/or gender which influence blood volume and therefore the resonant frequency of the cardiovascular system. In other embodiments, a more precise coherence breathing rate is determined by comparing breathing rates with HRV metrics and RSA to identify the maximum influence of breathing on HRV.

Processing—Crossover

Crossover between one or more types of value (or annotation) occurs to further enhance filtering, correction, and annotation. For example, physiological blips are relevant. In some embodiments, an accelerometer or other sensor to detect movement can be used to detect changes in physiological measurements caused by brief non-exercise movements. For example, shifting in a chair. Such movements can cause either a change in physiological measurements or can introduce noise. In some embodiments, the system will filter segments of data that contain such blips. In other embodiments, the data is annotated as being a blip which can be used by further downstream processing. In other embodiments, these physiological blips are used to create a new segment in the time series, allowing downstream processing to decide how segments are handled.

Sigh detection may also be used. Sighs can cause a "phasic" or short-term change in electrodermal activity, which is reflected 2-3 seconds after the breath is initiated. In some embodiments, these changes can be used to confirm or increase confidence in the classification of sighs from other direct and indirect measurements of breathing.

Data may also be inferred. Some sensors may be indirect and less accurate, yet still adding redundancy to the system. For example, imagine a sensor that directly measures breathing such as a stretch sensor worn around the thorax and/or abdomen or embedded into clothing around these regions. If there are other sensors on the body, breathing may also be inferred from them. Examples include, but are not limited to:

- If ECG signal is also available, an estimate of breathing rate can be determined by the change in distance of the ECG electrodes, known as ECG derived respiration (EDR).
- If the ECG sensor was configured to collect bioimpedance, then breathing can be estimated from this signal.
- If only RR intervals are available, the breathing rate can be estimated from respiratory sinus arrhythmia.
  - In some embodiments, this approach is only used for younger users as the RSA effect decreases with age.
  - In other embodiments, RSA strength is estimated while a different breathing sensor is available, and this determines whether RSA is sufficient to estimate breathing from RR intervals in the future for a given user.
  - In some embodiments, an estimate of where the user is in their circadian rhythm is used to decide whether RSA is sufficient to estimate breathing from RR intervals, as RSA becomes weaker towards the end of the waking period.
- If a pulse oximetry sensor is available, fluctuations in $SPO_2$ can be used to identify respiratory cycles.

Decisions about inferred sensors are made in the Mediating component and discussed under the section Sensor Switching.

Adaptive frequency domain is also relevant to crossover. In some embodiments, a direct or indirect measurement of breathing is used to adjust the frequency band ranges for frequency domain analysis of HRV. HRV has standard frequency ranges for low frequency (0.04 Hz to 0.15 Hz) and high frequency (0.15 Hz to 0.4 Hz). The high frequency range is intended to identify the impact of RSA on HRV. By adapting the frequency range for an individual's current breathing rate, the accuracy of the frequency domain analysis can be increased. In some embodiments, the adaptive frequency domain analysis is continuously updating based on current breathing rate. In other embodiments, the adaptive frequency range is more stable, adapted based on the individual's overall baseline breathing rate so that multiple windows of data are more directly comparable.

Respiratory influence subtraction is also relevant to crossover. In some embodiments, the system removes the respiratory sinus arrhythmia influence from the RR interval series. The benefit is that it allows further analysis to focus on other influences on the heart rather than being "distracted" by influences from breathing. In some embodiments, the signal separation is done using an orthogonal subspace projection. In some embodiments, the respiration signal is the original waveform, passed through one or more optional filters to reduce noise. For example, a Butterworth filter can be used.

Figure 17A:
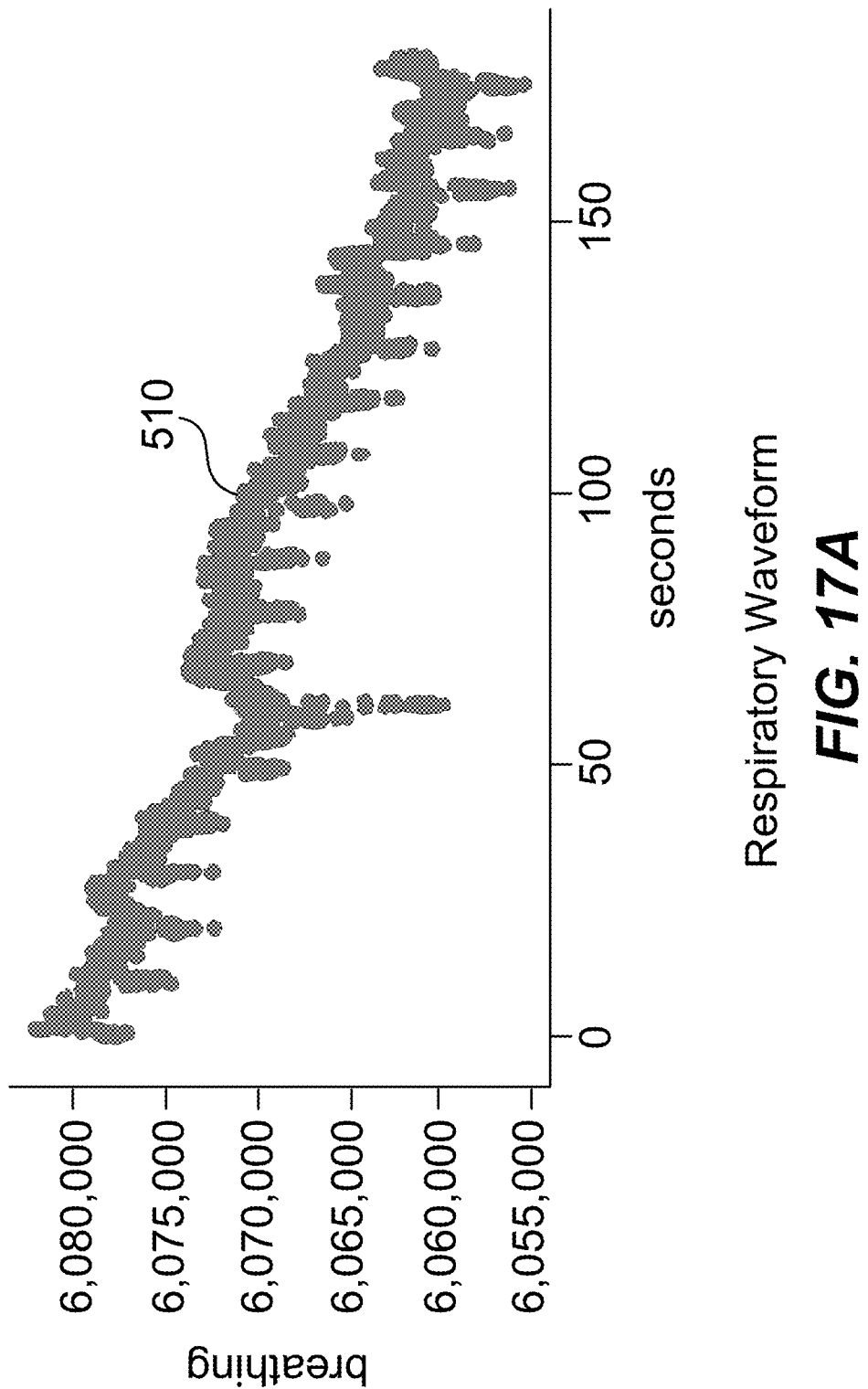
FIG. 17A shows an example of an original respiratory waveform collected from a Zepyr BioHarness device.

FIG. 17A shows an example of an original respiratory waveform 510 collected from a Zepyr BioHarness device.

Figure 17B:
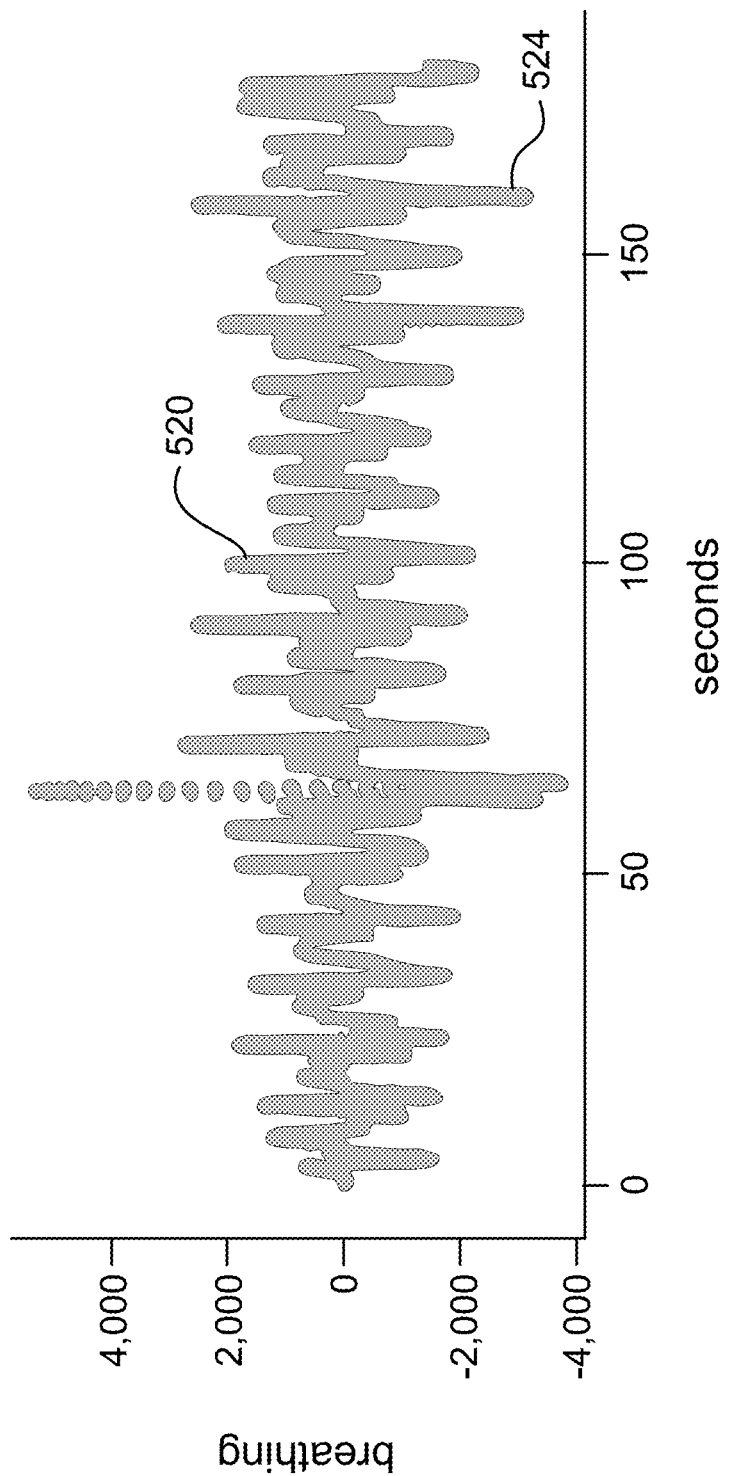
FIG. 17B shows an example of a waveform filtered through a Butterworth filter.

FIG. 17B shows an example of a waveform 520 filtered through a Butterworth filter. Note that even after filtering, the respiratory waveform 520 contains significant noise. In order to reduce this noise and to assist with signal separation, the following technique may be used.

It is realized that the respiration signal is the timings of the inhales and/or exhales, and, these timings may be identified through one more heuristic peak finding algorithms such as the Advanced Counting Algorithm. These timings can be used to reconstruct an idealized respiratory waveform to provide to the separation algorithm.

Figure 17C:
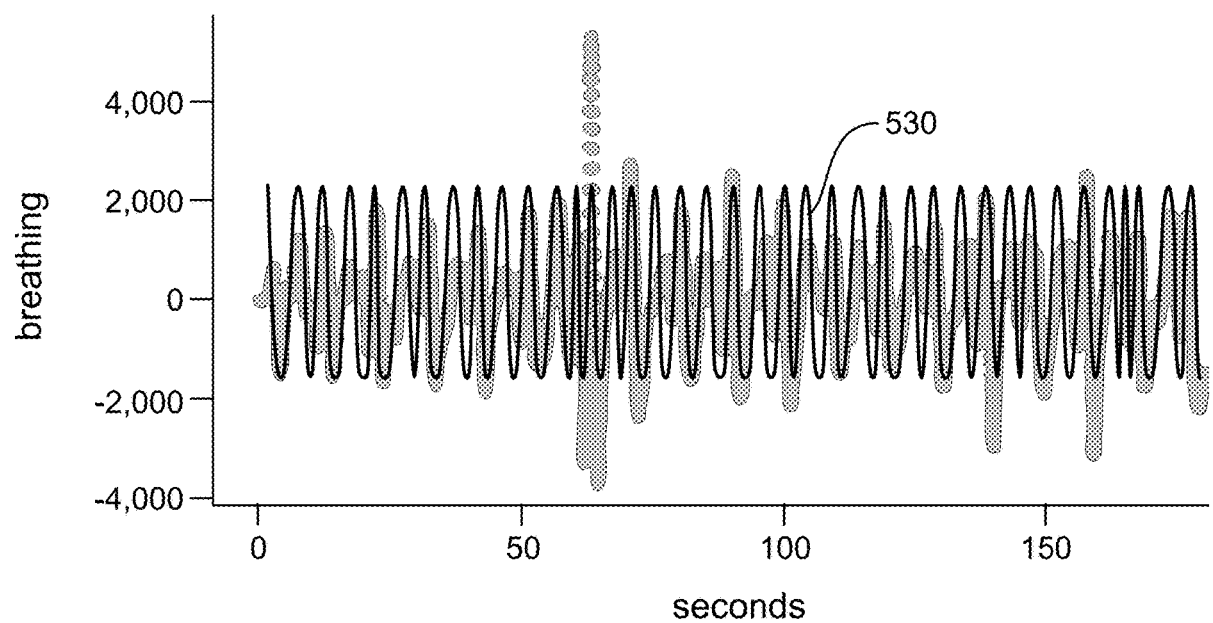
FIG. 17C shows an example of an idealized respiratory waveform.

FIG. 17C shows an example of an idealized respiratory waveform 530 produced by using the above timings and waveform 520. This approach has a benefit of injecting less noise into the respiratory signal separation, as the original respiratory waveform can be noisy even with extensive signal processing and filtering. This approach also has the benefit of requiring significant less data storage or transmission to complete the computation.

Exercise dominance is also relevant to crossover. In some embodiments, sensors such as location, speed, heading, accelerometer, gyroscope, barometer, and/or compass can be used to identify body movements which might indicate that physiological metrics are influenced by exercise dominance as opposed to the influence of the sympathetic and parasympathetic nervous systems as seen at rest. In some embodiments, the user signals explicitly to the system that exercise is about to begin. In other embodiments, the user implicitly signals that exercise is about to begin by signaling to another system that can notify the present system. As an example, Apple Health or Google Fit can act as a hub between applications that track workouts. The purpose is to identify when the sensor data may be dominated by the influences of exercise or physical activity, as opposed to the influence of the brain-body connection that are more readily observed at rest.

Fatigue detection is also relevant to crossover. In some embodiments, the system detects fatigue. One implementation uses a reduction in respiratory sinus arrhythmia compared to earlier in the day. Another implementation uses a change in spontaneous eye blink rate, which increases in the evening in correlation with the wake maintenance zone of the circadian rhythm.

Pupil size is also relevant to crossover, as pupil size fluctuates with breathing. It dilates with inhales and constricts with exhales. In some embodiments, pupil size fluctuations can be used to detect breathing. In other embodiments, pupil size can be combined with other indications of breathing to get a more accurate breathing rate.

Processing—Eye Blink Rate Features

Eye blink rate features that the system may calculate include but are not limited to:
Duration of blink
Ratio of eye closing time versus eye opening time during a blink
Intervals between blinks. In some embodiments, the time of the blink is defined by the "center" of the blink when the eye is closed. In other embodiments, a blink is defined by the start time, the close time, and the end time
Variability between any of the intervals (open to open, close to close, open to close, close to open)
Timing of the blink compared to other sensors, such as event markers Processing—Pupil Features Pupil features that the system may calculate include but are not limited to:
Size of the pupil relative to ambient light
Variability of pupil size
Timing of the pupil size change compared to other sensors, such as event markers Processing—Respiratory Features Respiratory features that the system may calculate include but are not limited to:
Depth of inhale and exhale
Intervals between inhales
Intervals between exhales
Intervals between inhales and exhales
Ratio of duration between inhale and exhale
Variability between any of the intervals (inhale to inhale, exhale to exhale, or inhale to exhale)
Ratio of thoracic versus abdominal breathing
Number or percentage of sighs
Minute ventilation Processing—Antifeatures In some embodiments, the system identifies "antifeatures" which indicate the user may be engaged in an activity such as talking. In some embodiments, talking is identified using a camera and facial landmark detection to identify movement of the mouth. Alternatively, a facial recognition system such as Apple FaceID may be used. In other embodiments, a microphone is used to identify the user is speaking. In some embodiments, talking is identified based on changes in respiration while speaking. In some embodiments, the system has a generic model to identify speaking for all users. In other embodiments, the system calibrates to individual users using one or more techniques. In some embodiments, the user reads aloud a script to the system to monitor for changes to breathing. In some embodiments, this identification of speaking is calibrated to an individual by using naturally occurring moments of speaking that can be tracked by a computing device, such as a video conference or phone call, which is discussed further in the Event Marking section.

Processing—Features as Images

In some embodiments, features can be converted to graphical form such as a recurrence plot, spectral graph, or other visual representation of the data. The purpose of such a visual representation is to enable analysis with a classifier designed to operate on images.

Processing—Original Signal Compression

The original signal coming from a variety of sensors can be large to store permanently. For example, consider an ECG signal captured at 1,000 Hz. In one day, that is 86,400,000 samples. To have the benefits of retaining the original signal, yet lowering the cost of retaining it, some embodiments can use a combination of lossy and lossless compression to reduce the size of the signal. In some embodiments, the original signal is uniformly downsampled to a lower sampling rate. In other embodiments, an adaptive sampling rate is used with a higher sampling rate around regions of interest and a lower sampling rate around less interesting regions. For example, a higher sample rate may be preserved in a window around detected event peaks (e.g. R peaks in an ECG signal). In other embodiments, a higher sampling rate can be preserved in a window around all peaks and/or valleys in the signal, while a lower sampling rate can be used for the rest of the signal. Yet in other embodiments, a fitting function is used to describe the signal with the minimum number of samples preserved needed to keep the fit within a predefined level of tolerance.

Event Marking

Event marking identifies user actions, behaviors, thoughts, and feelings. In some ways, event marking may be considered a specialized type of "sensor" in a broad sense of the word, as it can generate time-series data. In some embodiments, data collected during event marking is treated as sensor data and thus can be an input to both training and classification. In other embodiments, event markers are treated as ground truth labels which are only available during training. And in other embodiments, different subsets of event markers are used for training versus classification. It is possible for event marking and training to be performed on the same computer or on two different computers.

Ground truth event marking is when event marking is highly certain about what the user is doing. Ground truth data may not be necessarily perfect, but it should be as close to ground truth as possible. All other forms of event marking attempt to approximate ground truth through a variety of inferences and potentially indirect means. In some embodiments, ground truth event marking may use fMRI, EEG, MEG, fNIRS, implanted electrodes, and/or other brain scanning, detecting, or imaging technologies. While such ground truth technologies may be used on their own, they are often large, expensive, invasive, or difficult to use to the point of being presently impractical for wide-scale deployment. However, they may be used as part of training the system, by collecting both ground truth along with physiological sensors plus one or more other event markers described subsequently to assist in the process of training a classifier that can operate using only sensors and/or other event markers. In some embodiments, ground truth sensors are used with a relatively small number of users to build a generalized model which can serve all users. In other embodiments, users will use a ground truth sensor to initially train a personalized model, after which ground truth sensors are no longer needed. Ground truth data may also come from the user himself or herself such as the user inputting a label, e.g., "I am focused," "I am in flow," etc., or the system may randomly or periodically prompt the user for a mental state, e.g., "are you in flow?", "are you under stress?", "does time currently seem to pass differently from normal?", "is the current task extremely rewarding?", "are you completely focused on the task at hand?", "are you worried about what others may be thinking of you?", "do you feel in total control of what you're doing?", "do you feel competent enough to meet the demands of the current task?", "are you in a positive mood?", "are you in a negative mood", "are you energized?", etc.

Event Marking Via Computing Device Usage

In one type of event marking, usage at a computing device is tracked by identifying the foreground application that the user is interacting with. This tracking may include the name or identifier of the application. It is possible the user might have multiple versions of the same application installed, such as a stable and pre-release version, so in some embodiments the system identifies these as the same application.

In some embodiments, system applications may be filtered or combined into their initiating application. For example, the user double-clicks on a compressed file in the Finder on macOS. The decompression application is still related to file management, happens quickly, and returns the user back to the Finder. The system contains a list of such applications that can be filtered. In some embodiments, the system learns which tasks should be filtered based on common interaction patterns. In some embodiments, all applications visible to the user are tracked. And in other embodiments, only applications that are significantly visible to the user are tracked (e.g. a majority percentage of the application's window is visible to the user).

And in other embodiments, a task that the user is doing is tracked. For a task like "software engineering," a user might switch between a development environment such as Xcode, Android Studio, IntelliJ, Eclipse, or other such environments, a text editor, a command line terminal, a source code management tool, project management software, documentation, or other related applications. A user may switch between several of these applications, yet still be engaged in the same overall task. To identify the task, some embodiments may use application categories provided by each application. These categories can sometimes be wrong or confusing, so some embodiments may use a predefined list. Yet other embodiments might use user input to manually label application categories.

Input to the computing device, such as keyboard, mouse, game controller, speech recognition, pen, or other input methods may be logged to understand how interactive the user is with the device. In some embodiments, every keystroke, button press, click, mouse movement, utterance, pen stroke, or other input is logged. To preserve privacy, other embodiments may track a count of events by type (e.g. number of keystrokes) as opposed to content. When tracking counts, some embodiments of the system may capture these samples periodically. The period may be exact or flexible. In some embodiments, an additional sample may be collected at the start and end of an application or task in order to associate usage with a per application or per task basis. In some embodiments, keyboard inputs are interpolated between samples. In some embodiments, the contents of the screen are tracked to identify what the user is doing. Screenshots of the content of the screen can be put through an image recognition classifier, to identify their categorical type(s).

Input tracking itself can be monitored through APIs provided by the operating system. Input tracking can also be captured at the connection level (e.g. an intermediary device such as a USB dongle, a Bluetooth dongle, or other intermediary that sits between the input device and the computing device). In some embodiments, the input device itself can be instrumented to track this information. In other embodiments, input is tracked by a wearable device that measures the user's body movements or nerve signals. These alternative approaches may be helpful where instrumentation at other layers of the computing system are not possible, e.g. the computing device the user is interacting with does not allow installation of applications.

In some embodiments, computing device usage includes tasks with other electronic devices such as TVs, smartphones, tablets, virtual reality headsets, augmented reality displays, and other electronic systems. The term "computing device" should be interpreted broadly. In some embodiments, these systems are instrumented directly by software running on the devices. This software may detect when the devices turn on, which applications may be running, and a variety of additional metrics like inputs as already described for computing devices.

In some embodiments, these devices cannot be tracked directly because they do not allow installation of additional software. In some embodiments, these devices are tracked by measuring their power usage which indicates they are turned on. This may be measured directly with a "smart outlet" that sits between the device and the power source. The smart outlet may communicate with the marking system through a network, such as Powerline Ethernet, Bluetooth, Wi-Fi, 5G, or other networking technologies. In some embodiments, usage is measured at the utility box.

In some embodiments, a body camera is used for device usage event marking. The body camera can detect screens, as well as their contents, using image classification. In other embodiments, audio classification is used for device usage event marking. This can be especially useful to track known content such as movies and TV shows which can be identified with audio fingerprinting.

In some embodiments, the user's presence at the computing device is detected based on whether the display is on or off. In some embodiments, the display may be always on but can have an interactive or non-interactive mode, and the system tracks interactivity instead.

In some embodiments, the system tracks when the user is away from the computing device. In such embodiments, the presence of the user is initially detected when the user first interacts with the device by turning it on, waking it from sleep, making it interactive, or otherwise interacting with the device. The user can be inferred as being away when the device goes into sleep, is turned off, goes non-interactive, or a lack of input from the user is detected. Because the system idle detection can have a lag (e.g. a computing device might wait several minutes before going to sleep or low power mode), some embodiments track the last input time and backfill the idle time to the last user input. In other embodiments, the system has its own idle timeout that operates independently of the device and backfills the idle time to the last user interaction.

In some embodiments, the system tracks notifications that the user receives from one or more computing devices. For example, the system may track notifications on a phone, tablet, smartwatch, or computer for services such as email, phone calls, messages, and other sources of notifications. In some embodiments, the system is able to use these notifications, coupled with a task switch corresponding to the source of the notification, to identify whether a switch was driven by such an external notification.

In some embodiments, computing device usage can be used to derive features used by the classifier during classification. Computing device features can include:

Current task
Duration on a task
Number of recent task switches
Interactivity

In some embodiments, computer usage data is used to create additional derived event markers for mental state. For example, consider a software engineer using an IDE to do software engineering work or a writer using a word processor to do writing work. These types of applications may be expected to produce flow experiences at least some of the time. At the beginning and end of the application usage, the user may be inferred to not be in flow because a "warm up" time is common. At some point in between the start and end, the user may have been in flow, although this is not guaranteed. In some embodiments, a portion of these "mystery middle" sections of usage data are used in various ways to approximate ground truth labels for mental state. In some embodiment, this approach requires that an individual has been working on a task for more than a predefined period of time, such as 20 minutes. In some embodiments, the system uses rate of inputs to identify when the user has a predefined duration of a minimum level of input activity, which indicates the user is not stuck. In other embodiments, periods of low input activity are used to identify possible periods of overload. In other embodiments, types of input activity are used to identify periods of underload. For example, scrolling may indicate more passive computer usage.

Event Marking Via Computing Device Usage,
Game Playing

In some embodiments, the tasks the user performs are computer games and can be readily measured. Each game-playing task may have its own metric to track user progress. Examples include, but are not limited to, scores or points, health meters, number of correct answers, accuracy, error rate, how quickly the user completes an aggregate task, time the user stays alive, response time, or other measurable indicators of progress. In some embodiments, the user's natural progression through the game-playing task is observed and the metric is tracked with timestamps. In other embodiments, the user is put through a series of game-playing tasks with known expected levels of difficulty. The metric, along with timestamps and difficulty level, are tracked. These varying levels of difficulty may simulate degrees of underload, flow, and overload. Note that different users may perceive different difficulty levels differently. What is easy for one person might be harder for another person.

Further, the tasks that the user performs for event marking or for training need not be games or gamified tasks, but may be other tasks where the balance of challenge and skill can be adjusted. For example, the task might not be entertainment, but work. Consider the tasks of a TSA baggage screener, an air traffic controller, or mail sorter; there is work that the computer feeds to the human, and the computer can alter the pace of that work. Right now baggage screeners are all on-site and pace is dictated by the passengers. But the screeners could be remote from the machines, just being fed images by computer over a network. If the workload is too slow they are underloaded, too fast and they are quickly overloaded. If the workload is somewhere in the middle, they will have a balance of challenge and skill and will be in flow. Something similar may be done for parts moving on an assembly line based on measured mental state.

In some embodiments, the task adapts in difficulty based on the user's ability. The system tries to automatically find the "sweet" spot. In some embodiments, the difficulty may increase or decrease based on the user's performance on game-playing task, as the system tries to find the optimal level of difficulty that should trigger a flow experience. After the system identifies the optimal level of difficulty, it can then increase and decrease the level of difficulty to approximate various levels of overload and underload. The system records the times of each of these varying states to generate event markers for them. For each state shift, the system will hold a certain level of difficulty for a period of time to capture enough data.

Examples of Game Playing Tasks can Include

Performing mental math problems. Difficulty can be adjusted by increasing or decreasing the size of the numbers to make the problems more or less difficult. The time the user takes to solve the problem and the correctness of the answer can be used to understand the user's perception of the problem's difficulty. Difficulty can also be increased by making the problems timed, such that the problem must be solved within a variable amount of time.

A puzzle game like Tetris. In such a game, the difficulty can be adapted by speeding up the movement of the puzzle pieces.

These are examples, demonstrating how a task's difficulty can be automatically adapted. Other types of game-playing experiences are also possible.

In some embodiments, the game-playing task tracks lapses in attention. For example, the game-playing task may be a vigilance task where the system looks for when the user misses the item of interest. In some embodiments, the vigilance task may be very realistic for real-world tasks. For example, the vigilance task may be very similar to that of security screening like in airports. The advantage of using a game-playing task for this is that the computing device can generate event markers more easily when it is managing the environment the user is operating in, as opposed to trying to observe humans screening baggage in the real world. In some embodiments, the game-playing task interrupts the user with another task in order to identify rapid shifts in attention that might be associated with interruptions common in work such as answering a phone call or responding to an incoming message.

In some embodiments, the game-playing task may attempt to leverage the startle response of the user to confirm the user's mental state. In some cases, the startle event is a natural part of the game-playing experience, while in other cases the startle response is intentionally triggered. The timings of the startle response may vary based on mental state. Once a startle event is triggered, the system can look for physiological responses such as for timings of eye blinks, pupillary response, heart rate acceleration, respiratory variability, and skin conductance responses. Flow is expected to be a state of positive valence and high arousal. In this scenario, faster skin conductance response and heart rate acceleration is expected when startled during flow or overload.

Event Marking Via Computing Device Usage,
Predefined Tasks

In some embodiments, the user performs a predefined task. This is different from a game-playing task, as the predefined task does not adapt prompts based on prior user input. Rather than cycle users through different states like a game-playing task, a predefined task will be difficult and thus measures just focused, vigilant, or effortful mental states. An example of a predefined task may include a cognitive performance tests, such as a Stroop test. Such predefined tasks are scored based on population-wide norms based on the number of correct versus incorrect answers in the time allowed given.

Event Marking Via Semantic Tagging

Another form of automatic event marking is semantic tagging based on other known data. For example: semantic tags may be generated for:
Day of week (Monday versus Tuesday).
Type of day (weekday, weekend, holiday).
Time of day (morning, afternoon, evening, night, lunch).
Weather, such as sunny versus cloudy, because light intensity and spectrum affects circadian rhythms
Day length (short, medium, long), because light exposure timing affects circadian rhythms
Additional zeitgebers, such as social cues.
Circadian offset—Each person has a different response to zeitgebers, which leads to people who wake up early, late, and others somewhere in between. These offsets, along with the timing of zeitgebers, can help identify where someone is in their circadian rhythm.
Season.
If the user is traveling, as user behaviors may be significantly different when outside of the normal environment.
Whether the user is sick, likely to be getting sick, or otherwise experiencing immune activation. Immune system influences on the brain can cause "sickness behavior." Interleukin 1 can cause fatigue, and interferon-gamma can affect social behavior. Mild inflammation triggered by a vaccine has a negative impact on alertness.
Whether the user is wearing contact lenses, which can influence eye blink rate.
Pollen levels, as allergies may impact the immune system, the eyes, and breathing.
Whether the user is sitting or standing. This may be identified by an adjustable desk that reports its height. It may also be detected based on wearable devices. In some embodiments, the system can use a barometer embedded in the device to detect altitude changes. In other embodiments, the system can use an accelerometer embedded in the device to detect movement indicative of altitude changes.

These tags help identify factors that can affect the data classification, allowing these factors to be more easily accounted for without having to necessarily embed the knowledge of these factors into the classifier itself. These tags are more properly considered as sensor data.

Manual Event Marking

Manual event marking techniques, such as experience sampling, have a variety of challenges. First there are gaps in the markers which miss both positive and negative events, as well as their start and end times, because only sensor data from just prior to completion of the survey is able to be marked with any degree of confidence. States like flow can be difficult for subjects to identify a specific start and end time because one facet of flow is a distorted perception of time. There are also a limited number of surveys a user can complete per day, especially given the survey is effectively destructive to the user's prior mental state.

Despite such possible limitations, there are ways to leverage manual event marking to improve the system. To increase the amount of data while reducing the number of interruptions, some embodiments use automatic event markers such as discussed in the section Event Marking via Computing Device to decide when to issue experience sampling prompts or to trigger additional prompts compared to truly random experience sampling. For example, to label flow experiences the system can wait until the user has been active in a single application for an extended period of time, such as 20 minutes, 30 minutes, or 40 minutes. In other embodiments, these prompts are only triggered after the user stops using the application in order to reduce likelihood of interrupting states such as flow. In some embodiments, these prompts are only triggered for certain applications that are likely to be productive such as an IDE or Word processor, but not for communication applications like email or Slack. Regardless of when the prompt is triggered, some embodiments can also estimate the duration of time in a given mental state by expanding on the notion of the "mystery middle" discussed previously. In such cases, the system can exclude some data from the beginning of the application usage as well as data near the end (or near the experience sample), and label a portion of data in the middle of the session based on the experience sample.

In some embodiments, manual event marking is used to train automatic event marking to confirm or reject possible events. For example, the system may start with a generalized model. When that generalized model detects that the user enters a particular state, the system may opt to prompt the user for an experience sampling event to confirm the generalized model was correct and to collect an event marker that can be used to both improve the generalized model and generate personalization for the individual user.

In some embodiments, the user wears a body camera and the resulting audio, video, or photographs are presented to the user to manually identify what the user was doing at the time and possibly ask questions about the user's mental state. In some embodiments, these identifications are done by trained event coders (one example: a system like Amazon Mechanical Turk.). In some embodiments, the user can opt to manually exclude certain days or times in their historical data as "outliers" to be excluded from analysis.

In some embodiments, the user is presented with their calendar to confirm or reject whether they were present at each meeting, whether they were active participants or just observers, and to confirm the start and end times of the meetings. In some embodiments, the user is presented with screenshots or recordings of previous activity on their computing device, phone, tablet, or other electronic device to answer various questions about that activity.

A hybrid is also possible. In some embodiments, a combination of automatic and manual event marking is used. In some embodiments, the system presents the user with automatic classifications made throughout the day which the user can confirm or reject to further train the system. If the system has computing device usage, it can use heuristics to identify the applications that are likely the most productive and the most distracting.

In some embodiments, the system can rely on predefined lists that identify applications as likely highly productive, necessary but not necessarily productive, and distracting. Highly productive applications might include software like document and text editors such as Microsoft Word or PowerPoint or software development environments like IntelliJ, Xcode, Android Studio, Eclipse, or Visual Studio. Necessary but not productive applications might include calendars or other management tools like email, Slack, or other communication apps. Distracting applications might include applications like social media, news, and other applications that are unrelated to work.

Users may have a wide variety of applications on their computing devices, yet the majority of usage is within just a small subset of these applications. In some embodiments, the system calculates metrics about number of activations, statistics on duration of usage such as average and max, and interactivity based on keyboard, mouse, and other input. The system can present to the user a subset of applications that are the most activated, used for the longest period of time, or interacted with the most heavily. The user can identify the applications with labels such as productive, neutral, or distracting. The system can use these labels to improve event marking based on user-defined application categories.

In some embodiments, the system automatically suggests these categories. Distracting applications might be identified by greatest number of activations with shorter average durations. Productive applications might be identified by longer average durations, indicating that the user is focused on them for longer periods of time.

Classifying

The classifying component takes data from sensing, processing, and/or event marking to build new classifiers, update existing classifiers, and classify new data. The classification component of the system has two modes, training and classifying. In some embodiments, the system may start in training and then move to classifying. In other embodiments, the system may switch back and forth. And in other embodiments, the system may do both simultaneously. In some embodiments, system is pretrained so that the system can start providing classifications more quickly to the user. In some embodiments, the pretrained baseline model is adjusted with individualized inputs during training. The individualized inputs can be captured during active tasks performed by the user, or they can be through passive observation. In some embodiments, a combination of active and passive are used.

In some embodiments, some or all historical measures per-individual are retained to allow re-individualization of calibration after pretrained models are updated. For example, an individual has been using the system for a period of time and the classifier has been individualized. After enough aggregate data is collected from many users, the underlying pretrained model may be updated. Rather than throw away the individualized model, the user's profile is updated to the new baseline and then the historical data is replayed through the system to achieve an individualized model on top of the new baseline.

Classifying—Classifier Types

The system may use one or more different types of artificial intelligence classifiers or machine learning. The types of classifiers include, but are not limited to heuristic, neural network, or tabular, or a combination. In some embodiments, the neural network classifier is a long short-term memory classifier (LSTM). The classifier may use both supervised, unsupervised, or a combination of supervised and unsupervised approaches to training. For example, comparing data to event markers is supervised learning.

Unsupervised learning may cluster patterns of physiological data. The combination of both types of learning can identify different mental states within an activity. In other embodiments, heuristics are used to guide the selection of clusters to personalize the system for individual users.

Different people naturally breathe at different baseline rates. A cluster may look at breathing rate and variability to identify what counts as faster or slower breathing rate for that person, as well as what counts as more consistent or less consistent breathing variability for that person. In some embodiments, faster breathing may indicate high arousal, high stress, or effortful attention. In some embodiments, irregular breathing may indicate high stress. In some embodiments, faster and less regular breathing may indicate stress. In some embodiments, slower breathing may indicate low stress or low arousal. In some embodiments, faster and more regular breathing may indicate effortless attention.

Different people naturally blink at different baseline rates. A cluster may look at blink rate and variability to identify what count as faster or slower blinking rate for that person, as well as what counts as more consistent or less consistent blinking variability for that person. In some embodiments, higher eye blink rate can indicate mind wandering. In other embodiments, lower eye blink rate can indicate effortless or effortful attention. And as discussed in the Mediating section, circadian rhythms can influence eye blink rate over the course of the day. Some embodiments of the system use an estimate of circadian rhythm to adapt to shifting eye blink rates throughout the day.

Different people have different natural pupil sizes. A cluster may look at pupil size relative to ambient light to identify what counts as larger and smaller pupil size for that person at a given light level. In some embodiments, relative pupil dilation is used to identify overload, stress, effortful attention, effortless attention, or arousal. In some embodiments, pupil constriction is used to identify underload, default mode attention, or low motivation.

In some embodiments, sections of data for clustering may be generated based on automatically generated event markers such as described in the section Event Marking via Computing Device. In some embodiments, these sections for clustering may be generated on a per application basis. And in other embodiments, sections for clustering are generated by the rules used to select data for the "mystery middle" as described previously. In some embodiments, the classifier may emit a fixed set of known or arbitrary values, such as true/false, low/medium/high, or any other discrete set of outputs. In other embodiments, the classifier may be a regressor which emits a numerical value (continuous). For the sake of discussion, the term "classifier" generically refers to either implementation.

Classifying—Hysteresis

In some embodiments, asymmetry or hysteresis is used to reduce switching between states too quickly or to ease switching back to a state that was entered previously. For example, the initial threshold (i.e., a probability value of a state) to detect a state may be relatively high but once that threshold is met the system may try to be "sticky" in continuing to classify it with lower thresholds. In other words, the thresholds to enter and exit detection of different mental states may be different. For example, consider the system has classified the user's attention as being focused, the user is intrinsically motivated, or the user is in flow. Then suppose the user is interrupted, either externally or internally. The system can detect that focus, intrinsic motivation, or flow has temporarily ended. If the user returns to the previous activity within a short period of time, the system may reduce the thresholds to detect focus, intrinsic motivation, or flow to re-enter that state more quickly. Of course, if a classifier is designed to determine the inverse of a state (e.g., 0% probability of not being in flow instead of 100% probability of being in flow) then a threshold would be increased to re-enter a state. In either case, the second threshold makes it easier to re-enter a state.

In some embodiments, the system can detect whether an interruption is internal or external. An internal interruption is one the user generated, while an external interruption is one generated by an outside source such as a phone call or face-to-face interruption by a coworker. An example of an internal interruption is that the user may get up to go to the bathroom. Although the user may not be in flow while in the bathroom, such a brief interruption may not cause a complete mindset shift such that the user is able to go back to the flow experience once back from the bathroom. On the other hand, if another employee comes by to interrupt the person experiencing flow, that might be considered a large enough interruption to end the detected flow session.

In some embodiments, the system identifies the timing of pupil dilation changes relative to the timing of the interruption to identify whether the interruption was internal or external. For internal interruptions, maximum pupil dilation occurs sooner relative to the interruption. In either case, maximum dilation usually occurs within 1.5 seconds.

Classifying—Prior State

In some embodiments, one or more previous outputs of the classifier can be used as one or more inputs to the classifier. This is different from hysteresis, as this is just using prior state as an input without consideration to changing specific thresholds.

Classifying—Refractory Period

In some embodiments, the system has a refractory period to reduce the probability of rapidly switching between states. The refractory period is time based.

Classifying—Short Circuits

In some embodiments, "short circuits" can be used to quickly switch states even with hysteresis or prior state input. This implies that some inputs to the classifier may have higher precedence over other inputs. Consider a user working at a computing device. The system may be classifying mental state based on physiological measurements. However, if the system also has other information, such as application being used or information from the environment, this may override what is classified based on physiological measurements. As an example, if the user switches to a distracting application, the user receives a phone call, another person interrupts, or the user moves away from the computing device, then the system may use these events to immediately switch states.

Classifying—Classifier Switching

In some embodiments, multiple classifiers are used at different times for different purposes. This switching between classifiers can optimize performance, improve robustness, or enable new use cases.

Classifying—Robustness

While an ideal classifier may use a variety of types of sensor data, there are times when one type of sensor data might be unavailable. While the classifier may be trained with and without the missing data, another approach may be to train additional classifiers with different subsets of data types. For example, imagine the system has breathing and heart rate variability data. One classifier may be trained with both types of data to provide better classification accuracy. But consider what happens if one type of data becomes unavailable. For example, heart rate variability data becomes unavailable due to noise, filtering, sensor disconnection, sensor failure, or even power failure if the heart rate sensor runs on a different power source from the breathing sensor.

If the system has an additional classifier trained without HRV data, it can switch to this alternative implementation and continue running with a slightly reduced classification accuracy without disrupting the overall output of the system. This approach of switching classifiers based on sensor availability applies to all sensors, not just heart rate and breathing.

In some embodiments, the switching between sensors can be for sensors of the same type of data but different sensor implementation. For example, the system may switch between an ECG-based HRV monitor to a PPG based HRV monitor if both sensors are part of the system yet one of them becomes temporarily unavailable. In this case, the system may have some combination of classifiers for PPG HRV, ECG HRV, breathing+PPG HRV, breathing+ECG HRV, breathing. This allows the system to switch between any number of sensor combinations. This is just intended to be an example and does not exclude other types of sensors that provide the same types of data. For example, the system can switch between non-contact and contact sensors in a similar manner.

In some embodiments, the sensor that becomes unavailable is input from a computing device, which may include applications being used, number of task switches, and input device activity as described in the Event Marking section. The system may use a combination of computing device and physiological data while at the computing device, then switch to just physiological data when away from the computing device. An alternative version of this notion is discussed further under the section Optimization—Event-Marking Driven Activation.

Classifying—Power Management

Classifiers have a tradeoff of specificity and sensitivity, or the number of correct classifications versus false positives and false negatives. In some embodiments, the system has a lower quality that acts as a "first pass" classifier. This classifier may be used because the classifier itself is less computationally expensive, the underlying sensor requires less power, or processing the sensor data is less expensive in terms of computation, bandwidth, power, or storage. For example, processing breathing data may be less computationally intensive than HRV data because breathing rate is slower and therefore fewer samples need to be processed for a given time period.

In another example, a classifier may be less expensive because of the entire pipeline leading up to it produces different annotations and features. For example, the features for HRV may include frequency domain analysis that may or may not be included for breathing. By processing a type of sensor with a less expensive processing pipeline, the cost of the entire system may improve.

In some embodiments, the system can have an initial unknown classification state, during which it relies on the higher power classifier. Once an initial classification is made, the system switches to the lower power classifier until a possible change in classification is detected, at which point the higher power classifier is again activated to confirm the change.

Classifying—Latency and Performance

As discussed in section of processing sensor data, windowed data needs a number of data points. While the windows can be leading, trailing, or pivoting (or switching between the three or using a combination of the three), with each having tradeoffs, the latency of windowing has not been discussed yet. When batch processing the data after it has already been collected some time earlier, latency is a non-factor. But when processing the data in near real-time, e.g. processing each RR interval or breath interval as it occurs, latency may matter a lot. In situations where the classifier needs to produce results as quickly as possible, the system might use smaller windows to offer lower latency.

In some embodiments, there is a smaller window (lower latency) and a larger window (higher latency) classifier. The system can switch between them based on processing needs. For example, when the system starts up it might use the lower latency classifier so that results can be delivered more quickly and then switches to the larger window once the window can be filled. In some embodiments, a smaller window (and lower latency) window classifier is used for real-time processing and a larger window (and higher latency) window classifier is used for batch processing. In some embodiments, this switching happens invisibly to the user such that real-time data is corrected as more data is collected.

In other situations where the classifier needs to optimize computational resources, the system might perform a set of lower accuracy but more efficient computations for one classifier, and switch to a higher quality but less efficient set of computations with a different classifier. As a specific example, frequency domain analysis can be done with FFT which may be faster or Lomb-Scargle which may be slower but can better handle certain scenarios (such as ectopic heart beats) better.

In some embodiments, lower quality processing happens for real-time results and higher quality processing happens for batch results. In other embodiments, the system performs lower quality processing unless the classification is ambiguous or low quality, and then the system switches to higher quality classification. Yet in other embodiments, the switch occurs based on whether a particular algorithm will perform better given artifacts or other factors in the data itself. Yet in other embodiments, the algorithms used switch based on the power source of the device doing the processing. For example, if the processing is happening inside a mobile phone, wearable device, or laptop, it might opt for more efficient computations while on battery power and switching to less efficient but more accurate computations when connected to a power source.

Classifying—Data Set Size Management

The amount of sensor data may be large. Large data sets can improve training of a classifier but can slow down performance during subsequent classification. In some embodiments, more data is processed during training and less data is processed during classification. During training, data may be processed at every sample or at regular time intervals. During classification, a variable number of samples may be skipped, or a variable amount of time may be skipped to reduce time spent on overlapping data.

Figure 15:
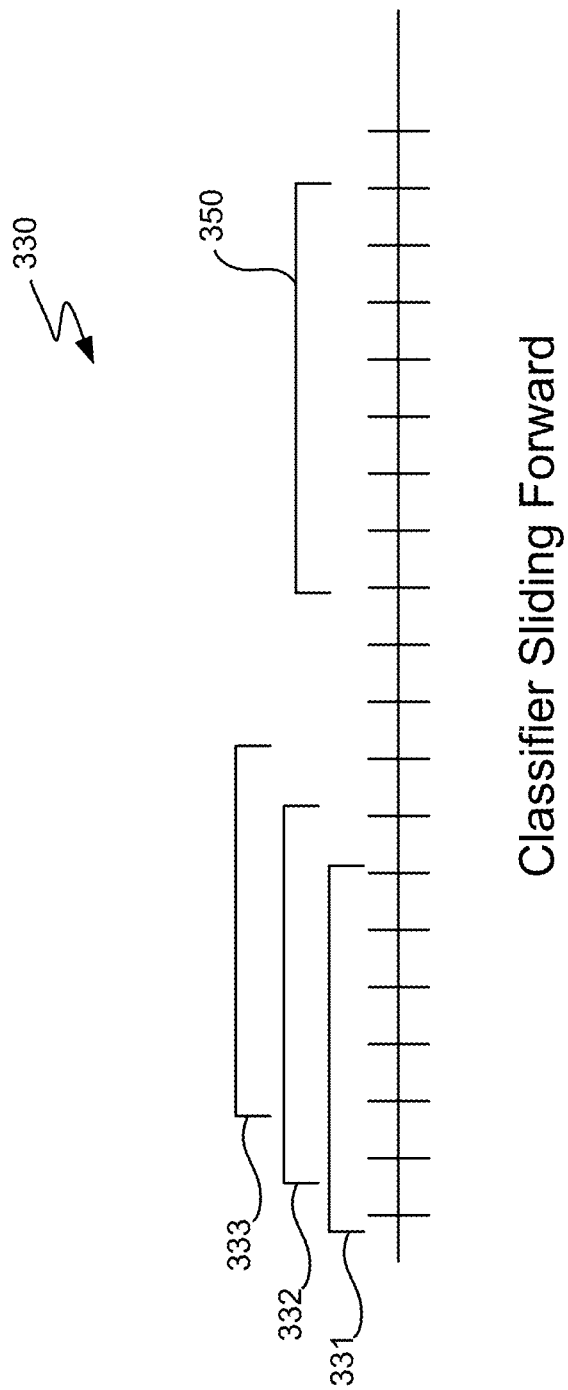
FIG. 15 shows an example of the classifier sliding forward one sample at a time with windows.

To visualize this, look at FIG. 15. Windows 331 and 332 and windows 332 and 333 contain the most overlap. During training, all windows may be used. During classification, the system may opt to look only at windows 331 and 333 or the system may skip more windows based on the desired degree of overlap between windows. In some embodiments, the overlap is considered in terms of the percentage of overlapping samples while in other embodiments the overlap is considered in terms of percentage of overlapping time.

FIG. 15 shows an example of the classifier sliding forward one sample at a time with windows 331, 332, and 333.

Classifying—Mismatch Between Event Occurrence Rates

Some data reported by sensors (or their annotations) may occur at different rates. For example, heart beats generally occur more quickly than breaths. Resting heart rate may be in ballpark of 70 beats per minute, while resting respiratory rate may be in the ballpark of 18 breaths per minute.

Figure 16:
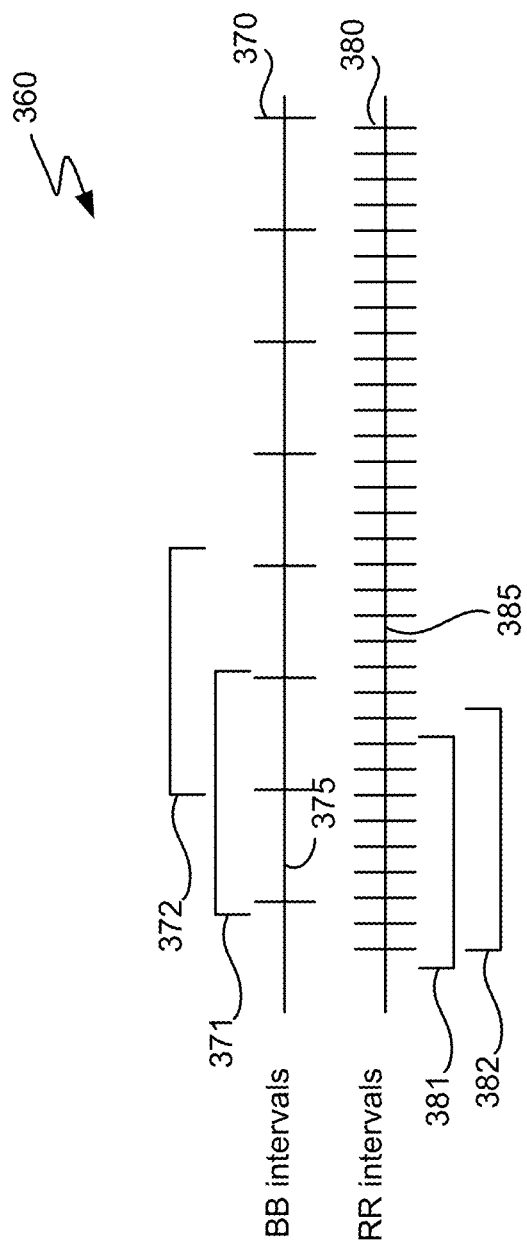
FIG. 16 illustrates a comparison of different event intervals (breath to breath) and (heart time between peaks).

FIG. 16 illustrates a comparison 360 of different event intervals 370 (breath to breath), 380 (heart time between peaks). Note how windows 381 and 382 for RR intervals both contain the same breath interval 375. Meanwhile windows 371 and 372 for breath-to-breath intervals each contain a very different subset of RR intervals.

In some embodiments, a single classifier is used to look at multiple types of data at different occurrence rates. If data is classified at the highest frequency event, then lower frequency events will be "repeated" which might cause the classifier to implicitly give them higher weighting. If data is classified at the lowest frequency event, then some data is left unanalyzed. In other embodiments, a different classifier is used for each type of data which allows each to classify at its own occurrence rate. The outputs of these two classifiers can then be provided as inputs to a different classifier. In other embodiments, the data is normalized so that it becomes more comparable before being classified. One example of such normalization is to resample the events to the same frequency.

Classifying—Data Set Division

To train a classifier, it needs a corpus of data where some data is used for training and some data is withheld for validation and testing. How the data is divided can affect the classification process. A tabular classifier might consider each input row of data to be independent, when in fact certain rows may be highly correlated due to how the windows were generated. As depicted in FIG. 15, windows 331 and 332 and windows 332 and 333 have more correlation than windows 331 and 333. A window without any correlation would have no overlap, such as window 331 and perhaps window 350.

During the training phase, data sets may be segmented such that highly overlapping windows are kept within the same set. For example, window 331 and 332 may both be in the training set. Putting window 331 in the training set and window 332 in the validation or testing set may cause the classifier to learn the wrong correlations because the window overlap is high and thus overfitting the classifier. Given that windows represent a span of time, the data sets can be divided based a threshold of maximum overlap between windows. Physiological data may have daily variations. Some embodiments also specifically ensure that data is divided in a way that creates training and testing data from each day. Other embodiments may further ensure that training and testing data is randomized across different parts of the day to avoid degenerate cases such as using mornings for training and afternoons for testing.

Classifying—Label Frequency Normalization

While the system uses event markers to generate classifications, some events can be more frequent than others. To ensure the system does not encode these original frequencies in its model, the frequency of the event marker labels can be normalized. This can be done by repeating infrequent labels, sampling frequent labels, or a combination of the two.

Predicting

Although changes in mental state may occur at any time, the probability can vary. In some embodiments, the system may predict when different mental states are more likely. In some embodiments, the system may predict when different mental states are less likely.

In some embodiments, these predictions may be based on historical data such as times of day when the user had past different mental states. In other embodiments, predictions may also be based on locations where the user had past mental states. In other embodiments, predictions may be based on activities where the user had past mental states. For example, the system may detect the current application the individual is using on a computing device to determine whether the individual is doing something unproductive and unchallenging like Facebook or doing something challenging like using a software development environment, word processing application, or another application like a game.

In some embodiments, the predictions rely on physiological or other data about the individual. In some embodiments, this may include the duration, quality, and breakdown of sleep from the night before. In other embodiments, the system estimates a running "sleep debt" over a recent time period. In other embodiments, sleep duration, quality, and breakdown are compared to historical patterns of the user. In other embodiments, "jetlag" or shifts in sleep schedule are considered and used to reduce the predicted likelihood that the user will experience flow based on the delta of the shift and number of days since the shift. Each delta of about 1 hour will have a 1 day influence. For example, if the user shifts 8 hours, then the system predicts flow will be less likely for the next 8 days. If the user shifts 1 hour, as might be typical of sleeping in on weekends and waking up earlier on weekdays, then the system might flag Saturday and Monday as having a lower likelihood of flow.

In some embodiments, prediction is based on the amount of physical activity the individual has experienced recently. In some embodiments, the prediction is based on the amount of physical activity compared to the individual's usual level of physical activity. In some embodiments, the prediction is based on physical exercise immediately before returning to the system, as physical activity can reduce mental stress or lead to an altered state of attention that makes entering flow easier.

In some embodiments, the system predicts flow based on the amount of flow the individual experienced during a different or prior detected flow inducing activity, as flow within a given time period such as a day can be finite. In some embodiments, the system predicts mental state based on the amount of meditation the individual has recently performed. In some embodiments, the system predicts mental state based on the light exposure the user has received. In some embodiments, the system predicts mental state based on the difficulty of the task the user is about to perform.

In some embodiments, the system predicts flow is unlikely based on the amount of alcohol the individual has recently consumed. In some embodiments, this is measured by peak BAC. In other embodiments, this is measured by total duration at which BAC remains elevated, which may more accurately capture total units of alcohol consumed over a longer period of time. If the individual is experiencing a hangover, then flow is unlikely.

In some embodiments, the system predicts flow is unlikely based on whether the user may be having an immune response, as determined by one or more of fever, changes in resting heart rate, changes in heart rate variability, changes in sleep, self-report, or automated collection of medical records which may identify recent illness or dosing with a vaccine.

In some embodiments, the system relies on self-reported information from the user for predictions. A survey of the individual on level of stress may be used in predicting flow for the day. In another embodiment the system surveys the individual on how well rested the individual feels.

Predicting—Using Predictions

By having predictions with high probabilities, the system can treat this as having a priori knowledge of when different mental states will or will not occur. These predictions may be used for a number of purposes. In some embodiments, predictions improve the accuracy of detecting a specific mental state experience or lack of a specific mental state.

In some embodiments, predictions alter the sensitivity of determining whether the individual is experiencing a specific mental state. For example, if flow is very likely, the system may be more eager to detect the individual is in flow. If flow is very unlikely, the system may be less eager to detect the individual is in flow. This effectively is a way of adapting the hysteresis thresholds described previously (see Hysteresis section).

In some embodiments, there are multiple mechanisms to detect mental states. In some embodiments, predictions completely alter the mechanism under which mental state is detected. For example, suppose the system has one mechanism (a) to detect a specific mental state and another (b) to detect lack of that mental state. Without a prediction, the system may use (a) to detect the specific mental state. With a prediction for high likelihood of the specific mental state, the system may invert and use (b) to detect the lack of the specific mental state. In other embodiments, there are more than two mechanisms and predictions allow the system to switch between them based on predictions. For example, the system may have multiple mechanisms for detecting a specific mental state and predictions cause the system to switch between these different mechanisms. In some embodiments, predictions reduce the number of sensors or types of data needed for detecting different mental states.

Predicting—Prediction of Pre-State

In some embodiments, predictions improve the speed of detecting mental states. In some embodiments, predictions may be used to determine a pre-state. Some mental states may not necessarily be entered instantaneously, so there may be a transition period. In some embodiments, the system predicts that a specific mental state is likely and enters a pre-state. In some embodiments, the mechanism used to detect a specific mental state changes when in the pre-state. In some embodiments, the system uses a timer to hold the pre-state. If the user does not enter the predicted state, the system may re-evaluate its predictions and decide the user is not in the predicted state or restart the pre-state timer to start the process again.

In some embodiments, the system predicts when the user is likely to return to a state when a state is interrupted briefly. For example, the user may get up to use the bathroom and want to immediately return to working and re-enter flow.

Mediating

The mediating component of the system may be embedded within other parts of the system but is discussed here for the sake of conceptually simplifying the description of the system. Mediation facilitates inter-component communication and helps provide feedback loops.

Mediating—Sensor Switching

In some embodiments, inferred sensors may be lower power because they "piggyback" on another sensor that is already running. The system may opt to use the inferred sensor(s) until a change in classifier state. In some embodiments, switching between sensors is done with a "mixed mode" approach where the sensor is selected based on criteria such as power usage, accuracy, and battery level of the sensor. In other embodiments, results of multiple indirect sensors are combined to generate a more accurate measurement without relying on a direct measurement. This combination may rely on aggregation functions like averaging or consensus if more than one sensor is available.

Mediating—Circadian Rhythm Influences

As discussed in predicting, the system may track sleep to assist in predicting the ability for the user to enter different mental states.

Mediating—Tracking

Some embodiments use a change in spontaneous eye blink rate, which increases in the evening in correlation with the wake maintenance zone of the circadian rhythm. By identifying the wake maintenance zone, the system can then extrapolate other points in the circadian rhythm. In addition, the system can identify when the user may be fatigued. Some embodiments use a decrease in RSA to identify fatigue, as RSA decreases when individuals are drowsy.

Mediating—Baselining

Some embodiments track respiratory rate and heart rate variability during different stages of sleep. One reason that sleep is interesting to the system is that it allows the system to attempt to automatically identify a baseline for the user, without input from the user or special behavior from the user (such as sitting still for 5 minutes). Sleep is a consistent period of quiescence where external influences like user movement are minimized. In some embodiments, the system generates baseline metrics for the user while the user is asleep. These metrics can be used for computing absolute features. In addition, some embodiments may compute baseline metrics that are used for future generation of offset features as described in the Processing—Annotating section.

Some embodiments generate baseline metrics based on phase of sleep, while others may also consider how long the user has been asleep. For example, slow wave sleep—colloquially known as "deep sleep"—is one such stage when baseline metrics can be collected. Some embodiments collect these within the first few hours of sleep, as they will be closer to waking values because heart rate reaches its minimum later in the night.

Although HRV and RSA are expected to be relatively stable between individuals, certain external factors such as illness, drugs (like opioids), alcohol, excessive exercise (overtraining), and medical conditions can influence these negatively. Many of these influences can be captured when performing Profiling. Some of these influences can also be detected automatically, based on changes seen over time. These changes are easiest to detect once the user is established with the system, because a baseline is already known for the user and therefore anomalies are easier to detect. To prevent anomalies occurring during initial setup of the system from negatively impacting the baseline, the system can track several night's worth of sleep before attempting to determine a baseline.

After the baseline is created, the system also re-evaluates the baseline on a regular basis. If one or more night's worth of data appears to be an outlier, that night is flagged as an outlier and excluded from the aggregation of data used to create a baseline for the user. In some embodiments, the system creates both regular and outlier baselines so that the system can better track user mental states when outlier events occur. In some embodiments, a provisional baseline is generated from the first night of sleep, but subsequent data based on that baseline can be re-processed once a non-provisional baseline is developed. The benefit is that the user can start receiving feedback from the system sooner. Some embodiments use sleeping measures of heart rate variability and breathing as part of profiling for the user, in order to estimate the user's affective style.

Mediating—Optimization—Activity-Driven Deactivation

In some embodiments, one sensor can cause another sensor to deactivate. For example, an accelerometer may detect the user is moving and therefore deactivate tracking of breathing or heart rate. While measuring such data can be important for fitness and athletic training, the purpose of this system is tracking changes in mental state. When the user is moving significantly or exercising, that will dominate the physiological signals such that mental state classification will be difficult. Therefore, the system can turn sensors off to save power, unless the user wants to track calories burned or other workout related metrics. This is a variation of the power management techniques discussed previously in PPG power optimization. In some embodiments, the system stops attempting to classify mental state for a period after exercise. In some embodiments, the system uses a different classifier or set of relative offsets after exercise to account for changes in physiological metrics. In some embodiments, these offsets have a decaying adjustment before returning to the standard baseline offsets for the user.

Optimization—Event-Marking Driven Activation

In some embodiments, sensors are switched off until they are needed. Collection of heart rate, breathing, electrodermal activity, eye tracking, or other sensor data can be disabled until the user is engaged in an activity that can be tracked through event marking. For example, consider a user starts interacting with a computing device. The sensors may be turned off while the computing device is idle. The computing device may be considered idle when it is:

Powered off.

In low power mode.

After a period of no interaction with the computing device as determined by lack of input by keyboard, mouse, voice, pen, game controller, or other input.

When the user's attention is no longer on the computing device, which may be determined by another computing device detecting the user's attention (e.g. the user switches from a desktop PC to a smartphone or tablet), or may be detected using gaze detection to see the user is no longer looking at the computing device.

When the user moves away from the computing device, which may be determined by ultrasonic or infrared proximity sensors in the computing device, location detection technology embedded in a wearable device that the user has, or a wireless signal from a device the user has (e.g. Bluetooth Low Energy or Wi-Fi from a wearable or phone).

Optimization—Power Source Considerations

Different sensors may have different sized batteries, different battery levels, different amounts of power usage, or different power sources. For example, imagine a non-contact sensor, such as radar, camera, or RF sensor, is connected to a power source and does not rely on a battery. Meanwhile, the user has another type of sensor embedded in a wearable device. In some embodiments, the system may opt to use the wall-powered device and only activate the wearable device when the wall powered device is unavailable or when the wearable device is needed for disambiguation.

Example Implementation of the System

The following describes one example implementation of the system, although other implementations may exist.

Figure 18:
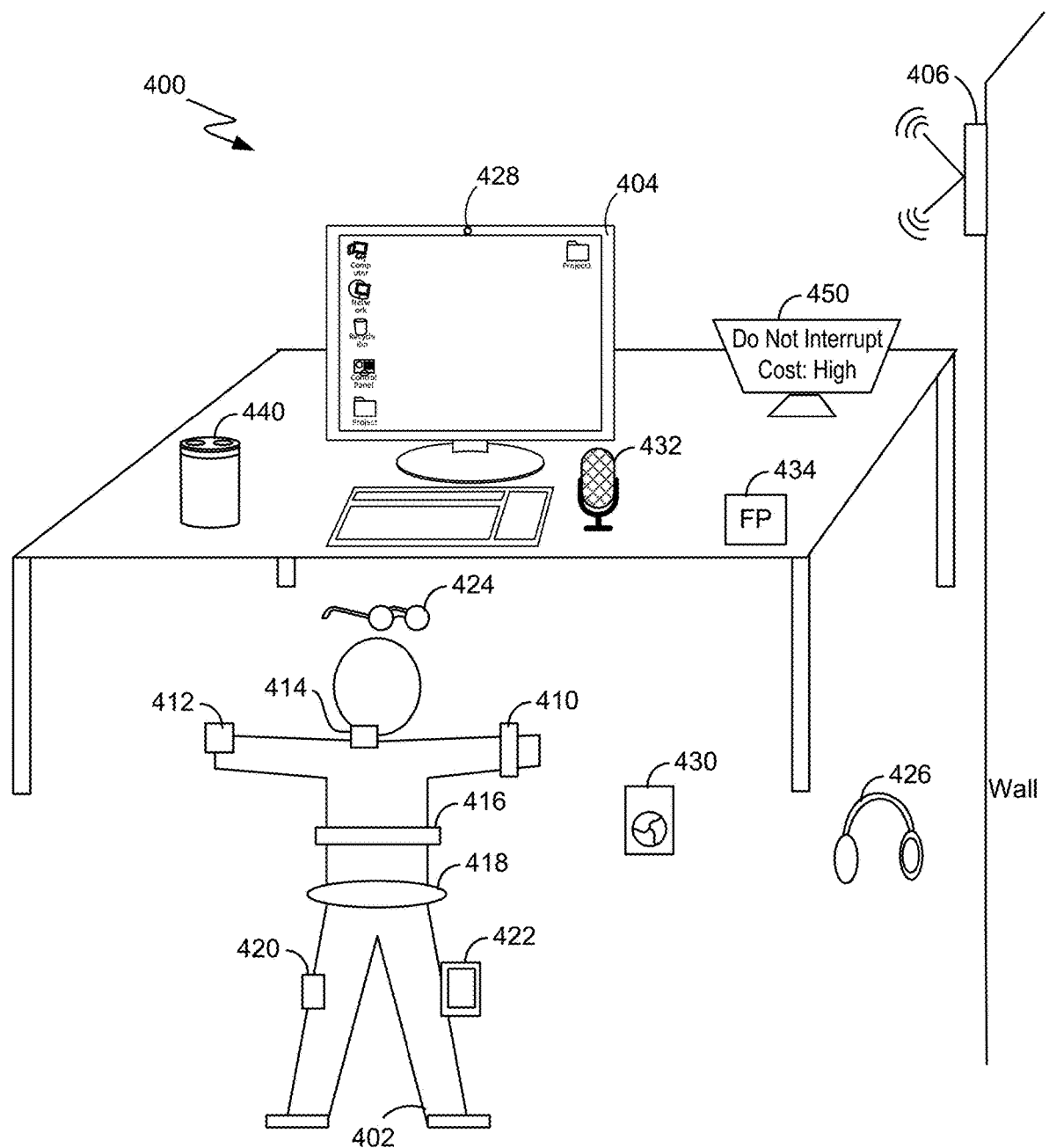
FIG. 18 illustrates an example computing system arranged to implement the system and methods of the present invention.

FIG. 18 illustrates an example computing system arranged to implement the system and methods of the present invention. Shown is a user 402 using any suitable computing device 404 upon a table (for example). Upon a wall, ceiling, etc. is a wireless access point number 406 providing a connection to the Internet although the computer may be using a wired connection as well. It is also possible to integrate any sensor into the access point as well. Computing device 404 may be a desktop computer, laptop computer, tablet, mobile device (e.g., telephone), an IOT device (having a CPU, storage, etc.), etc.

Any number of sensors may be located upon the user's body and may include or be embodied within a wearable device 410, such as a smartwatch (including HR, HRV, PPG, skin, pulse, EDA, temperature, accelerometer, gyroscope, barometer, GPS, etc. sensors), a pulse oximeter 412, a sensor 414 to measure heart rate or heart rate variability, a movement sensor 416 that may include an accelerometer, gyroscope or barometer, a strain gauge sensor 418 to measure movement about the thorax or abdomen, an NFC tag 420 that the user may carry in a pocket or elsewhere, a mobile telephone or smartphone 422 which may also include an accelerometer, gyroscope, barometer, satellite navigation, Wi-Fi, Bluetooth, step counter, etc., glasses 424 that may contain sensors to monitor the user's eyes such as electrooculography camera as well as sensors such as accelerometer or gyroscope, and a headset 426 with sensors to measure one or more of brain waves, fNIRS, skin temperature, pulse, eye movement, etc. A body camera 430 may be worn by the user to track images on a screen of the computing device 404 (shown to side for clarity). A RIP sensor is a respiratory inductance plethysmography sensor.

Any of a number of other sensors may also be contactless in that they are not required to be in contact with the user's body nor carried by the user, and these include a camera 428 incorporated into or connected to the computer 404, a microphone 432 integrated with the computer or standalone, a fingerprint sensor 434, and an integrated device 440 containing any number of cameras and other sensors. For example, integrated device 440 may contain a traditional camera for monitoring the user's motions, face, eyes, skin, breathing, subject identification, etc., a telephoto camera for a better view of the face or eyes including the pupils, infrared camera for monitoring skin temperature, radar/electromagnetic wave detector used for subject identification or monitoring the lungs or heart, or environmental sensors to detect air temperature, carbon dioxide levels, or ambient light levels. Any of these individual sensors within integrated device 440 may also be standalone devices located in close proximity to the user but not required to be carried by the user or in contact with the user.

These sensors are described in detail above and collect physiological and environmental data for use by the system.

The system software is broken into two main parts: training and classifying.

Training

Given a dataset of sensor data, the training system processes data through three phases of:

1. Ingestion—The dataset, which includes both sensor data and event markers, is read.
2. Extraction—Features are computed from the dataset and event markers are combined with the dataset.
3. Machine learning—Data is split into train and test groups, and then a machine learning model is trained using the data from phases 1 and 2.

Training—Representations

As data flows through the processing stages, it is transformed between three different representations:

1. Dataset—Data is ingested from raw input data format. CSV is one example format, although other formats are also possible including streaming sensor data and event marker data directly from their sources.
2. Model—In-memory objects provide strong types to represent different kinds of data.
3. Database—The database closely represents the model representation, although there are some differences from the models due to "impedance mismatch." The database makes it easier for the machine learning stage to query different sections of the data at a time, without loading all of it into memory. This is important because datasets can be large, potentially exceeding the amount of RAM available.

Training—Dataset

Data collected, as described in the Sensing Generally and Event Marking sections, can be collected into a dataset. Such a dataset may be stored as a collection of files or may be represented as a collection of streams of input data. A collection of files is especially useful for initial training of the system, as well as for batch processing. A stream of input data is especially useful for real-time classification after the system has been initially trained.

If represented as a collection of files, these files may be imagined to be in a hierarchal structure such as the following:

- subjects/—A directory containing data for all subjects.
  - subject/—One directory per subject, where the folder name does not matter but a convention can use the subject's anonymous UUID. Each subject directory may contain:
    - subject_info.json—A JSON file describing static info about the subject, such as subject ID, year of birth, and sex.
    - event_marker/—Contains any number of directories with event marker data, as collected by an event marking component as described in Event Marking. The names of the subdirectories do not matter. Each subdirectory should contain the CSV files exported by the event marking software. Often there will only be one subdirectory, although the support for multiple allows for multiple datasets to be combined.
    - hexoskin/—Contains any number of directories with Hexoskin output data. The names of the subdirectories do not matter. Each subdirectory must contain one 'info.json' plus CSV files for each data type.
    - healthkit/—Contains CSV files for data that has been exported from HealthKit.
    - zephyr/—Contains any number of directories with Zephyr output data. The names of the subdirectories do not matter. Each subdirectory must contain one 'info.json' plus CSV files for each data type.
    - label/—Contains any number of directories with label data. The names of the subdirectories do not matter. Each subdirectory must contain a 'label.csv' file with labels. This provides a way of implementing arbitrary event markers that might be generated manually.

Of course, this is just an example. The hierarchy described above is arbitrary and the folders may use different names. Likewise, CSV (comma separated values) may be replaced with other formats such as tab separated values, binary formats such as WAV or WFDB, or other formats. The input files may be individually compressed in formats such as GZIP or the entire directory may be compressed.

Additional sources of data can also be included, such as:
- Video to process for data such as face landmarks, respiration, and HRV data
- Respiratory waveforms or peak timings from other sources, such as radar, radio, or other devices
- ECG, RR intervals, or HRV data from other sources such as radio, PPG, or other devices
- Temperature from other sources, such as infrared cameras or wearable devices
- Electrodermal activity from other sources such as wearable devices
- Sleep data Training—Ingestion During ingestion, raw sensor input data from a dataset is parsed into more strongly typed object representations. The benefit of this design is that the ingestion phase has deeper knowledge about the specific data sources which is then abstracted by the strongly typed object representations.

Some algorithms may be applied at this stage, especially to reduce the volume of data. For example, ECG and respiratory waveforms can go through peak detection to identify timing intervals between peaks. Respiratory waveforms may also have valleys detected as well. This is still a very raw form of data, but it reduces the volume of data up to three orders of magnitude. This was discussed previously in the section Sensing—Capture vs. Algorithmic Interpretation. Other algorithms may also be applied at this stage, such as RR interval detrending or separation of respiratory influences from the original RR interval series. If such algorithms are applied, a separate table is stored containing these modified RR intervals separate from the original RR intervals. During ingestion, data flows from Dataset→Model→Database.

Training—Extraction

During extraction, the system iterates through the event markers and labels that were loaded during the ingestion phase. For each marker, the system has start and end timestamps. The system can then load the sensor data from those timestamps and apply a variety of algorithms to generate features that may be salient to the machine learning model. Various statistical and other derived metrics are created, as described in the Processing section. As an example, a sequence of inhale/exhale intervals may generate several features such as basic statistics like min, mean, max, and standard deviation. A more unusual feature might include identifying sighs, which are reoccurring deeper breaths that re-inflate the alveoli in the lungs.

Although the extraction phase aids machine learning, the primary difference is between this extraction phase and the machine learning phase is that the extraction stage relies on well-defined algorithms with consistent behavior. These algorithms can generate absolute, relative, and offset metrics. The example below includes mostly absolute metrics, with a few relative metrics such as br_sigh_percentage. However, the extraction phase has the ability to generate relative and offset metrics, as it has access to the dataset including information such as values from the prior night's sleep.

At the end of extraction, data is merged together into a "wide" object with many fields. These merged objects are written into the database for later querying by the machine learning stage of the processing pipeline. Multiple types of extracted data can be generated based on the event markers and labels that were ingested, and these are associated with tags. For example, extraction may be performed on event markers for application usage, event markers for task switches, event markers for game-playing tasks, etc. For event markers around task switches, the system may load pivoting windows of data for a small time duration around task switches, as well as pivoting windows during a task. These can be associated with labels for "switch" and "non-switch." During extraction, data primarily flows from Database→Model→Database.

An example of a "wide" row of mostly absolute data with labels for app switches in CSV might look like the following:

timestamp, owner_id, day_of_week, is_weekend, label_start, label_end, label_duration_seconds, label_semantic_duration, label_semantic_progress, rr_confidence, rr_ori ginal_min, rr_original_max, rr_original_average, rr_original_standard_deviation, rr_original_coefficient_of_variation, rr_original_sd1, rr_original_sd2, rr_original_sd1 sd2, rr_original_pnn20, rr_original_pnn50, rr_original_lf_peak, rr_original_lf_abs_power, rr_original_lf_power_percentage, rr_original_lf_norm_power, rr_original_hf_peak, rr_original_hf_abs_power, rr_original_hf_power_percentage, rr_original_hf_norm_power, rr_original_lf_to_hf_ratio, rr_original_adaptive_freq_lf_peak, rr_original_adaptive_freq_lf_abs_power, rr_original_adaptive_freq_lf_power_percentage, rr_original_adaptive_freq_lf_norm_power, rr_original_adaptive_freq_hf_peak, rr_original_adaptive_freq_hf_abs_power, rr_original_adaptive_freq_hf_power_percentage, rr_original_adaptive_freq_hf_norm_power, rr_original_adaptive_freq_lf_to_hf_ratio, rr_separated_min, rr_separated_max, rr_separated_average, rr_separated_standard_deviation, rr_separated_coefficient_of_variation, rr_separated_sd1, rr_separated_sd2, rr_separated_sd1 sd2, rr_separated_pnn20, rr_separated_pnn50, rr_separated_lf_peak, rr_separated_lf_abs_power, rr_separated_lf_power_percentage, rr_separated_lf_norm_power, rr_separated_hf_peak, rr_separated_hf_abs_power, rr_separated_hf_power_percentage, rr_separated_hf_norm_power, rr_separated_lf_to_hf_ratio, br_breath_type, br_half_interval_millis, br_full_interval_millis, br_min, br_max, br_average, br_standard_deviation, br_coefficient_of_variation, br_sigh_count, br_sigh_percentage, activity_min, activity_max, activity_average, activity_standard_deviation, activity_coefficient_of_variation, keyboard_inputs_per_second, mouse_inputs_per_second, total_inputs_per_second, awake_duration_seconds, sleep_duration_seconds 2021-03-30T07:11:54.226769367Z,4d178315-4292-4476-b67b-afa8496ea458,1,false,2021-03-30T07:11:39.226769367Z,2021-03-30T07:12:09.226769367Z,30.0,0,1,switch,717,HIGH,420,1014,735.9445449844881,97.00368 274828372,0.131808413296043,84.07515408007873,123.6329776664174,0.6800382524711 786,86.51269013659672,67.63045632783212,0.055511474609375,2213.196857413204,33.0 3861303487479,38.806547635592246,0.1632080078125,3489.956327446053,52.098084372 78826,61.193452364407754,0.6341617630020085,0.055511474609375,3539.786258098057 3,60.21313159967707,72.49062049721866,0.256622314453125,1343.3092842195488,22.85 0209818385895,27.509379502781343,2.635123794409448,420,1014,735.9445449844881,97 0.00368274828372,0.131808413296043,84.07515408007873,123.6329776664174,0.68003825 24711786,86.51269013659672,67.63045632783212,0.055511474609375,2213.19685741320 4,33.03861303487479,38.806547635592246,0.1632080078125,3489.956327446053,52.0980 8437278826,61.193452364407754,0.6341617630020085,Inspiration,2070,3140,2617,4406, 33 86.0,512.2377377741707,0.15128108026407877,0, 0.0,0.0,0.109375,0.010026041666666667, 0.02516286133852306,2.5097503257124294, 0.5333333333333333,0.5666666666666667,1.1,null,null Another example with labels for mental state looks like the following:

timestamp, day_of_week, is_weekend, label_start, label_end, label_duration_seconds, label_semantic_duration, label_semantic_progress, label, rr_interval_millis, rr_confidence, rr_original_min, rr_original_max, rr_original_average, rr_original_standard_deviation, rr_original_coefficient_of_variation, rr_original_sd1, rr_original_sd2, rr_original_sd1sd2, rr_original_pnn20, rr_original_pnn50, rr_original_lf_peak, rr_original_lf_abs_power, rr_original_lf_power_percentage, rr_original_lf_norm_power, rr_original_hf_peak, rr_original_hf_abs_power, rr_original_hf_power_percentage, rr_original_hf_norm_power, rr_original_lf_to_hf_ratio, rr_original_adaptive_freq_lf_peak, rr_original_adaptive_freq_lf_abs_power, rr_original_adaptive_freq_lf_power_percentage, rr_original_adaptive_freq_lf_norm_power, rr_original_adaptive_freq_hf_peak, rr_original_adaptive_freq_hf_abs_power, rr_original_adaptive_freq_hf_power_percentage, rr_original_adaptive_freq_hf_norm_power, rr_original_adaptive_freq_lf_to_hf_ratio, rr_separated_min, rr_separated_max, rr_separated_average, rr_separated_standard_deviation, rr_separated_coefficient_of_variation, rr_separated_sd1, rr_separated_sd2, rr_separated_sd1sd2, rr_separated_pnn20, rr_separated_pnn50, rr_separated_lf_peak, rr_separated_lf_abs_powerxr_separated_lf_power_percentage, rr_separated_lf_norm_power, rr_separated_hf_peak, rr_separated_hf_abs_power, rr_separated_hf_power_percentage, rr_separated_hf_norm_power, rr_separated_lf_to_hf_ratio, br_breath_type, br_half_interval_millis, br_full_interval_millis, br_min, br_max, br_average, br_standard_deviation, br_coefficient_of_variation, br_sigh_count, br_sigh_percentage, activity_min, activity_max, activity_average, activity_standard_deviation, activity_coefficient_of_variation, keyboard_inp uts_per_second, mouse_inputs_per_second, total_inputs_per_second, awake_duration_seconds, sleep_duration_seconds 2020-12-18T10:45:00Z,null,null,2020-12-18T10:44:00Z, 2020-12-18T11:12:00Z, 1680.0,2,0,flow,687,HIGH,628, 722,673.5909090909091,20.793914787206134, 0.03087024261546224,11.136572893576977, 28.333057661470338,0.3930593381991884,20 0.930232558139537,0.0,0.0625,164.7896405200539, 41.17401191712419,52.44673425514637 4,0.15625, 149.41417571447892,37.33232885295714, 47.55326574485362,1.1029049936664 412,0.0625, 288.11511709595,72.72698986839126, 92.89950479006183,0.28125,22.0212154 35686784, 5.558669493025941,7.100495209938171, 13.08352474627904,584,979,664.19512 19512196, 67.0845635339024,0.10100128910436244, 41.04116286340249,90.324353329975 24,0.45437538548955747,9.836065573770492, 50.737704918032787,0.046875,1101.9983845 559304, 27.216079231958094,84.7752445600262,0.171875, 197.90749041402782,4.8877258 03587868, 15.224755439973807,5.568250005346034,Inspiration, 1476,2078,2078,5414,3252.7,1146.8860303738409, 0.35259508419892427,0,0.0,0.0,0.015625, 0.0010416666666666667, 0.003964189557850976, 3.8056219755369374,0.0,0.0,0.0,null,null Training—Machine Learning The machine learning layer of the system queries the database for the merged output data from the Extraction phase. Queries are done on a per-tag basis, as each tag represents different types of incomparable data.

As data is loaded for training, it goes through several steps:
1. Construct a Data Interface. A Data Interface provides data-specific implementation details, such as column selection, filtering, and label mapping. Column selection and filtering can opt to use only a subset of fields in the data, as a way of creating a simpler model. Label mapping can convert event markers into different formats or merge them together. For example, labels for applications like Android Studio, IntelliJ, Xcode may be mapped to "IDE."
2. Designate slices for later querying into the data interface. Because the data is represented as a time series, slices are often generated based on time.
3. Optionally normalize the frequency of labels. This can be done by repeating infrequent labels, sampling frequent labels, or a combination of the two. This ensures that label frequencies do not dominate the model's classifications.
4. Split those slices into disjoint training and testing data.
5. Normalize all data to arrays of floating point values ranging from 0 to 1.
6. Convert labels to one hot encoding.
7. Construct one or more models with different parameters.
8. Train model with labeled data.
9. Test model for accuracy.
10. Select the best model.

During machine learning, data primarily flows from Database→Model. The Model is a machine learning model that can be used to subsequently make classifications. The training process can generate multiple classifiers for different types of data, for example the system might consist of one or more classifiers for low or high stress, for low or high attention, for low or high motivation, for low or high arousal, or for low or high valence. Other embodiments may generate a classifier for overload, flow, and underload. Other embodiments generate a classifier for detecting moments of distraction. Other embodiments generate models for effortful, effortless, and default mode attention.

Classifying

The classifying part uses the output of the Training stage to detect changes in mental state. For batch classifications, a dataset can be represented as a collection of files. But for real-time classification, the system needs streams of input data to perform classifications continuously.

Given a dataset, the classifying system processes data through phases of:
1. Ingestion
2. Extraction
3. Classification
4. Post-processing These phases have similarities to their counterparts in the Training part.

Classifying—Ingestion and Extraction

The ingestion phase is similar to the same phase during Training, with a few differences. In particular, the data does not necessarily need to be stored in a database. However, there is a benefit of doing so, as the additional data may be stored for generating a new model in the future.

FIGS. 21A-21E show an example of data representation after database ingestion during classifying. Shown is a database table relationship diagram. A subjects table contains an identifier to identify the subject, along with additional subject-specific details. The identifier is used as a foreign key to a table of sessions. A session represents a single collection of sensor or event marker data. A session may span multiple days, and different data sources may be represented by different sessions (e.g. data from a wearable device and data from event markers on a computing device may be collected at the same time but in different sessions). Each session has a unique identifier that is used as a foreign key to different datatype tables. Different sessions will have different types of data available. A session from a computing device might have data populated in the application and interaction table, for example. A session from a wearable device may have various physiological data such as respiration_interval or rr_interval.

The extraction phase is similar to the same phase during Training, with the exception that event markers or labels may not be available.

FIGS. 22A-22D show an example of data representation after database extraction during classifying. Shown is a database table relationship diagram. A subjects table contains an identifier to identify the subject, along with additional subject-specific details. The identifier is used as a foreign key to a table of labeled_windowed_sample values. labeled_windowed_sample contains the columns for extracted data which is similar to the example CSV row shown previously. Some types of data are generic, such as int_statistics, so these are represented in a different table with a foreign key to simplify the number of columns needed for labeled_windowed_sample. Note that unlike the data represented during ingestion, sessions are not represented here because the merged samples span different sessions.

Classifying—Classification

During the classification phase, the data generated by the extraction phase is passed into one or more classifiers to generate one or more classifications. The classifications are a labeled mental state along with a probability, i.e., the probability is based on the labels used during training. For example, a classifier for task switching might indicate a probability of whether a switch occurred or not. For example, 0% indicates low, probably no switch occurred while 100% indicates probably a switch occurred. In another example, a classifier for stress emits 100% as high probability of stress and 0% as low probability of stress. In another example, a classifier for flow emits 100% as high probably of flow and 0% as low probability of flow. I.e., the output is "flow" along with a probability value; a low value of 0%, 10%, etc. indicates it is unlikely that the user is in "flow," while a high value of 100%, 90%, etc. indicates the user is in "flow." Generally, a value in between 0% and 100% is selected to then choose between one of the two classifications, e.g., in flow or not in flow.

Classifying—Hysteresis

The hysteresis phase takes output of the classification phase, remembering the prior classification to reduce rapidly switching between output states. The hysteresis is a decorator to the classification output, improving the perceived robustness of the system. For example, consider the classification of stress. New data is generated continuously, so classifications may be occurring as frequently as new data arrives or new classifications may be generated after some number of events or some period of time has passed. For the sake of discussion, consider a scenario where new classifications are generated once per second. In some embodiments, the classifications are independent as far as the classifier is concerned, so output of the classifications may vary from one second to the next. (Classifications may have overlap in their input data, as depicted in FIG. 15, although many classifier implementations are stateless).

In some embodiments, the system uses hysteresis to smooth the output and identify "low" and "high" classifications for stress, flow, attention, motivation, valence, or arousal. The hysteresis may be applied in multiple forms. In one embodiment, there are different entry and exit values to switch states. For example, detecting high stress might require a probability of 80% or higher. Exiting the high stress state might require a probability of 60% or lower. These are just examples, demonstrating how the entry and exit criteria for "high" are different. Other percentages are possible. In some embodiments, a weighted average is used. In some embodiments, a refractory period prevents rapid switching even if the hysteresis criteria are met. For example, a certain amount of time must pass after entering a state before it can be exited. In other embodiments, a certain number of samples meeting a probability threshold must be seen within a period of time.

System Detail—Distributed Measurement of Mental State

A distributed method for measuring mental state identifies either very coarse metrics for an individual or more accurate metrics in large groups of people. In such a system, discontinuous sensor data and optionally continuous event markers are collected from a large number of people and analyzed in aggregate. For example, a population of people using a device that collects sensor readings occasionally throughout the day and who also install an event marking application on their computing devices.

At the time of this writing, the Apple Watch implements such a behavior by turning on the PPG and/or blood oxygen sensor for short periods of time such as 1-2 minutes approximately every 10 minutes. The Apple Watch does this to collect some health information, while reducing power usage since the sensor does not run continuously. This data can be processed in a way similar to that described in the prior section, with the limitation that number of samples and number of windows of data is much smaller. Training of the system for a given user may take more days worth of data, since each day will have significantly less data to operate on.

Once trained, the classifications from such a system can provide individual results. For individuals, the data would represent broad metrics with some inaccuracies due to the gaps in the data collected. Such a system would not be sufficient for real-time feedback, nor would it feed into other aspects of the system such as blocking of notifications (covered in a subsequent section), because the responsiveness of the system is limited by the sampling period of the sensor.

In one embodiment, the system can collect such short readings from a large number of users and identify trends over time for a group or organization. Under such an implementation, the system can much more quickly identify shifts in mental state across an organization. For example, an organization may implement a change such as "meeting free Friday" to see what organization-wide shifts in mental state occur.

Modules

Figure 19:
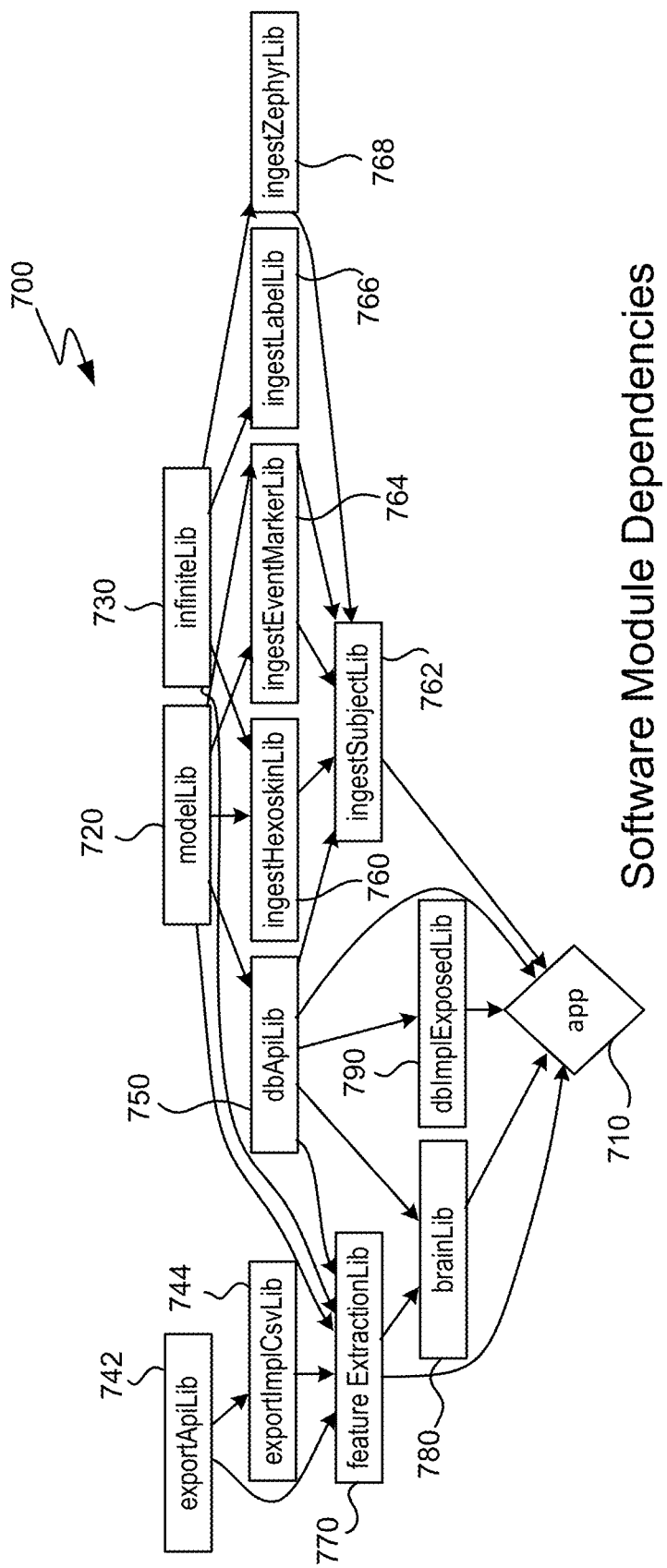
FIG. 19 is a block diagram of the software module dependencies in an example implementation of the system.

FIG. 19 is a block diagram of the software module dependencies in an example implementation of the system.
- Model 720—Provides basic model objects for the data that being processed, including representations of a Subject, Session, and TimeSeries, along with various type-specific representation such as Rrinterval, BreathInterval, IntStatistics, and other data types. This module also contains algorithmic implementations to interpret raw sensor data, as well as generate features from sensor data. These implementations are generic, to avoid being tied to specific sensor brands or implementations where possible.
- db—Implements database objects for reading and writing models to a persistent representation. Using a database allows the machine learning component to query for chunks of data under different time ranges without loading the entire dataset into memory at once.
  - Api 750—Provides interfaces that for insert and query APIs. This API is passed around throughout the application, such that other modules do not need knowledge of the exact database implementation. This allows for swapping different database implementations. The discussion so far has considered a relational database, although the Api would allow for swapping exposed 790 for a different relational or a non-relational database.
  - exposed 790—Implementation of the database using a specific database library.
- ingest—Implements device specific implementations to read sensor data and map into model objects.
  - event_marker 764—Concrete implementation to import event marker data from the event markers generated on a computing device as described in the Event Marking via Computing Device section.
  - hexoskin 760—Concrete implementation to import Hexoskin data.
  - healthkit—Concrete implementation to import data from HealthKit.
  - zephyr 768—Concrete implementation to import Zephyr BioModule data.
  - label 766—Concrete implementation to import arbitrary labels.
  - subject 762—Depends on the other ingestion libs to coordinate ingestion for all the data for a particular subject.
- featureExtraction 770—Implements feature extraction, transforming original ingested input data into a form that's more likely to be salient for a machine learning model.
- export—Print model objects to a textual representation.
  - exportApi 742—Generic export interface that can be passed around to different modules, without those modules knowing the export format.
  - exportImplCsv 744—A concrete implementation to export to a CSV.
- common utilities—These are agnostic to anything relating to sensor data, so they do not depend on our other modules. They are libraries that may be re-used across many different applications, not just our own.
  - Infinite 730—Implementations for processing infinite streams of data. Useful for processing large input data files line-by-line or chunk-by-chunk instead of loading the entire file into RAM memory.

brain 780—Implements both machine learning for both model training and classification.

app 710—Glues all the modules together, acting as a mediator. Provides a command line interface.

Data Flow

Figure 20:
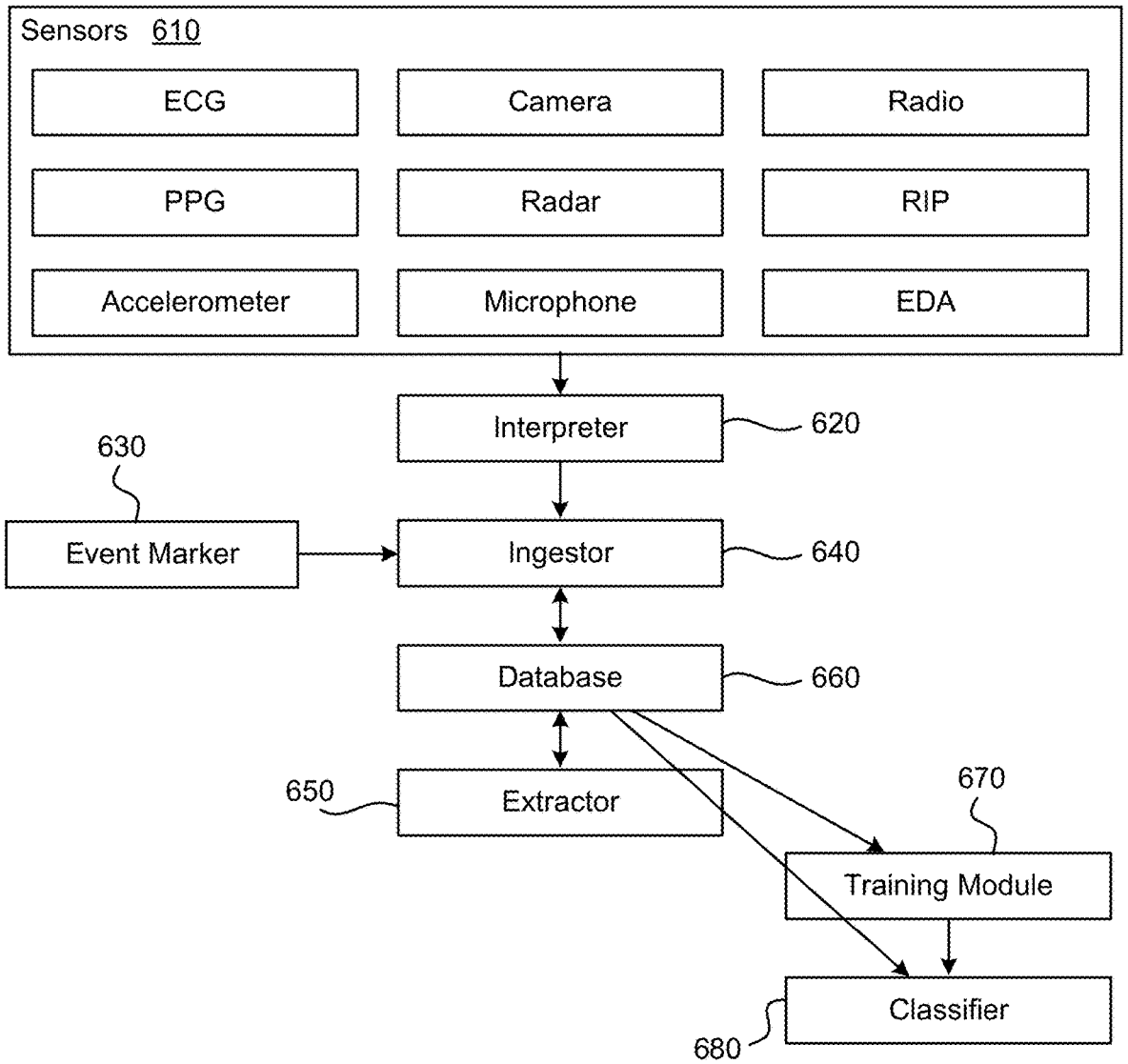
FIG. 20 is a block diagram of the data flow between several different high-level components and software modules.
Figure 21A:
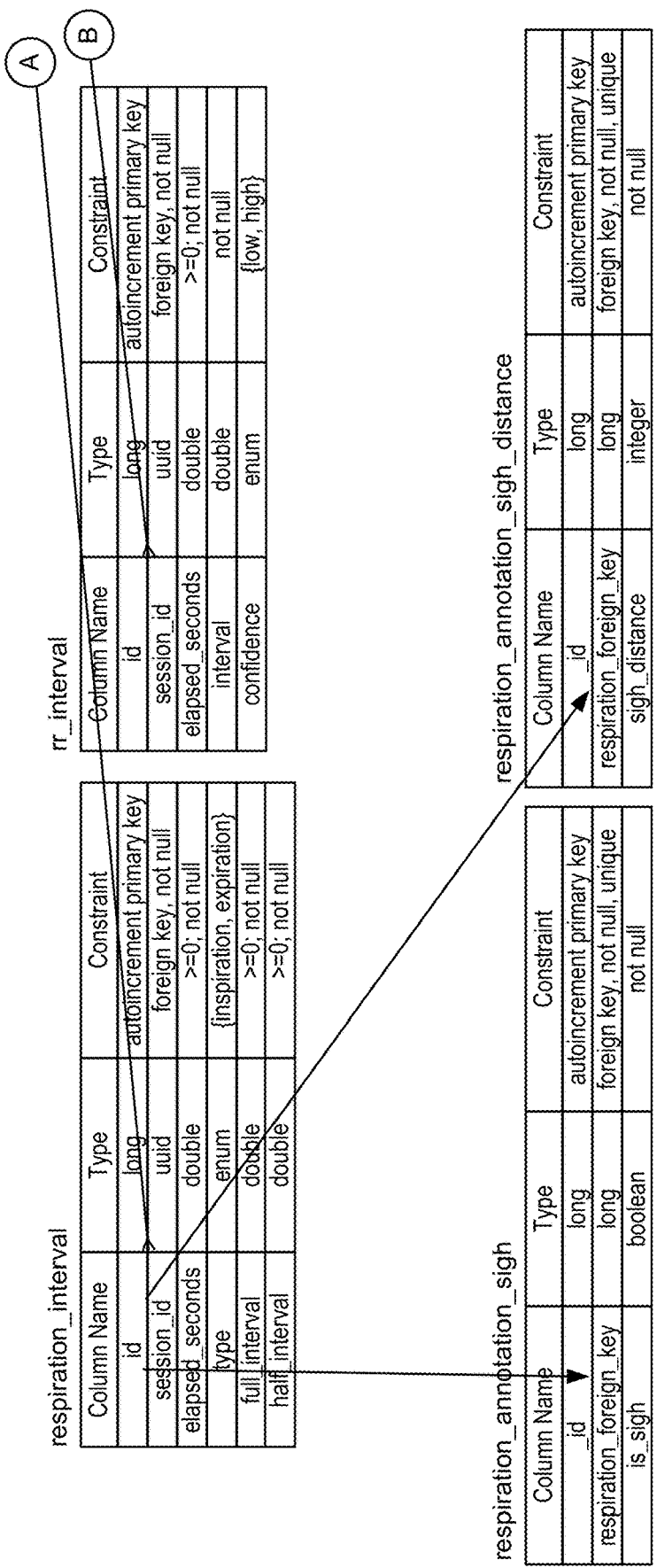
FIGS. 21A-E show an example of data representation after database ingestion during classifying.
Figure 21B:
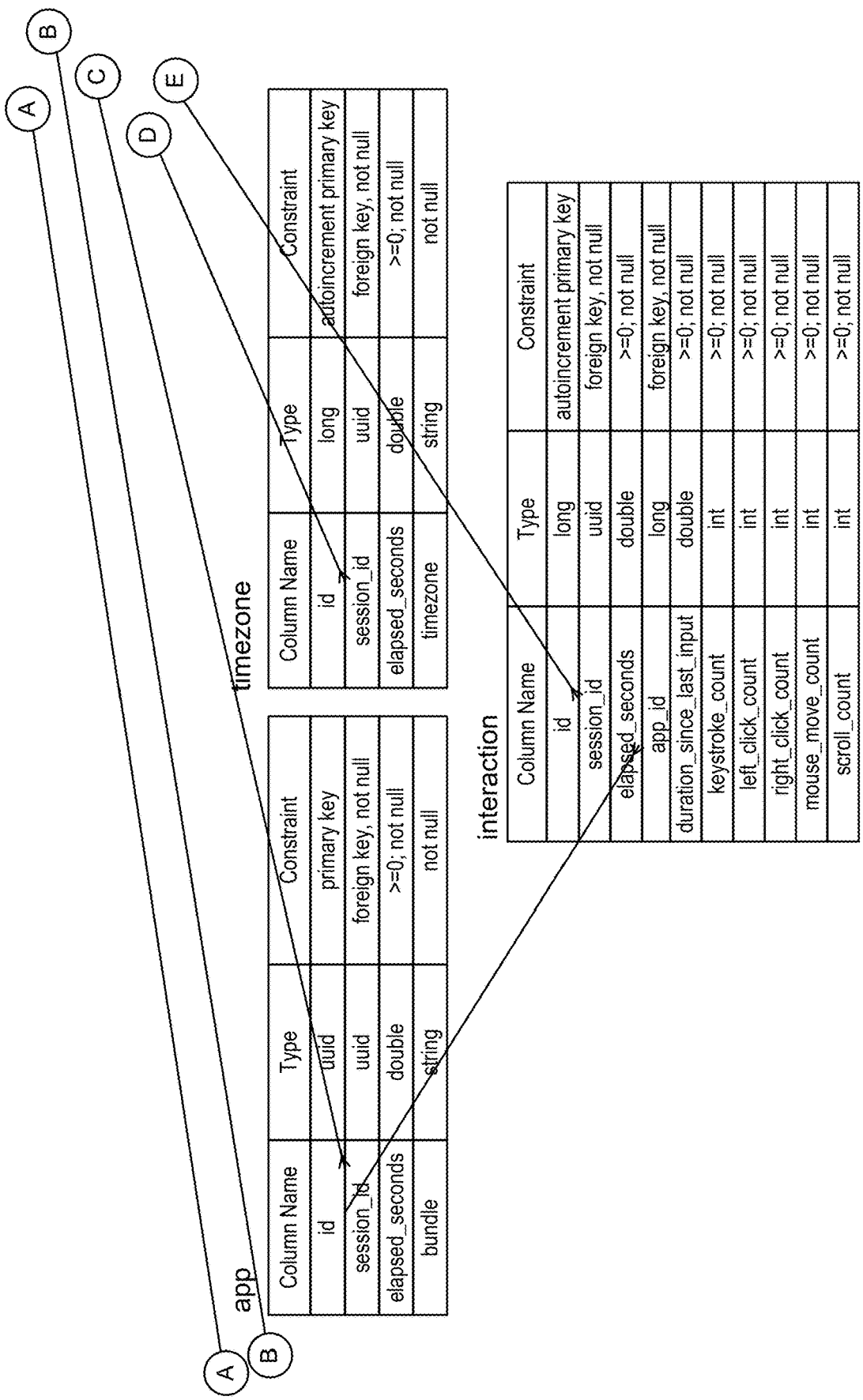
Figure 21C:
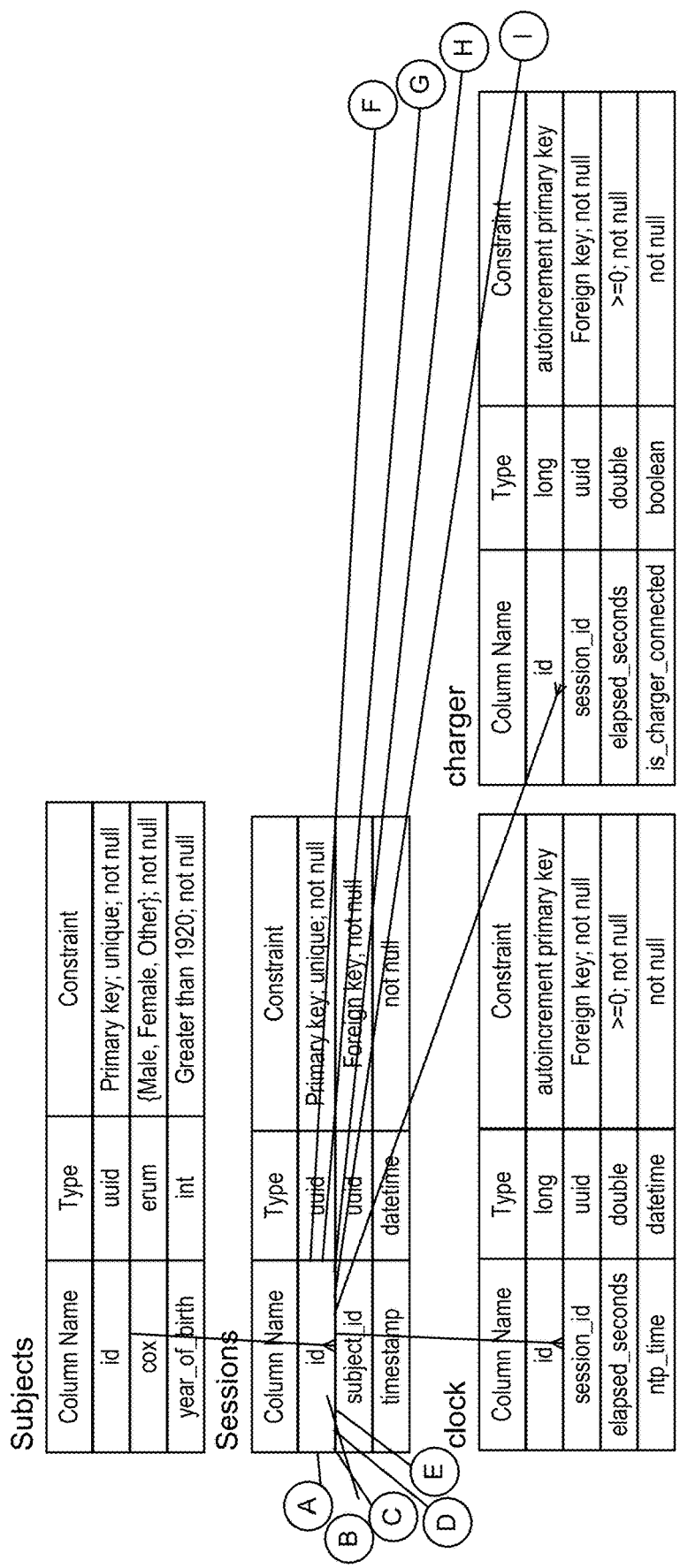
Figure 21D:
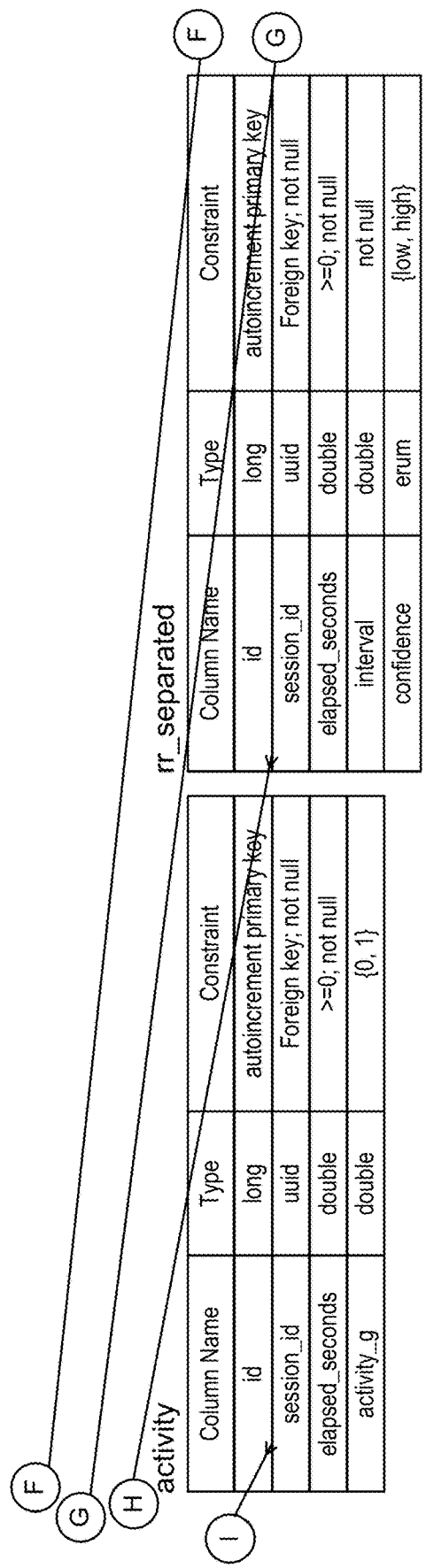
Figure 21E:
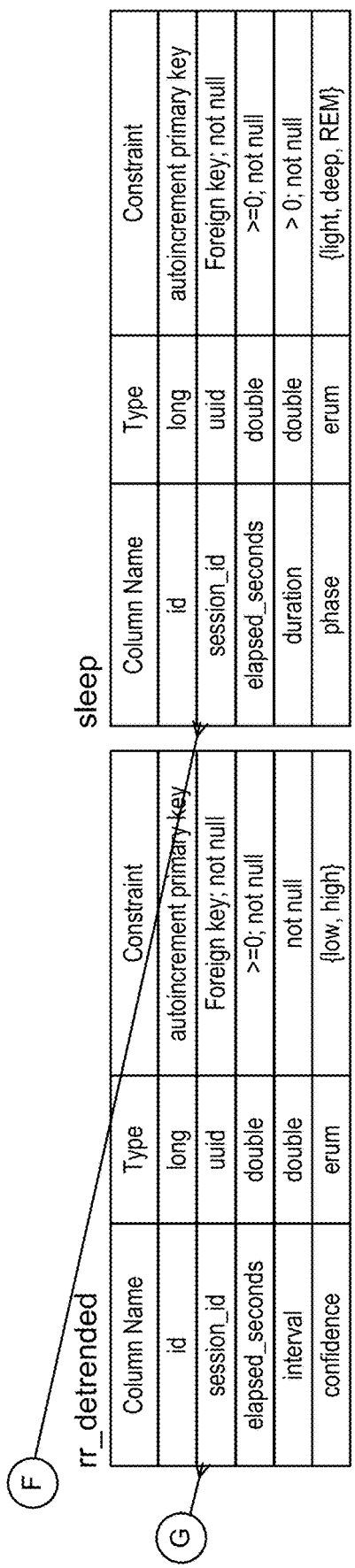
Figure 22D:
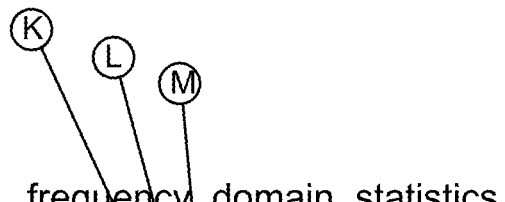

FIG. 20 is a block diagram of the data flow between several different high-level components and software modules. An example of these high level components and modules is described as follows:

Sensors 610—Captures readings from various sensors.

Interpreter 620—Performs various algorithms on the sensor data to interpret sensor readings. This may be part of the sensor or part of the system, as described previously under the section Sensing—Capture vs. Algorithmic Interpretation. Examples of algorithms that may be implemented in this layer include Pan-Tompkins for RR interval detection or the Advanced Counting Algorithm for breath interval detection. These are just examples and other algorithms can be implemented in this module.

Event Marker 630—Generates event markers, as described in the section Event Marking.

Ingestor 640—Receives sensor data (or interpreted sensor data), as well as optional event markers, and loads them into the database.

Extractor 650—Extracts features based on previously ingested data, then writes extracted features back into the database.

Database 660—Intermediate storage used for ingested and interpreted sensor data, as well as extracted features.

Training module 670—Reads data from the database, consisting of the output of the ingestor, extractor, or a combination of the two, and generates a Classifier.

Classifier 680—The output of the Training. Reads data from the database, consisting of the output of the ingestor, extractor, or a combination of the two, and generates classifications.

System Detail—Interruptions

Individuals working are interrupted frequently by other people and by electronic systems. In an office, an individual could be interrupted by a coworker. At home, an individual could be interrupted by a family member. Interruptions can also come from calls, messages, emails, and other forms of communication. Apple Watch reminds users to stand once per hour and to "breathe" during the day.

Calculating Cost

Given a system that can detect mental state (No. 1), the system can determine how detrimental an interruption at any given time could be. In some embodiments, the system estimates a cost of interrupting the individual in terms of dollars, time, or an arbitrary scoring system that may be numeric or semantic (e.g. "low", "medium", or "high"). In some embodiments, the status is reported as mental state such as "vigilance", "overload", "flow", "incubating", "available." In other embodiments, the status is binary such as "busy" or "available." There are various times when a user should and should not be interrupted, many of which are not necessarily obvious to either person. The following sections will cover both obvious and non-obvious shifts in mental state and how this implies different degrees of availability or costs of interruption.

Overload

Effortful tasks can benefit from stopping for multiple reasons. One reason is when a person gets "stuck" on the problem or perceives the problem as too difficult for current skills and then "mind wandering" may help (discussed under Incubation below). The person ends up in a state of overload (e.g., when preparing a tax return, doing math homework), takes a break that facilitates mind wandering, has a creative insight, and then returns to the task often in a state of flow. This has been discussed previously; an external interruption (e.g., from a colleague) before such mind wandering (or during) would not be helpful and would be high cost.

However, not all effortful tasks require this default mode thinking to improve performance. One example is an effortful task that has been completed, at which point a period of mind wandering afterwards may not be helpful; in this case an external interruption is acceptable and would be low cost. Another example is that some effortful vigilance tasks cause fatigue or lapses in vigilance, which can cause errors. An example of such a vigilance task may include human security screeners looking at X-ray of luggage. This is a type of effortful attention task that often requires a break after a relatively short period of time, such as 20-30 minutes, in which case an external interruption would be welcome and thus low cost. Regardless of the category of effortful task, in some embodiments, the system identifies an effortful task based on knowledge of the task itself or classification of the user's mental state, and therefore signals that an interruption is high cost, low cost, or that the mental state is overloaded, or in a state of vigilance.

In some embodiments, the system understands the type of effortful task and whether it would likely benefit from mind wandering or not. In some embodiments, the system detects that the user has been overloaded for too long in such a task, needs a break, and identifies this as a time to be interrupted by the system and may also produce a cost for an external interruption. In some embodiments, the system detects natural stopping points for the task, such as closing a document, and identifies this as a low-cost time to be interrupted.

Thus, there are two general types of interruptions, system interruptions, where the system will interrupt the user to take a break in order to facilitate mind wandering or to increase vigilance, and external interruptions from colleagues, telephones, electronic mail, etc. The "cost" of an external interruption depends upon the mental state and task: before and during "mind wandering" the cost is high; when overloaded during vigilance the cost is high unless the user is reaching a point of fatigue; during flow the cost is high; after completion of a task the cost is low; etc. As discussed below, a physical status sign 450 informs others that an external interruption is desirable or not.

Flow

In some embodiments, the system identifies flow as a high-cost period of interruptions because the user is being productive. In some embodiments, the system identifies the type of the task when making this determination. For example, a task may be writing an e-mail message which might be considered a low-cost interruption even if the user is detected as being in flow during that task. In some embodiments, this determination is made based on prior user input to classify productive versus neutral or unproductive applications or tasks that the user performs.

Incubation

There are various times when a user should and should not be interrupted, many of which are not necessarily obvious to people. For example, a common pattern in open offices is to wait until someone stands up from their desk or starts moving away from their desk. At this point, one or more people may approach to ask questions because the person no longer looks "busy." But depending on the mental state of the person, this could be a very disruptive time to interrupt. When we stop working on a task, our brain's default mode network becomes active. The default mode network can be active when working on a habitual task, such as folding laundry, making coffee or tea, going to the bathroom, or other simple tasks that do not require working memory, reading, writing, listening, or speaking. When we shift from working on a task, whether we were in overload or flow, and then move away to a habitual task, our default mode can then be active. During this time, we are significantly more likely to have instances of insight thinking. If someone is interrupted during this time, the process of insight thinking will be disrupted.

Therefore, some embodiments of the system identify such incubation periods as having a high cost of interruption. Some embodiments may use direct estimation of mental state as determined by physiological metrics to identify periods of incubation. In other embodiments, periods of incubation are determined by a period after the user stops performing a task. For example, if a software engineer was engaged in a productive task and then leaves their desk, the system might allow for a several minute incubation period before considering the cost of interruption to be low.

In some embodiments, the incubation period is reduced or eliminated if the user completed a task. Task completion may be identified explicitly by input from the user. Task completion may also be implied through automatic means such as closing a document, requesting a review of work, or marking a task as completed in a tracking system. The incubation period can be short circuited in a variety of other ways, which are described in the following Piggybacking section.

Piggybacking

In some embodiments, the system detects the user has been interrupted already and therefore identifies this time as low cost for further interruptions. In some embodiments, this "piggybacking" period is limited to a certain time span, such as a few minutes. In other embodiments, this piggybacking period can be extended by each subsequent interruption. A risk of these extensions is "starvation" of the user's attention if the interruptions never stop, and therefore keep getting extended. In some embodiments, the extensions decay in length to prevent this. For example, in a decay of ½ the first period may be 5 minutes, then 2.5 minutes, then 1.25 minutes. Other time periods and decay methods are possible, and these are just examples. In some embodiments, there is a maximum number of interruptions allowed regardless of remaining length of decay period.

In some embodiments, the piggybacking period is started by the user switching to a distracting task, such as switching to a neutral or distracting application on their computing device. In some embodiments, the piggybacking period is started by the user finishing another disruption such as hanging up a phone call, ending a video conference, or exiting a meeting. Phone calls and video conferences can be automatically detected by the Event Marking component. In some embodiments, location is used to identify these transitions, such as the user entering or exiting a conference room.

In some embodiments, the piggybacking period is started when the user returns from an extended break such as lunch. In other embodiments, the piggybacking period starts when the user returns to their computing device for the first time after an extended period away (longer than the Incubation period). In some embodiments, the piggybacking period is started by tracking whether the user has been speaking within a recent time period, such as a few minutes. Speaking can be determined using microphones, by changes in breathing that indicate speaking, or by facial landmark tracking. In some embodiments, the piggybacking period begins before an anticipated disruption. For example, the system may have access to the user's calendar and understands that a meeting is coming up and therefore opens the piggybacking period for a few minutes prior to the meeting or after the meeting.

Office Hours

In some embodiments, the user identities certain periods of time as "office hours" or "on call" for a period when interruptions are lower cost even if they would otherwise be considered high cost by the system.

Limits

In some embodiments, the system places a limit on the number of times or total duration during which a user's cost of interruption is identified as low for a given period. For example, a user may be considered interruptible for a certain number of minutes per day or as a percentage of time versus other classified mental states.

Predictions

One limitation of using only detected states is starvation. If a user is in an unclassified state, repeated interruptions could prevent the user from ever getting to a classified state as transitions between states may not necessarily be instantaneous. In particular, the system can apply this technique for the transition into flow as transitions to overload and underload are easier to shift into quickly. While the idea of limits mentioned immediately above can help, an additional approach is to use predictions of mental state shifts. In some embodiments, the system uses predictions of a shift in mental state to temporarily increase the cost of interruption for a reasonable period to allow for the transition to flow. In some embodiments, this transition period may be up to about 20 minutes.

Physical Status

In some embodiments, the cost of interruption is displayed using a physical indicator. Broadcast studios often have an "on air" indicator to signal that a live broadcast is currently happening. Similarly, a "do not interrupt" indicator may be used in an office environment. In other embodiments, the cost may be signaled as low, medium, or high or may be signaled with colors like a "traffic light." In other embodiments, this may be a flag that is raised and lowered to indicate status. In some embodiments, this indicator is placed outside of an individual's office or cubicle. In other embodiments, the indicator is placed on the back of the chair or on top of a monitor. In other embodiments, this may be a device the user wears, such as a hat, badge, or other article.

Shown at 450 in FIG. 18 is an example of such a physical mental status indicator with a cost placed upon a user's desk. Of course, an indicator may be placed in other places and appear in different forms as described directly above.

Electronic Status

In some embodiments, status is indicated through an electronic or virtual indicator. Such an indicator can be implemented using new technology, integrated into existing technology, or implemented as a proxy or agent in existing technology.

New Technology

In some embodiments, status is reported to a server that other clients can check. Other users who might want to interrupt the individual can check the server prior to interrupting. In other embodiments, status is communicated through peer-to-peer or a distributed mechanism. In some embodiments, status is visible through a dashboard of statuses.

Existing Technology

In some embodiments, status sharing is integrated into existing communication technology. In some embodiments, status is indicated through an existing "buddy list" like that used for various instant messaging applications which allow the user to manually set a status. In some embodiments, status of cost of interruption or mental state is indicated by a new user interface element integrated into the application or tool used to interrupt the individual experiencing flow. For example, when the user brings up a contact on a mobile phone, the contact card interface may have a status indicator of the individual. Similarly, when the user brings up a messaging app to write the individual, status may be displayed.

Agent

In some embodiments, status is indicated when the interrupter attempts to contact the individual using the system. In some embodiments, an "agent" operates on behalf of the individual user of the system. The agent may decide how to handle the incoming interruption such as allowing, blocking interruptions, or disambiguating interruptions. In some embodiments, the agent integrates with legacy technologies that do not understand the notion of status. For example, the agent may read emails, text messages, Slack messages, or other forms of communication through an API or by directly interacting with these existing services.

In some embodiments, the agent responds with a canned reply indicating that the individual is experiencing flow or is in a state where interruption is high cost, so that messages are being held. In some embodiments, the agent asks the sender if the message is important, allowing the interrupter an opportunity to override the agent. In some embodiments, the agent identifies the interrupter or contents of the message as being important and automatically decides whether to interrupt. In some embodiments, the individual using the system has told the agent previously to expect an important message from a specific interrupter and the agent allows the communication to go through.

The benefit of such an agent is that the system does not have to be implemented end to end. For example, consider user 1 is trying to interrupt user 2 via a SMS message. User 2 has the agent running on his mobile phone. User 1 does not know anything about the agent. Because the agent is operating over an existing standard of communication in plain language, user 2 gains the benefit of the agent without requiring user 1 having any knowledge of the system or installing any software. Although this example uses SMS, the system is not limited to SMS messages and may apply to a variety of systems.

In some embodiments, the agent is not able to interact deeply enough in the system to respond to incoming requests and so instead the agent runs as a proxy. For example, consider an existing plain old telephone system (POTS). The individual may transfer his original telephone number to the agent, and then the individual receives a new telephone number. When others call the original telephone number, the agent decides whether to forward the call or not. In some ways, the agent may be thought of as a virtual secretary that intercepts incoming communications and negotiates with the interrupter as to whether the interruption is important enough given the current cost of interruption.

API for Status

In some embodiments, the cost of interruption is made available to other applications or devices that the user has. For example, a device like the Apple Watch can remind a user to stand once per hour. If the user is in a state of flow, for example, this is a terrible time to remind the user to stand. In some embodiments, such applications or devices may avoid delivering notifications until the cost of interruption is lower.

Delayed Interruptions

When an interrupter is aware of a higher cost of interruption, some embodiments enable the interrupter to request delayed delivery of the interruption for when the cost of interruption is lower, or a certain amount of time has passed. For example, a request may not be immediately urgent but may become urgent after a certain amount of time. This time deadline may be exact (e.g. notify within 30 minutes or notify at 4 p.m.). The time deadline may also be variable with an increasing cost function that is compared to the cost of interruption, where interruptions occur only when the cost of not receiving the interruption exceeds the cost of being interrupted.

In some embodiments, the deadline can be extended briefly if a shift in mental state is detected. For example, the user's mental state may be classified as in flow with a high cost of interruption. The user may exit flow to take a break, yet the break may be a period when the user will be incubating. In such cases, the interruptions may be delayed until the incubation period ends which is expected to be brief. In some embodiments, the interrupter can request to be notified when the cost of interruption of another user is reduced. In other embodiments, the system also uses the cost of interruption of the original interrupter to decide when to deliver the notification of status change. These approaches may be useful for ad hoc meetings in a work environment, for example, by allowing the notification to be delivered when both parties are mutually in a state where cost of interruption is low.

In some embodiments, the notification may be through an existing mechanism. For example, consider the agent use case. When an individual's cost of interruption changes (or the deadline passes), the agent could notify interrupters through the same channel their original request came in. This enables others to take advantage of the system, without having access to the system themselves.

Prediction of Status Change

In some embodiments, the system shares predictions of when the individual's cost of interruption may change. This allows the interrupter to plan a future time to try interrupting the individual again. For situations when the interrupter needs real-time communication, these predictions may be very useful. For example, face to face interaction, phone calls, or video conferences.

Blocking of Notifications

In some embodiments, the system blocks a notification or interruption by not displaying a message, by not displaying an unread indicator, by not sounding a tone or audio message, by not vibrating, or by not emitting light associated with said notification.

System Detail—Coaching

Many individuals can improve or change their health or mental state through coaching. Such coaching can reduce stress, improve attention, and boost motivation. The present system can provide such coaching. In addition, the system can also help users shift mental state or exit flow at an appropriate time. Although flow is considered "good," the long-term goal of regular flow experiences may be impeded paradoxically by too much flow on a given day (e.g. by trading off sleep). In some embodiments, the system that can understand mental states can offer various types of coaching to encourage shifts in mental state. Different mental states have different properties, and therefore different coaching approaches.

Managing Overload

When overloaded or in an effortful state of attention, people begin to get fatigued. When fatigue is detected (some techniques for detecting fatigue were described previously), the system may suggest the user take a break. In some embodiments, the system predicts when fatigue is likely to occur based on the type of task the user is performing and prior experience with time durations before fatigue sets in. In such cases, the system suggests taking a break before fatigue sets in.

Promoting Flow

Figure 1:
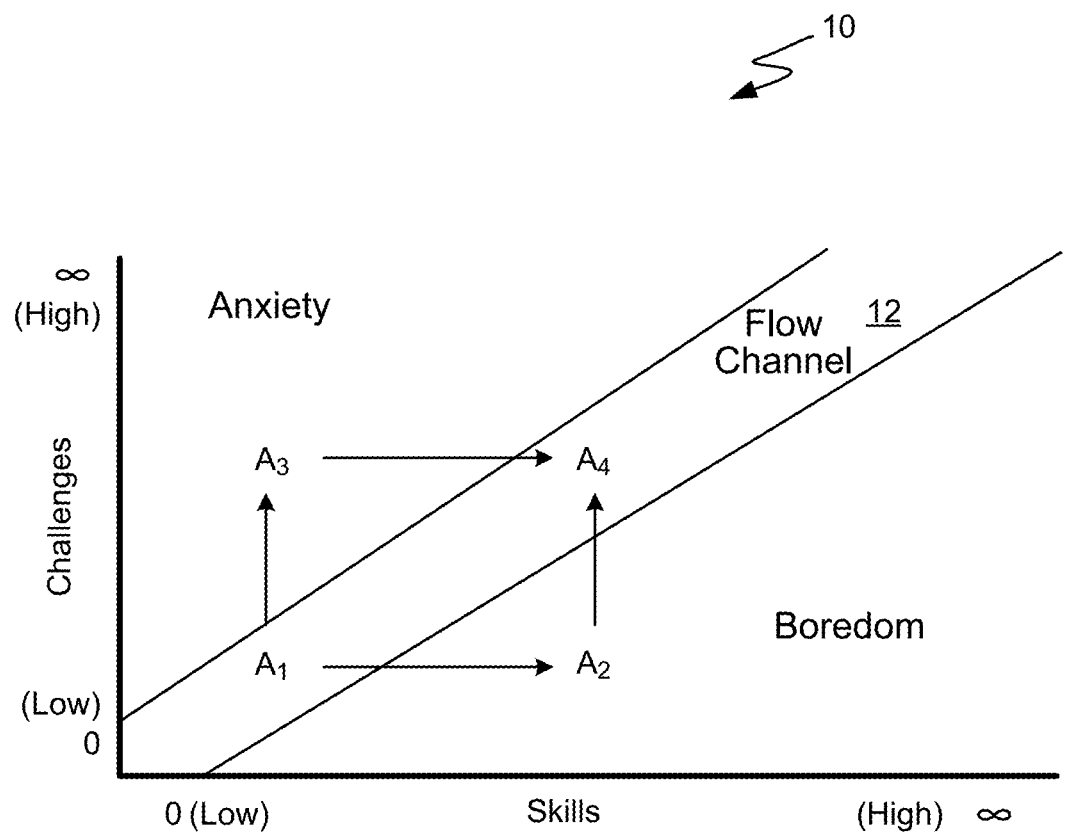
FIG. 1 is flow channel diagram.

Various techniques can promote experiencing flow. Flow can be thought of on a psychological level, as well as on levels of biology, physiology, and neuroscience. At a psychological level, flow can be described as a balance between being overloaded and underloaded or when challenge and skills are closely matched. This is depicted in FIG. 1.

Getting Started

In some embodiments, the system may initially suggest a task that should not be overloading in order to help the user "warm up" to finding flow for subsequent tasks. Such tasks may include editing documents, rather than writing new documents, or refactoring code, as opposed to writing new code. In some embodiments, the system coaches or helps the user break tasks down into smaller increments so that one or more increments can be successfully completed in a workday. Completing units of work boosts intrinsic motivation, which is a key component of flow experiences.

In some embodiments, the system suggests exercise at specific times of day to increase the likelihood of other non-exercise flow experiences, by triggering a variety of changes in the body and brain such as transient hypofrontality or reduction in stress. In some embodiments, the system suggests paced breathing at the average pace of breathing from previously classified states of flow. In some embodiments, the system detects when the user is overloaded and suggests mindfulness, meditation, and other stress reduction techniques including paced breathing at the user's resonant breathing rate which is approximately five to six breaths per minute and varies by body size.

Self-Interruption

Users often self-interrupt to switch to switch to something unimportant or distracting, without any kind of external prompt such as a notification. For example, a user could be working productively and feel the urge to check social media. Or a user may use a distracting app when taking a break, such as checking social media while going to the bathroom, interrupting the incubation process. In some embodiments, the system helps the user reduce the number and duration of internal interruptions based on the mental state of the user and the cost of self-interruption. In some embodiments, the system can rely on a cost generating function as described in Calculating Cost. Some embodiments of this coaching include completely blocking access to the distracting application or website. In other embodiments, the system nudges the user with a visible overlay suggesting that the user wait to use the distracting application or website for a few minutes.

Longer-Term

In some embodiments, the system coaches the individual on sleep patterns that improve the likelihood of flow. In some embodiments, the system coaches the individual on what time to go to bed. In other embodiments, the system coaches the individual on when to wake up. Specifically, the system coaches the user to match sleep with the user's personal natural circadian rhythm which implies waking at a regular time of day based on the user's response to light exposure and other zeitgebers.

In some embodiments, the system coaches the individual to experience more or less light exposure. Additional light exposure could stave off seasonal affective disorder, which could inhibit flow. On the other hand, reducing light exposure at night could improve sleep quality and thus promote flow. In other embodiments, the system exposes user to receive different wavelengths and intensities of light at different times of day. Some embodiments may suggest exposing the user to light with an intensity of 10,000 lux early in the day. Other embodiments may suggest specific wavelengths of light to be exposed to at different times of day.

Exiting of Flow

In some embodiments, the system coaches the individual to limit flow to an optimal amount. In some embodiments, the system may decide to bring the user out of flow even though the user is still in a flow state. In some embodiments, the system may decide to bring the user out of flow based on the duration the user has been in flow during the current session. In other embodiments, the system may decide to bring the user out of flow based on the duration of flow the user has experienced during a previous time interval, such as over the current day. In other embodiments, the system may decide to bring the user out of flow based on physiological measurements. For example, the system may detect fatigue and bring the user out of flow. In other embodiments, the system discourages the user from seeking flow late in the user's day as experiencing flow close to bedtime can make it difficult to fall asleep. The timing of "late in the user's day" is based on the user's recent sleep cycles to account for variations in sleep schedules.

Flow can be a state of high arousal, and the release of dopamine and norepinephrine during flow can make sleep difficult. While flow by itself can be good, if flow disrupts sleep one night then it could reduce the probability of flow the next day. In some embodiments, the system attempts to maximize overall flow over time rather than maximizing a single session of flow.

Anti-Predictions

The Predicting component may know that flow is not likely. In some embodiments, the system may coach the individual to do a non-flow activity since flow is not likely. For example, instead of working the user may do other tasks like chores or grocery shopping. By addressing these non-flow activities during a period of low flow likelihood, the individual may have more time in the future to experience flow when flow is more likely. Examples of times when flow is not likely can include times when the user is sick, hungover, highly stressed, or sleep deprived. Other times can include an understanding of the user's schedule, such as identifying that a given day has too many meetings with few blocks of uninterrupted time. Addressing various small tasks during gaps between meetings would potentially allow for more contiguous blocks of time on a subsequent day. These are just examples, and other situations also can trigger this coaching. In other embodiments, the system may coach the user to do an activity to improve likelihood of flow in the future. For example, the coach may suggest exercise, meditation, going to bed at a particular time, or other interventions to improve the likelihood for flow in the future.

System Detail—Advertising

The user's receptiveness to an advertisement may vary depending on the user's mental state. There is an adversarial component, in that users may prefer to resist or avoid advertisements while advertisers would prefer to influence users with advertisements.

In some embodiments, the presence, type, or quantity of advertising may vary based on the user's mental state. While a variety of advertising mediums are distracting (social media, for example), a variety of ads also appear in products or experiences where users are engaged in actual work. For example, users may listen to music while working and the music may contain advertising. In another example, users may be using ad supported productivity software.

In some embodiments, advertisers receive information about the mental state of a user when an advertisement is delivered and the user's engagement with the advertisement is tracked. Future delivery of advertisements can be adjusted based on the user's personal history, as well as the history of other users. For example, if the user clicks or hovers over an ad, makes a purchase, or otherwise interacts with the add, then that engagement with the advertisement feeds back into the system to adjust future delivery. In some embodiments, the system may eliminate or reduce advertising to reduce advertising costs when it is expected the user is not receptive to advertising based on the user's mental state.

In some embodiments, the system uses an identified state of flow to reduce advertising. For example, a music streaming service may have audio ads. If the user is listening to music while working, and the user's state is classified as being in flow, then the system may reduce ads because the user is unlikely to engage with them. In other embodiments, the system may increase ads when flow is detected, to annoy the user and therefore drive the user to pay for a premium version of the service without ads. In other embodiments, the system may increase advertisements shortly after flow. Because flow is a state of positive valence, users are likely to be in a more receptive mood afterwards.

In some embodiments, the system uses a classified state of high stress to reduce the number of advertisements. Because stress causes narrower thinking, people may be less likely to notice things in their environment like advertisements. This reduces advertising costs, as well as improves the experience for the user who was unlikely to engage in the advertisement. One exception to this is if the system understands exactly what is causing stress for the user, then a solution to that type of stress is highly salient. Therefore, in some embodiments, the system will increase advertisements if the system is highly confident that the advertisement contains a solution to the user's source of stress.

In some embodiments, intrusive advertisements are delivered based on the user's current cost of interruption. For example, a cold-call or interactive advertisement is best delivered when the user is in a lower cost state. In some embodiments, the system may adapt to using different types of advertisement. For example, if the user is in state that is higher cost of interruption in a VR experience then the user may be targeted with product placements rather than more disruptive types of advertisement.

System Detail—Game Playing

As described in the above Sensing—Event Marking via Computing Device Usage Game Playing section, difficulty of games can be adapted on how the user is performing during a task based on task-specific metrics. This can be used to help build a classifier, by associating game-playing task performance with periods of overload, flow, and underload. An alternative is to use the output of the classifier as an input to alter the difficulty of a game-playing task. When the user is detected as being overloaded, difficulty of the task can be decreased. When the user is detected as underloaded, difficulty of the task can be increased. When the user is detected to be in flow, difficulty of the task can be held constant.

It is important to note that a game-playing task can be used as input to training a classifier that is subsequently used to generate input for a game-playing task. While this may seem to be a circular argument, the game-playing task for training can be different from the game that uses output from the classifier. This allows knowledge about the user's mental state to be transferred from one domain to another.

Game-playing task difficulty may be adapted through various mechanisms, which vary based on game mechanics. Examples include:

Increasing or decreasing the speed of the game

Increasing or decreasing the number of enemy NPCs

Increasing or decreasing the player's health

Increasing the amount of damage the player's character receives

Increasing or decreasing the probability of random positive or negative events, such as items that appear in the game Increasing or decreasing the value of items that appear in the game The purpose of adapting the difficulty based on the user's mental state is to ensure the task is as engaging as possible.

In some embodiments, it might be valuable to intentionally cause the user to feel overloaded in the task after a period of time in flow. In some embodiments, the system intentionally tries to frustrate the user into quitting the task. While this may seem counter intuitive, several benefits emerge from this. One benefit is to help the player develop new skills by periodically creating challenges that exceed the player's current skill level. By feeling overloaded, the player may take a break, have a creative insight on how to solve the problem, then return to the game more motivated than before. Other benefits may be to improve the user's health by reducing gaming addiction or likelihood of injuries, such as repetitive stress injuries or eyestrain.

In some embodiments, the system is only able to detect overload. In such a case, the system can intentionally cause overload and then back off until overload is no longer detected. This approach therefore estimates flow, as it sits below overload. Such a scenario enables simpler sensors to be used, as overload is stressful and can be easier to detect than other mental states.

Additional Embodiments

The invention includes these additional embodiments.

A method as recited in claim 1 wherein having flow is said subject having a balance of challenge and skills.

A method as recited in claim 1 further wherein all of said sensors are contactless with respect to said subject.

A mental state monitoring system as recited in claim 7 wherein the subject's RR interval or interbeat interval is one of said features utilized by the classifier in the classification of the subject's mental state.

A mental state monitoring system as recited in claim 7 wherein the heart rate monitor is selected from the group consisting of:

an electrocardiograph;

a photoplethysmography sensor;

a camera that detects heart beats based on changes in skin color associated with heartbeats;

a head movement monitor that detects head movements associated with heart beats; and a vital signs monitor;

a radio wave disruption, reflection or scattering based sensor;

a microphone;

a radar based monitor; and a sleep tracker.

A mental state monitoring system as recited in claim 7 further comprising:

a hysteresis component configured to utilize a first threshold to place said subject in one of said mental states, to utilize a second threshold to place said subject back into said one of said mental states after an interruption, wherein said second threshold is lower than said first threshold and makes it easier to detect said subject being in said mental state after said interruption.

A mental state monitoring system as recited in claim 7 wherein said classified subject's flow level, stress level, attention level, and motivation level is each a probability of said subject having flow, stress, attention, and motivation.

A7. A mental state monitoring system as recited in claim 7 further comprising:

a device usage tracker that tracks one or more aspects of usage of a computing device by said subject; and wherein said classifier is further configured to receive selected device usage features detected by said device usage tracker in said classification of said subject's mental state.

A mental state monitoring system as recited in claim A7 wherein said device usage tracker identifies an application being used by said subject and said application used by said subject is utilized by said classifier in said classification of said subject's mental state.

A mental state monitoring system as recited in claim A7 wherein said device usage tracker tracks selected computer usage events and said selected computer usage events are utilized by said classifier in said classification of said subject's mental state.

B1. A mental state monitoring system comprising:

a breathing monitor for detecting the subject's breathing including a subject's breathing rate and variations in the subject's breathing rate between individual breaths; and a classifier configured to (a) receive features indicative of the subject's detected breathing rate and variability, and (b) classify the subject's mental state based at least in part on the received breathing rate and variability features.

B2. A mental state monitoring system as recited in claim B1 wherein the classified mental state is a probability of having said mental state and includes the flow, stress, attention, and motivation.

B3. A mental state monitoring system as recited in claim B1 wherein sighs detected in the subject's breathing is a feature utilized by the classifier in the classification of the subject's mental state.

B4. A mental state monitoring system as recited in claim B1 wherein speaking detected in the subject's breathing is a feature utilized by the classifier in the classification of the subject's mental state.

B5. A mental state monitoring system as recited in claim B1 wherein breath-to-breath intervals detected in said subject's breathing is a feature utilized by said classifier in said classification of said subject's mental state.

B6. A mental state monitoring system as recited in claim B1 wherein an inhale/exhale timing ratio and variability detected in the subject's breathing are features utilized by the classifier in the classification of the subject's mental state.

B7. A mental state monitoring system as recited in claim B1 wherein features detected in the subject's breathing utilized as features by the classifier in the classification of the subject's mental state include one or more of: yawns, sneezes, coughs, burps, and hiccups.

B8. A mental state monitoring system as recited in claim B1 wherein the breathing monitor is or includes at least one selected from the group consisting of:
- an airflow sensor;
- a strain gauge sensor;
- an accelerometer;
- a camera;
- an impedance sensor;
- a pulse oximeter;
- an ECG sensor;
- a heart rate variability sensor;
- an electrodermal activity sensor;
- a microphone;
- a radar-based monitor;
- a pupil dilation sensor; and
- an electromagnetic wave disruption, reflection or scattering based sensor.

B10. A mental state monitoring system as recited in claim B1 further comprising:
a hysteresis component configured to utilize a first threshold to place said subject in one of said mental states, to utilize a second threshold to place said subject back into said one of said mental states after an interruption, wherein said second threshold is lower than said first threshold and makes it easier to detect said subject being in said mental state after said interruption.

B11. A mental state monitoring system as recited in claim B1 further comprising:
a device usage tracker that tracks one or more aspects of usage of a computing device by said subject; and
wherein said classifier is further configured to receive selected device usage features detected by said device usage tracker in said classification of said subject's mental state.

B12. A mental state monitoring system as recited in claim B11 wherein said device usage tracker identifies an application being used by said subject and said application used by said subject is utilized by said classifier in said classification of said subject's mental state.

B13. A mental state monitoring system as recited in claim B11 wherein said device usage tracker tracks selected computer usage events and said selected computer usage events are utilized by said classifier in said classification of said subject's mental state.

C4. A mental state monitoring system as recited in claim 11 wherein the movement monitor includes at least one accelerometer.

C9. A mental state monitoring system as recited in claim 9 wherein the classifier is an artificial intelligence classifier, a machine learning classifier, a tabular classifier, or a neural network based classifier.

C10. A mental state monitoring system as recited in claim 9 wherein the classifier is a heuristic classifier.

C15. A mental state monitoring system as recited in claim C9 wherein the blocked notifications include at least one of:
- e-mail;
- text messages;
- phone calls;
- electronic alerts;
- computer operating system generated alerts;
- fitness prompts;
- instant messages;
- push notifications;
- video calls; and
- audio calls.

C16. A mental state monitoring system as recited in claim 9 further comprising:
a brain activity monitor; and
wherein the classifier is further configured to receive features indicative of the subject's brain activity detected by the brain activity monitor and to utilize the brain activity information in the classification of at least one of the subject's mental state.

C17. A mental state monitoring system as recited in claim C16 wherein the brain activity monitor is selected from the group consisting of an fMRI, an fNIRS, an EEG, and an MEG.

D1. A method of altering the difficulty of a task, said method comprising:
determining a subject's mental state while said subject is performing said task, said mental state being one of overload, flow or underload; and
altering a difficulty of the task based at least in part on said determined mental state while the subject is engaged in the task.

D2. A method as recited in claim D1 wherein said determining is performed by using a trained classifier to classify said mental state of said subject, said method further comprising:
inputting into said trained classifier at least one feature obtained from at least one sensor that measures physiological data of said subject.

D3. A method as recited in claim D1 wherein said determining is performed by measuring metrics of said task.

D5. A method as recited in claim D1 wherein when it is determined that said mental state is overload, said altering decreases said difficulty of said task.

D6. A method as recited in claim D1 wherein when it is determined that said mental state is overload, said altering decreases said difficulty of said task, wherein when it is determined that said mental state is underload, said altering increases said difficulty of said task, and wherein when it is determined that said mental state is flow, said altering holds constant said difficulty of said task.

D7. A method as recited in claim D1 wherein the adjusted difficulty is a task difficulty level, a task speed, or handicap level.

D8. A method as recited in claim D1 wherein said task is a computerized task.

D9. A method as recited in claim D1 wherein said task is a computerized game-playing task.

E8. A method as recited in claim 20 wherein said determining a subject's mental state using data from event marking includes receiving video data from a body camera worn by said subject while said subject is using said first computing device.

F1. A method for preventing interruptions of a subject, said method comprising:
determining using a classifier of a first computing device that a mental state of said subject is at least one of having flow, using effortful attention, and being overloaded;
determining that said subject has stopped performing a task on said computing device and is in an incubation period;
in response to said determining, determining that a cost of interruption of said subject is high; and
indicating to at least one other person or to a second computing device that said cost of interruption is high during said incubation period.

F2. A method as recited in claim F1 wherein said indicating uses at least one of a physical indicator, an electronic indicator, an electronic agent, and an API.

F3. A method as recited in claim F1 further comprising:
determining that said subject has completed said task; and
reducing or eliminating said incubation period.

F4. A method as recited in claim F1 further comprising:
determining that said subject has been interrupted; and
in response to said determination that said subject has been interrupted, indicating to said at least one other person or to said second computing device that said cost of interruption is low during a piggybacking period that begins immediately after said interruption.

F5. A method as recited in claim F1 further comprising:
delaying an interruption of said subject received from said at least one other person or from said second computing device until said incubation period ends, until a certain amount of time has passed or until a cost of not receiving said interruption exceeds said cost of said interruption; and
delivering said interruption from said other person or said second computing device to said subject.

F6. A method as recited in claim F1 further comprising:
predicting a future time when said cost of interruption of said subject will be low and notifying said other person or said second computing device person of said time; and
delivering an interruption from said other person or said second computing device to said subject after said time.

G1. A method for preventing interruptions of a subject, said method comprising:
determining using a classifier of a first computing device that a mental state of a subject is at least one of having flow, using effortful attention, and being overloaded;
determining that a cost of an interruption of said subject is high based upon said determining that said mental state is having flow, using effortful attention, or being overloaded; and
in response to said determining that a cost of an interruption is high, blocking a notification from a second computing device from reaching said subject.

G2. A method as recited in claim G1 wherein said notification is from a mobile telephone, a tablet computer, a wearable computing device, or a computer.

G3. A method as recited in claim G1 further comprising:
inputting physiological data of said subject into said first computing device using sensors;
extracting a plurality of features from said physiological data; and
feeding said extracted features into said classifier to classify said mental state of said subject.

G4. A method as recited in claim G1 further comprising:
blocking said notification from reaching said subject at a current time;
predicting a future time when said cost of interruption of said subject will be low and notifying said second computing device of said future time; and
delivering said notification from said second computing device to said subject after said future time.

G5. A method as recited in claim G1 further comprising:
relaying said determination that said cost of an interruption of said subject is high to a software agent;
in response to said relaying, said software agent blocking said notification from said second computing device from reaching said subject.

G6. A method as recited in claim G1 wherein said first and second computing devices are the same computing device, said method further comprising:
said same computing device blocking said notification by not displaying a message, by not displaying an unread indicator, by not sounding a tone or audio message, by not vibrating, or by not emitting light associated with said notification.

Computer System Embodiment

Figure 23A:
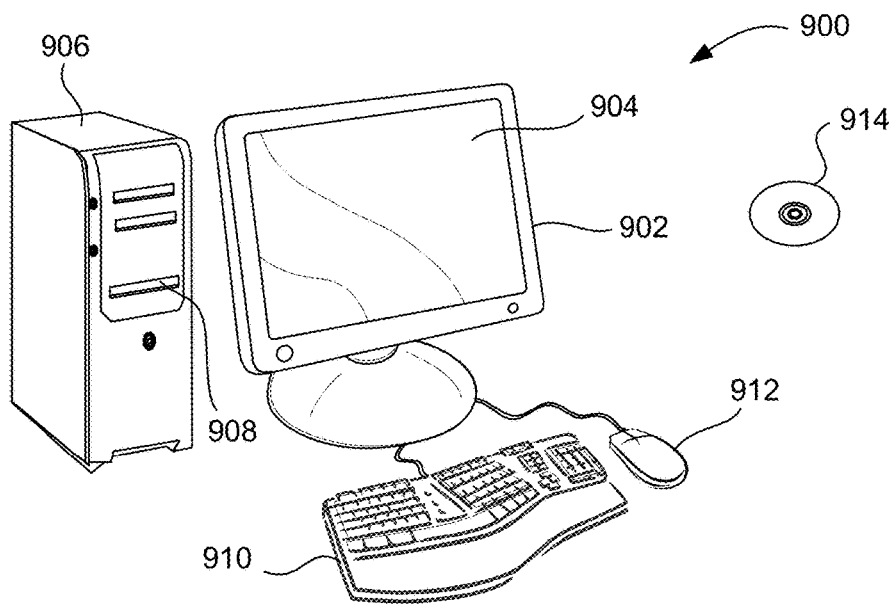
FIGS. 23A-B illustrate a computer system suitable for implementing embodiments of the present invention.
Figure 23B:
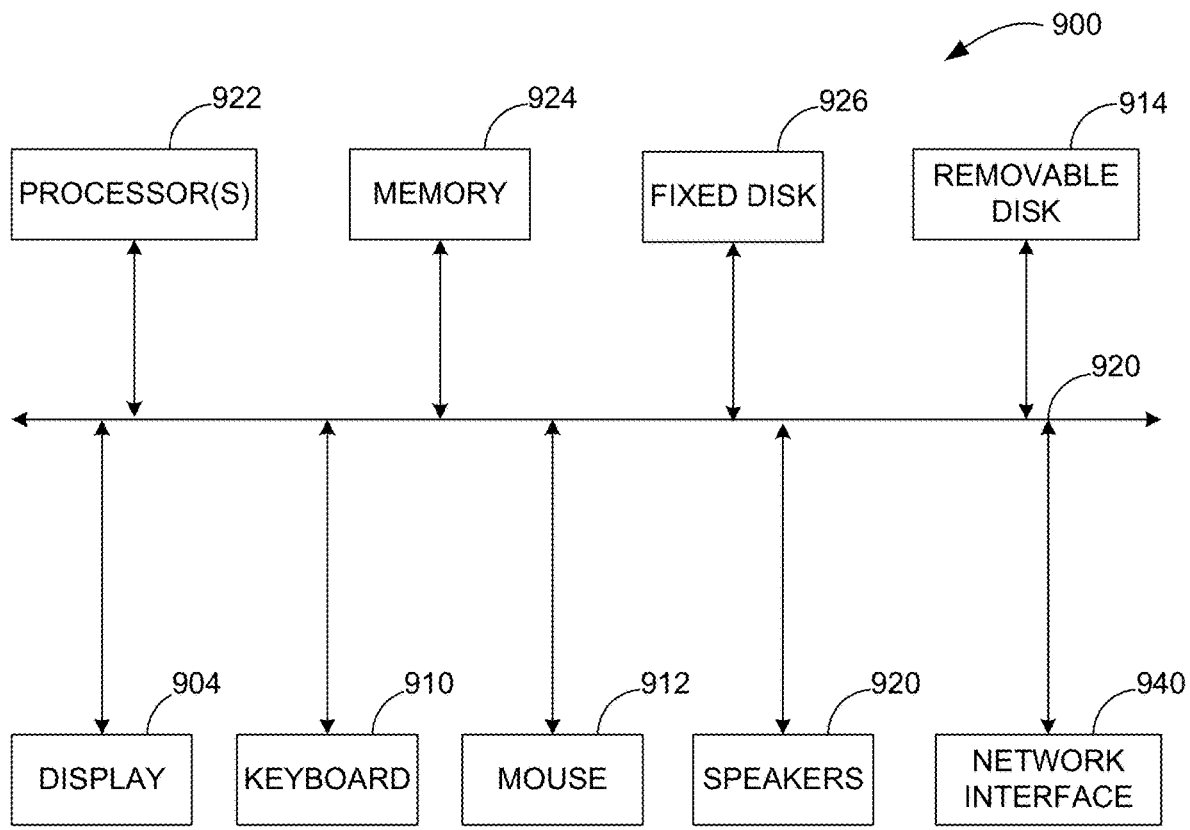

FIGS. 23A and 23B illustrate a computer system 900 suitable for implementing embodiments of the present invention. FIG. 23A shows one possible physical form of the computer system. Of course, the computer system may have many physical forms including an integrated circuit, a printed circuit board, a small handheld device (such as a mobile telephone or PDA), a personal computer or a super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 23B is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary mass storage medium (such as a hard disk, a solid-state drive, a hybrid drive, flash memory, etc.) that can be slower than primary storage but persists data. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher-level code that are executed by a computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

The invention claimed is:

1. A mental state monitoring system comprising:
a first processor configured to:
receive data of a subject from a heart rate monitor;
extract a heart rate variability signal and a breathing rate from the data; and
perform a frequency domain analysis on the heart rate variability signal, wherein a frequency range used for the frequency domain analysis is adjusted based on the breathing rate to obtain an adjusted heart rate variability signal;
a second processor configured to:
execute a classifier configured to:
receive the adjusted heart rate variability signal from the first processor;
classify a mental state of the subject by computing a probability of the mental state, wherein the mental state is selected from the group consisting of flow, stress, attention and motivation, and wherein the probability of the mental state is computed based at least in part on the received adjusted heart rate variability signal;
determine a cost of an external interruption based at least in part on the mental state of the subject, wherein the external interruption is generated by a person or a computing device; and
instruct a notification blocker to block a device generated notification if the cost of the external interruption exceeds a first threshold; and
the notification blocker configured to:
receive an instruction from the second processor; and
determine whether to block the device generated notification in response to the instruction.

2. A mental state monitoring system comprising:
a heart rate monitor configured to measure heart rate data of a subject;
a breathing monitor configured to measure breathing data of the subject;
a first processor configured to:
receive the heart rate data and the breathing data; and
extract a heart rate variability signal from the heart rate data and a sigh rate of periodically triggered sighs from the breathing data, wherein extracting the sigh rate comprises using a sliding window function across time applied to the breathing data, wherein the sliding window is used to detect a sigh based at least in part on the detection of a slower or a less variable breathing in the breathing data following the sigh; and
a second processor configured to:
execute a classifier configured to:
receive the heart rate variability signal and the sigh rate from the first processor; and
classify a mental state of the subject based at least in part on the received heart rate variability signal and the sigh rate.

3. The mental state monitoring system of claim 2, wherein the classifier is configured to classify the mental state by computing a probability of the mental state, and wherein the mental state is selected from the group consisting of flow, motivation, overload, underload, distraction, interruption, pleasure, misery, arousal, sleepiness, distress, excitement, busyness, task switching, depression, contentment, effortful attention, effortless attention, and a default mode of attention.

4. The mental state monitoring system of claim 2, further comprising:
a movement monitor configured to measure body movement data of the subject, wherein the classifier is further configured to:
receive the body movement data; and
classify the mental state of the subject based at least in part on the received body movement data.

5. The mental state monitoring system of claim 2, further comprising:
a device usage tracker configured to measure one or more aspects of a usage of a computing device by the subject, wherein the classifier is further configured to:
receive a feature extracted from the measured one or more aspects of the usage of the computing device; and
classify the mental state of the subject by computing a probability of the mental state, wherein the probability of the mental state is computed based at least in part on the received feature, and wherein the mental state is task switching.

6. The mental state monitoring system of claim 2, further comprising:
a device usage tracker configured to measure one or more aspects of a usage of a computing device by the subject, wherein the one or more aspects of the usage of the computing device comprises a task difficulty level of a task that the subject is performing and a task progress level of the subject, wherein the classifier is configured to classify the mental state of the subject based at least in part on the task difficulty level and the task progress level.

7. The mental state monitoring system of claim 2, further comprising:
an eye blink rate monitor configured to measure a baseline eye blink rate of the subject,
wherein the first processor is configured to:
estimate a circadian rhythm of the subject; and
adjust the baseline eye blink rate based on the circadian rhythm to obtain an adjusted eye blink rate,
wherein the classifier is further configured to:
receive the baseline eye blink rate and the adjusted eye blink rate; and
classify the mental state of the subject based at least in part on the received baseline eye blink rate and the adjusted eye blink rate.

8. The mental state monitoring system of claim 2, further comprising a notification blocker configured to:
  receive an instruction from the second processor; and
  determine whether to block a device generated notification in response to the instruction,
wherein the second processor is configured to:
  determine a cost of an external interruption based at least in part on the mental state of the subject, wherein the external interruption is generated by a person or a computing device; and
  instruct the notification blocker to block the device generated notification if the cost of the external interruption exceeds a threshold.

9. The mental state monitoring system of claim 3, wherein the classifier is configured to:
  classify the mental state at a first point in time using a first threshold;
  detect a change in the mental state at a second point in time relative to the mental state at the first point in time due to an interruption; and
  classify the mental state at a third point in time using a second threshold after the change in the mental state is detected, wherein the second threshold is different from the first threshold.

10. A mental state monitoring system comprising:
  a heart rate monitor configured to measure heart rate data of a subject;
  a breathing monitor configured to measure breathing data of the subject;
  a first processor configured to:
    receive the heart rate data and the breathing data;
    extract a heart rate variability signal from the heart rate data and an idealized respiratory waveform from the breathing data, wherein the idealized respiratory waveform comprises variations across time in an interval between two inhale peaks or two exhale peaks; and
    remove a respiratory influence from the heart rate variability signal using the idealized respiratory waveform; and
  a second processor configured to:
    execute a classifier configured to:
      receive the heart rate variability signal after the respiratory influence is removed; and
      classify a mental state of the subject based at least in part on the received heart rate variability signal; and
    determine a cost of an external interruption based at least in part on the mental state of the subject, wherein the external interruption is generated by a person or a computing device;
    determine a cost of a failure to receive the device generated notification based at least in part on the mental state of the subject;
    instruct a notification blocker to delay the device generated notification if the cost of the external interruption exceeds a first threshold;
    compare the mental state classified at a first point in time to the mental state classified at a second point in time; and
    instruct the notification blocker to stop the delay of the device generated notification if an amount of time has passed after the second processor determines that the cost of the external interruption exceeds the first threshold, the mental state classified at the first point in time is different from the mental state classified at the second point in time, or the cost of the failure to receive the device generated notification exceeds the cost of the external interruption; and
  the notification blocker configured to:
    receive an instruction from the second processor; and
    determine whether to delay the device generated notification in response to the instruction.

11. The mental state monitoring system of claim 10, wherein the notification blocker is further configured to:
  determine whether to block the device generated notification in response to the instruction,
wherein the second processor is further configured to:
  instruct the notification blocker to block the device generated notification if the cost of the external interruption exceeds a second threshold.

12. The mental state monitoring system of claim 10, further comprising:
  an eye blink rate monitor configured to measure a baseline eye blink rate of the subject,
  wherein the first processor is configured to:
    estimate a circadian rhythm of the subject; and
    adjust the baseline eye blink rate based on the circadian rhythm to obtain an adjusted eye blink rate, and
  wherein the classifier is further configured to:
    receive the baseline eye blink rate and the adjusted eye blink rate; and
    classify the mental state of the subject based at least in part on the received baseline eye blink rate and the adjusted eye blink rate.

13. The mental state monitoring system of claim 10, wherein the classifier is further configured to:
  classify the mental state of the subject at a first point in time using a second threshold;
  detect a change in the mental state at a second point in time relative to the mental state at the first point in time due to an interruption; and
  classify the mental state at a third point in time using a third threshold after the change in the mental state is detected, wherein the third threshold is different from the second threshold.

14. The mental state monitoring system of claim 10, wherein the classifier is further configured to:
  classify the mental state of the subject by computing a probability of the mental state, wherein the mental state is task switching.

15. The mental state monitoring system of claim 10, wherein the heart rate monitor is further configured to measure body movement data with respect to the subject, wherein the heart rate monitor is at least one of a camera, a head movement monitor, an accelerometer, a radio wave disruption monitor, a photoplethysmography (PPG) monitor, or a sleep tracker, and wherein the classifier is further configured to:
  receive the body movement data; and
  classify the mental state of the subject based at least in part on the received body movement data.

16. The mental state monitoring system of claim 10, wherein the classifier is further configured to classify the mental state by computing a probability of the mental state, and wherein the mental state is selected from the group consisting of flow, motivation, overload, underload, attention, distraction, interruption, pleasure, misery, sleepiness, distress, excitement, busyness, task switching, depression, contentment, effortful attention, effortless attention, and a default mode of attention.

17. The mental state monitoring system of claim 10, further comprising:
a device usage tracker configured to measure one or more aspects of a usage of a computing device by the subject, wherein the one or more aspects comprises a difficulty level of a task that the subject is performing and a task progress level of the subject, wherein the classifier is further configured to classify the mental state of the subject based at least in part on the difficulty level and the task progress level.

18. The mental state monitoring system of claim 1, further comprising:
an eye blink rate monitor configured to measure a baseline eye blink rate of the subject,
wherein the first processor is configured to:
estimate a circadian rhythm of the subject; and
adjust the baseline eye blink rate based on the circadian rhythm to obtain an adjusted eye blink rate, and
wherein the classifier is further configured to:
receive the baseline eye blink rate and the adjusted eye blink rate; and
classify the mental state of the subject based at least in part on the received baseline eye blink rate and the adjusted eye blink rate.

19. The mental state monitoring system of claim 1, wherein, the notification blocker is further configured to:
determine whether to delay a device generated notification in response to the instruction,
wherein the second processor is further configured to:
determine a cost of a failure to receive the device generated notification based at least in part on the mental state of the subject;
compare the mental state classified at a first point in time to the mental state classified at a second point in time;
instruct the notification blocker to delay the device generated notification if the cost of the external interruption exceeds a second threshold; and
instruct the notification blocker to stop the delay of the device generated notification if an amount of time has passed after the second processor determines that the cost of the external interruption exceeds the second threshold, the mental state classified at the first point in time is different from the mental state classified at the second point in time, or the cost of the failure to receive the device generated notification exceeds the cost of the external interruption.

20. The mental state monitoring system of claim 1, wherein the classifier is further configured to:
classify the mental state of the subject by computing a probability of the mental state, wherein the mental state is task switching.

21. The mental state monitoring system of claim 1, wherein the heart rate monitor is further configured to measure body movement data with respect to the subject, wherein the heart rate monitor is at least one of a camera, a head movement monitor, an accelerometer, a radio wave disruption monitor, a photoplethysmography (PPG) monitor, or a sleep tracker, and wherein the classifier is further configured to:
receive the body movement data; and
classify the mental state of the subject based at least in part on the received body movement data.

22. The mental state monitoring system of claim 2, wherein the classifier is further configured to:
classify the mental state of the subject by computing a probability of the mental state, wherein the mental state is task switching.

23. The mental state monitoring system of claim 2, wherein the first processor is configured to:
extract an idealized respiratory waveform from the breathing data, wherein the idealized respiratory waveform comprises variations across time in an interval between two inhale peaks or two exhale peaks; and
remove a respiratory influence from the heart rate variability signal using the idealized respiratory waveform,
wherein the classifier is further configured to:
receive the heart rate variability signal after the respiratory influence is removed and;
classify the mental state of the subject based at least in part on the received heart rate variability signal.

24. The mental state monitoring system of claim 2, further comprising:
a notification blocker configured to:
receive an instruction from the second processor; and
determine whether to delay a device generated notification in response to the instruction,
wherein the second processor is configured to:
determine a cost of an external interruption based at least in part on the mental state of the subject, wherein the external interruption is generated by a person or a computing device;
determine a cost of a failure to receive the device generated notification based at least in part on the mental state of the subject;
compare the mental state classified at a first point in time to the mental state classified at a second point in time;
instruct the notification blocker to delay the device generated notification if the cost of the external interruption exceeds a threshold; and
instruct the notification blocker to stop the delay of the device generated notification if an amount of time has passed after the second processor determines that the cost of the external interruption exceeds the threshold, the mental state classified at the first point in time is different from the mental state classified at the second point in time, or the cost of the failure to receive the device generated notification exceeds the cost of the external interruption.

25. The mental state monitoring system of claim 6, wherein the system is configured to:
increase or decrease the task difficulty level one or more times based at least in part on the task progress level until the classifier has classified the mental state as flow or absence of overload.

26. The mental state monitoring system of claim 3, wherein the mental state is flow, default mode of attention, busyness, or overload.

27. The mental state monitoring system of claim 8, wherein the second processor is further configured to determine the cost of the external interruption based at least in part on the mental state of the subject and an identity of a task being performed by the subject.

* * * * *